US011422363B2

(12) United States Patent
Hattori et al.

(10) Patent No.: US 11,422,363 B2
(45) Date of Patent: Aug. 23, 2022

(54) ADAPTIVE OPTICS SYSTEM AND OPTICAL DEVICE

(71) Applicant: INTER-UNIVERSITY RESEARCH INSTITUTE CORPORATION NATIONAL INSTITUTES OF NATURAL SCIENCES, Tokyo (JP)

(72) Inventors: Masayuki Hattori, Hilo, HI (US); Yosuke Tamada, Okazaki (JP); Takashi Murata, Okazaki (JP); Yasuhiro Kamei, Okazaki (JP); Mitsuyasu Hasebe, Okazaki (JP); Yutaka Hayano, Hilo, HI (US); Shin Oya, Hilo, HI (US)

(73) Assignee: INTER-UNIVERSITY RESEARCH INSTITUTE CORPORATION NATIONAL INSTITUTES OF NATURAL SCIENCES, Tokyo (JP)

( * ) Notice: Subject to any disclaimer, the term of this patent is extended or adjusted under 35 U.S.C. 154(b) by 0 days.

(21) Appl. No.: 16/283,175

(22) Filed: Feb. 22, 2019

(65) Prior Publication Data

US 2019/0258053 A1    Aug. 22, 2019

Related U.S. Application Data

(63) Continuation of application No. 15/023,281, filed as application No. PCT/JP2014/074837 on Sep. 19, 2014, now Pat. No. 10,254,538.

(30) Foreign Application Priority Data

Sep. 20, 2013 (JP) .................................. 2013-195943

(51) Int. Cl.
   *G02B 21/06* (2006.01)
   *G02B 21/00* (2006.01)
   (Continued)

(52) U.S. Cl.
   CPC ............ *G02B 27/0068* (2013.01); *G01J 9/00* (2013.01); *G02B 17/008* (2013.01);
   (Continued)

(58) Field of Classification Search
   CPC ............. G02B 27/0068; G02B 17/008; G02B 21/002; G02B 21/0096; G02B 21/02; G02B 21/06; G01J 9/00; G01J 2009/002
   See application file for complete search history.

(56) References Cited

U.S. PATENT DOCUMENTS 6,452,146 B1    9/2002 Barchers
10,254,538 B2 *  4/2019 Hattori .................. G02B 21/06
(Continued)

FOREIGN PATENT DOCUMENTS

EP    1 609 405 A1    12/2005
EP    2 460 462 A1     6/2012
(Continued)

OTHER PUBLICATIONS

P. Paudel, John Taranto, Jerome Mertz, and Thomas Bifano, "Axial range of conjugate adaptive optics in two-photon microscopy," Opt. Express 23, 20849-20857 (2015) (Year: 2015).*
(Continued)

*Primary Examiner* — Alicia M Harrington
(74) *Attorney, Agent, or Firm* — Birch, Stewart, Kolasch & Birch, LLP

(57) ABSTRACT

The present invention is intended to provide an adaptive optics system and an optical device that allow correction of wavefront phase aberration with higher accuracy than before and have a wider correction range than the conventional ones, regardless of the distance between the observation target and the fluctuation layer, and the size of the observation target. An adaptive optics system includes: a wavefront phase modulator that makes aberration correction to incident
(Continued)

light and emits the corrected light; and an imaging-conjugated position adjustment mechanism that adjusts freely within a specimen the position of a surface imaging-conjugated with a fluctuation correction surface formed by the wavefront phase modulator. The imaging-conjugated position adjustment mechanism adjusts the fluctuation correction surface to be imaging-conjugated with a fluctuation layer existing in the specimen.

20 Claims, 33 Drawing Sheets

(51) Int. Cl.
| | |
|---|---|
| *G01J 9/00* | (2006.01) |
| *G02B 17/00* | (2006.01) |
| *G02B 21/02* | (2006.01) |
| *G02B 21/18* | (2006.01) |
| *G01N 21/64* | (2006.01) |
| *G02B 27/00* | (2006.01) |
| *G02B 21/36* | (2006.01) |
| *G01N 21/17* | (2006.01) |
| *A61B 5/00* | (2006.01) |

(52) U.S. Cl.
CPC ....... *G02B 21/002* (2013.01); *G02B 21/0096* (2013.01); *G02B 21/02* (2013.01); *G02B 21/06* (2013.01); *G02B 21/18* (2013.01); *G02B 21/361* (2013.01); *G02B 21/367* (2013.01); *G02B 27/0025* (2013.01); *A61B 5/0059* (2013.01); *A61B 5/0068* (2013.01); *A61B 5/0071* (2013.01); *G01J 2009/002* (2013.01); *G01N 21/6458* (2013.01); *G01N 2021/1787* (2013.01)

(56) References Cited

U.S. PATENT DOCUMENTS

| | | |
|---|---|---|
| 2003/0053026 A1 | 3/2003 | Roorda |
| 2007/0247638 A1 | 10/2007 | Owner-Petersen et al. |
| 2007/0291230 A1 | 12/2007 | Yamaguchi et al. |
| 2009/0284831 A1 | 11/2009 | Schuster et al. |
| 2011/0006231 A1 | 1/2011 | Betzig et al. |
| 2011/0279778 A1 | 11/2011 | Saito |
| 2012/0127552 A1* | 5/2012 | Murayama ........... G02B 21/002 359/201.2 |
| 2013/0215385 A1 | 8/2013 | Hirose |
| 2013/0250391 A1* | 9/2013 | Kato ................... G02B 21/082 359/238 |
| 2014/0104618 A1* | 4/2014 | Potsaid .............. G01B 9/02055 356/497 |

FOREIGN PATENT DOCUMENTS

| | | |
|---|---|---|
| JP | 2002-40368 A | 2/2002 |
| JP | 2005-501587 A | 1/2005 |
| JP | 2009-540586 A | 11/2009 |
| JP | 2011-180290 A | 9/2011 |
| JP | 2011-239884 A | 12/2011 |
| JP | 2012-533069 A | 12/2012 |
| WO | WO 2007/120112 A1 | 10/2007 |

OTHER PUBLICATIONS

Eric E Bloemhof, J. Kent Wallace, "Phase contrast techniques for wavefront sensing and calibration in adaptive optics," Proc. SPIE 5169, Astronomical Adaptive Optics Systems and Applications, (Dec. 24, 2003); (Year: 2003).*

Extended European Search Report dated Apr. 19, 2017, in European Patent Application No. 14845892.0.

Written Opinion of the International Searching Authority dated Dec. 16, 2014, in PCT International Application No. PCT/JP2014/074837, with English translation.

* cited by examiner

[Fig. 1]
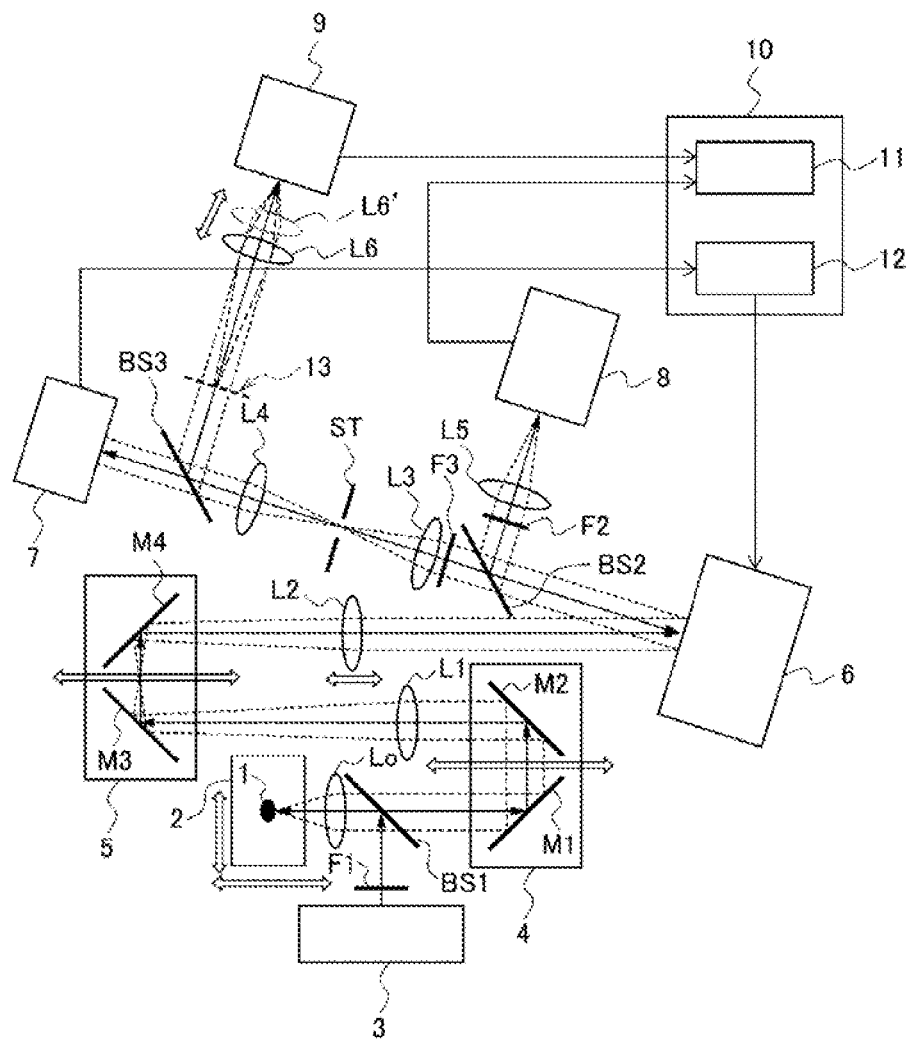

[Fig. 2]
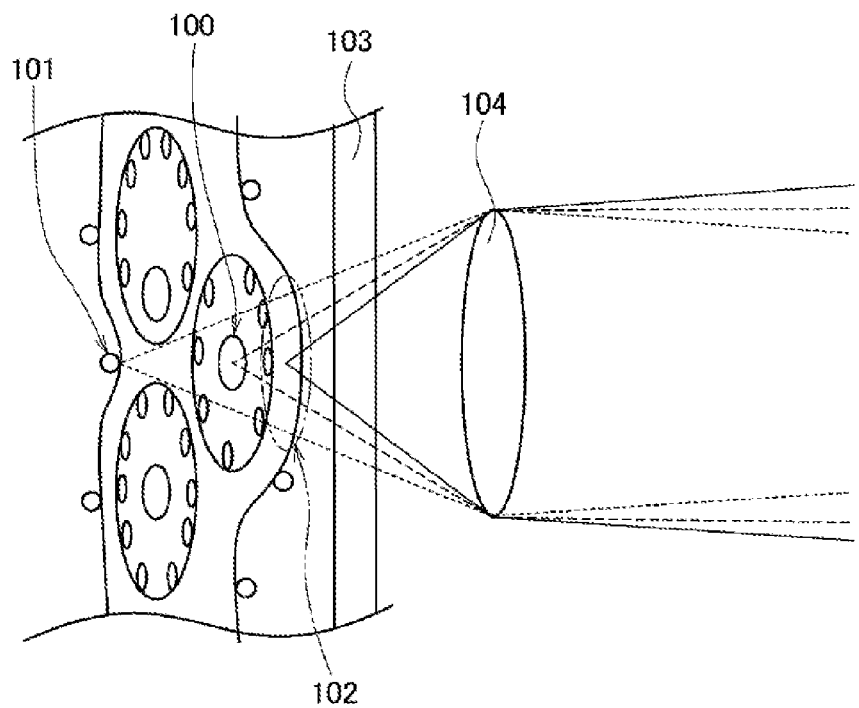
[Fig. 3]
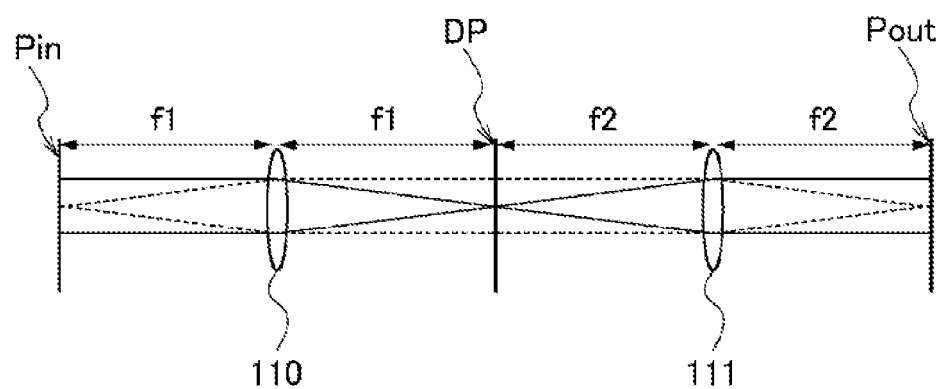

[Fig. 4]
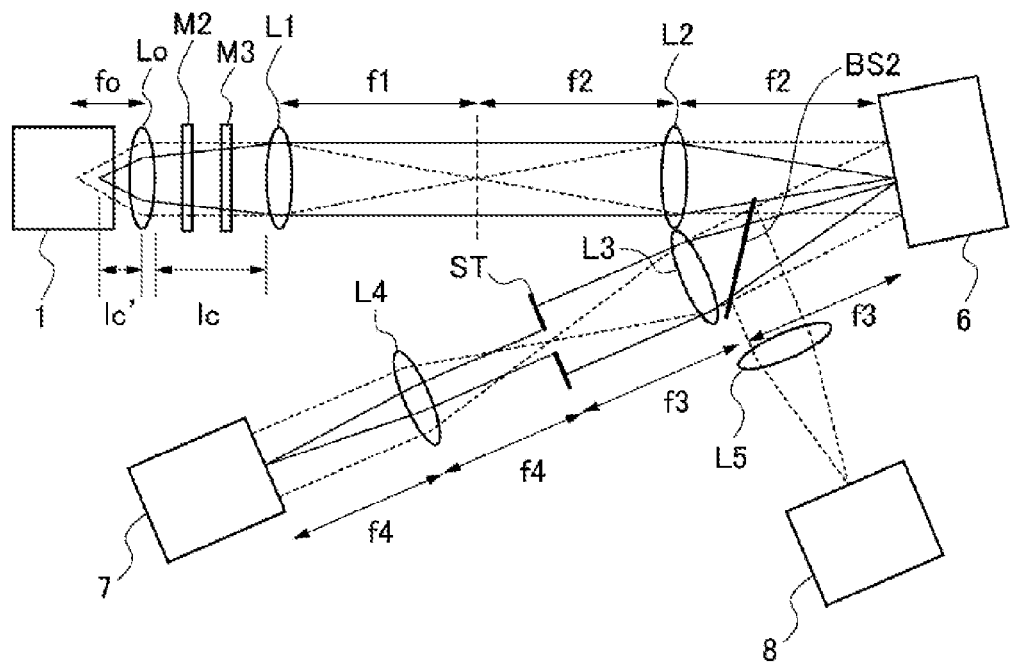

[Fig. 7]
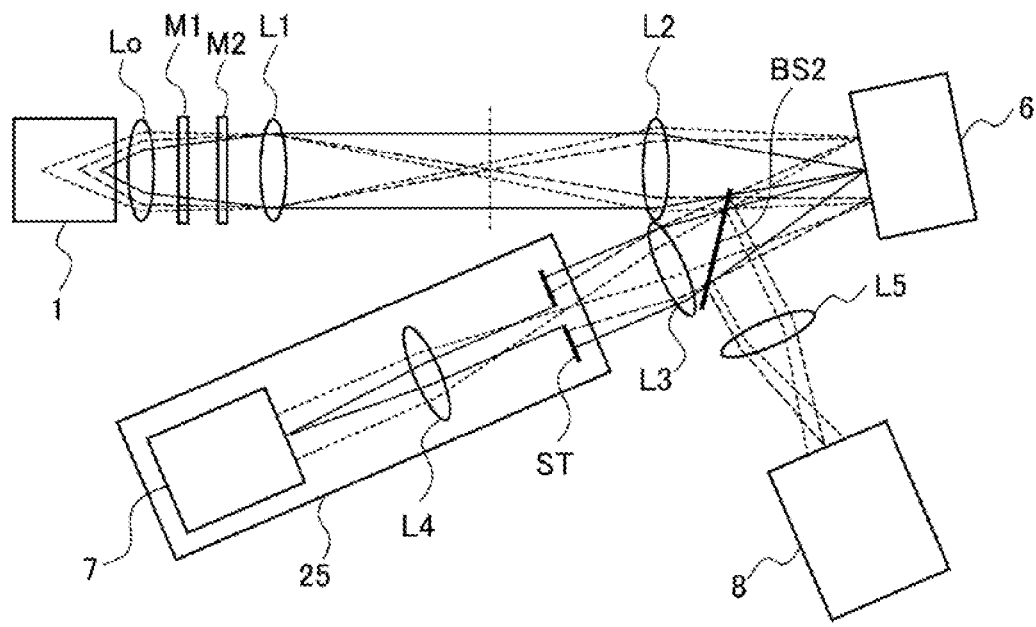
[Fig. 8]
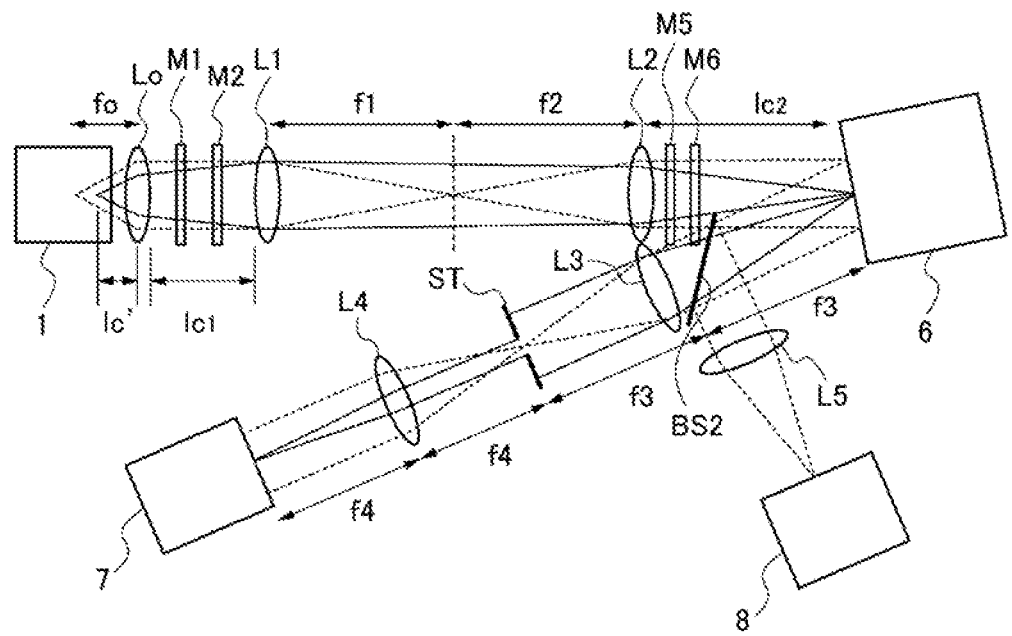

[Fig. 10]
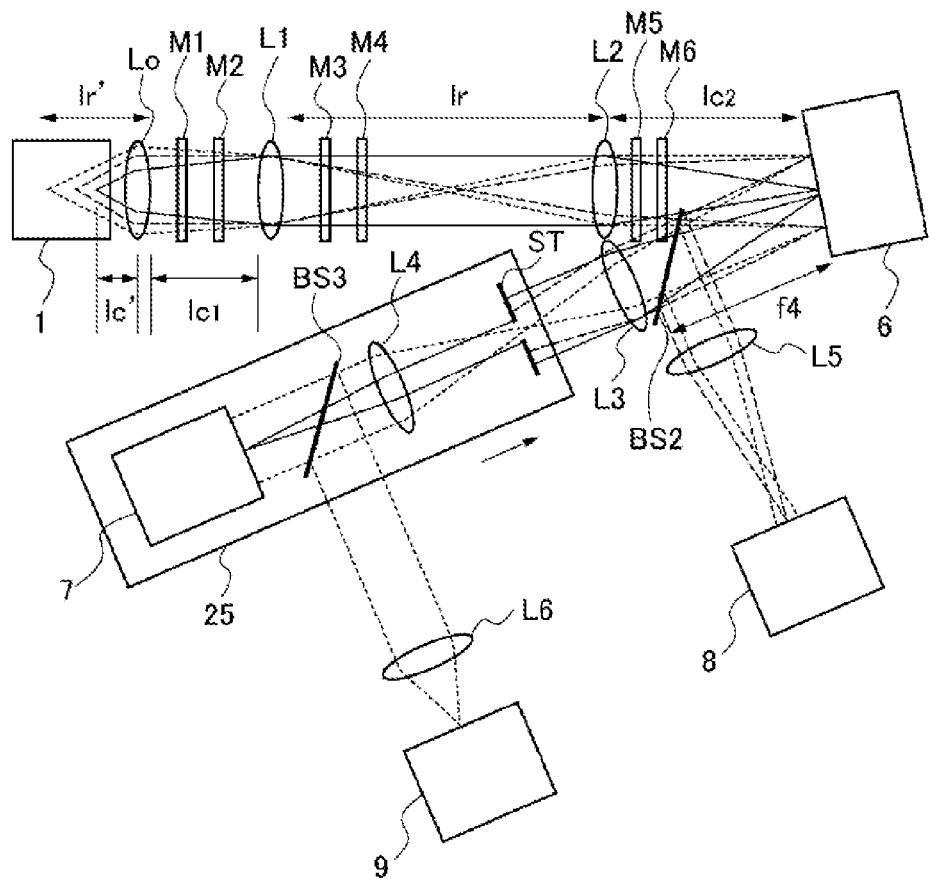
[Fig. 11]
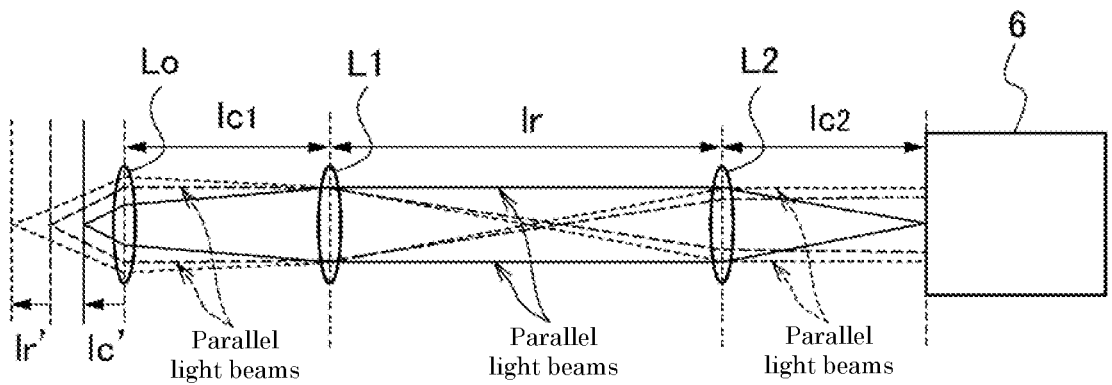

[Fig. 12]
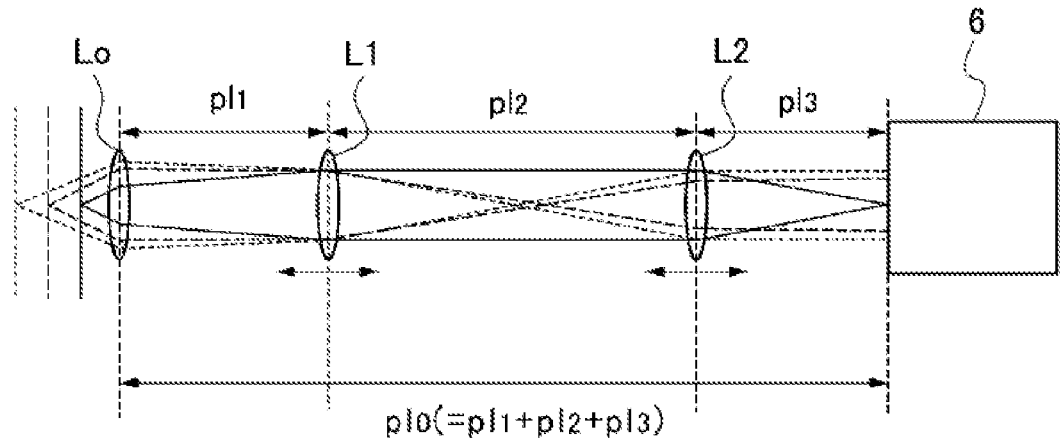
[Fig. 13]
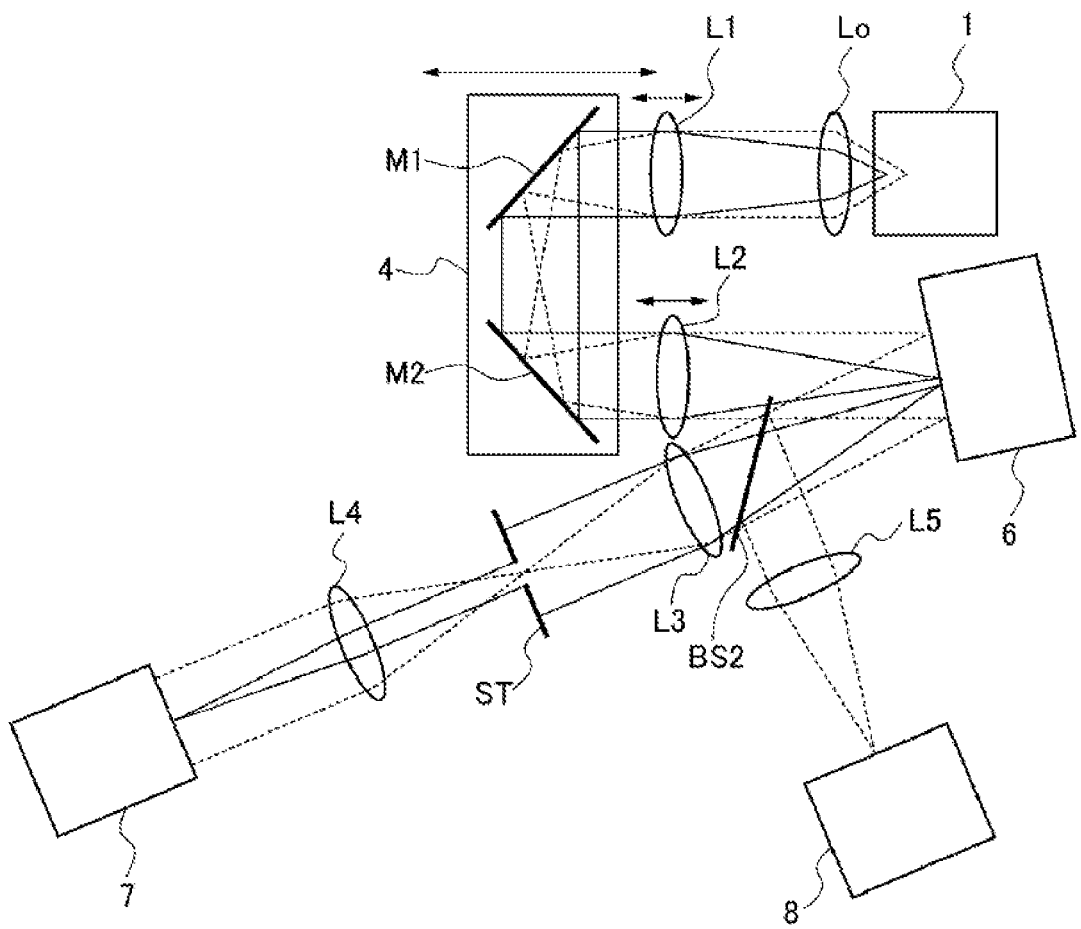

[Fig. 14]
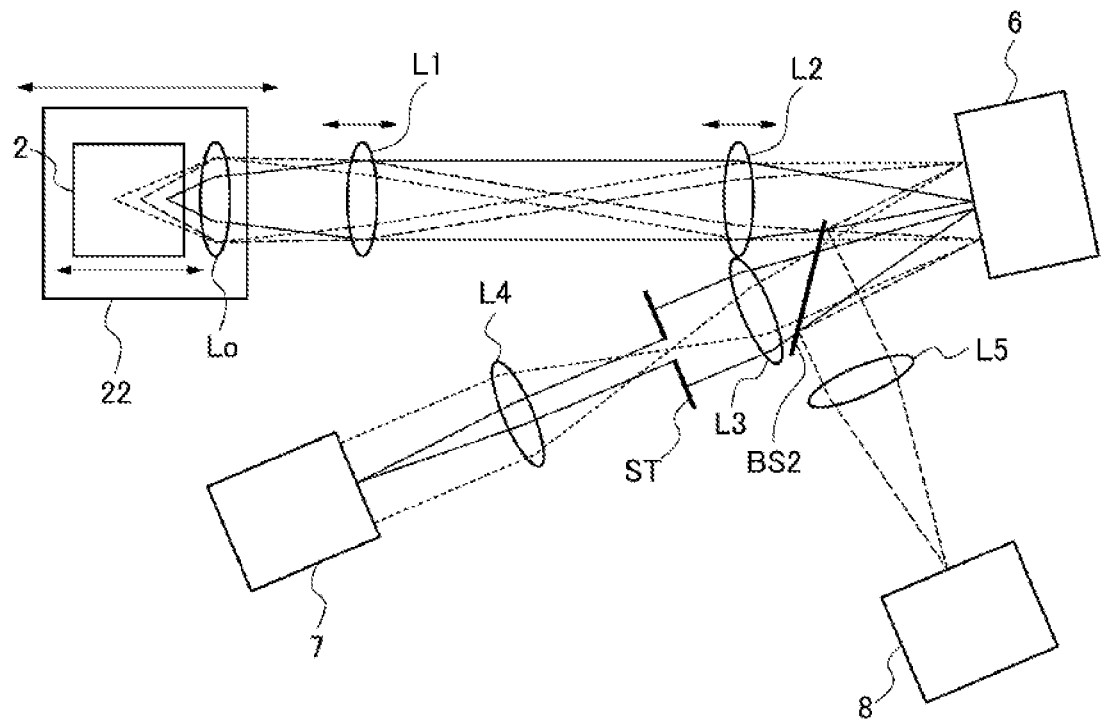

[Fig. 15]
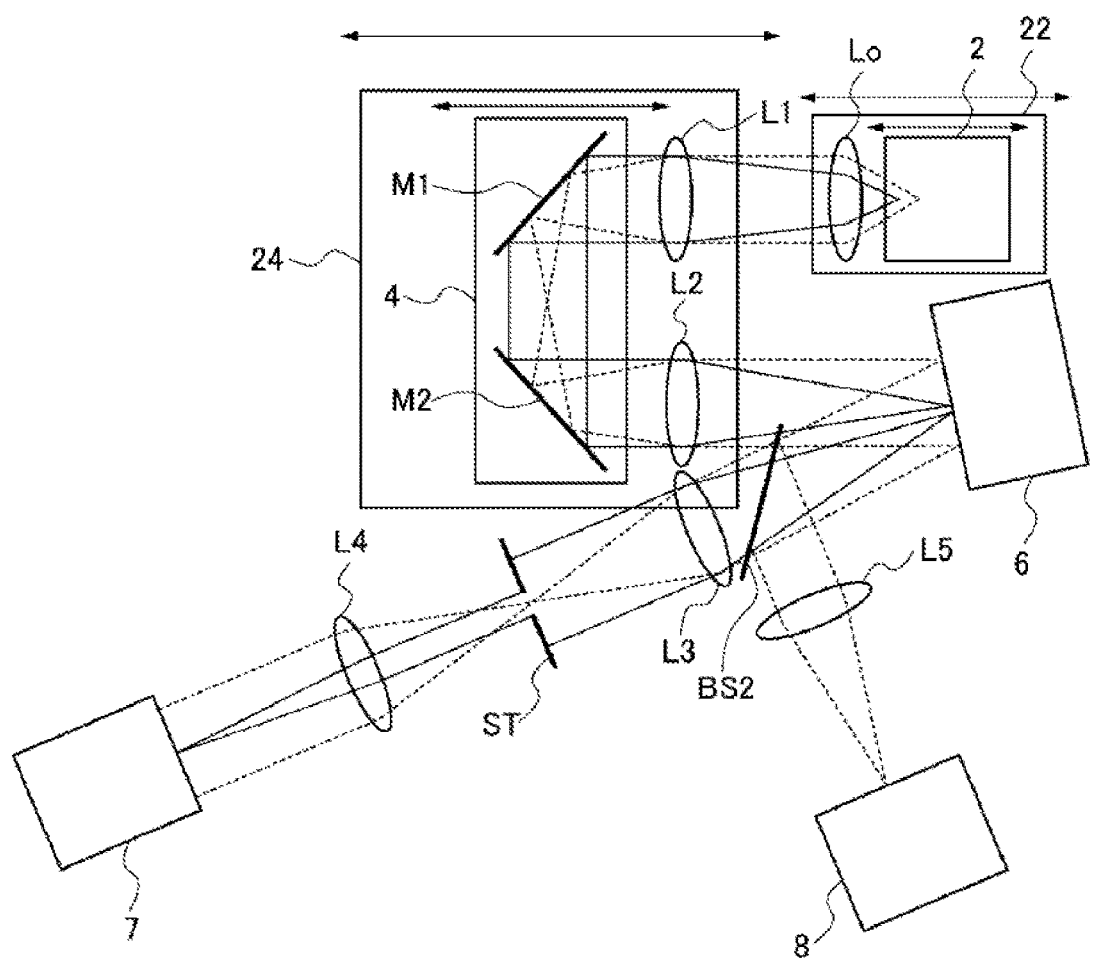

[Fig. 16]
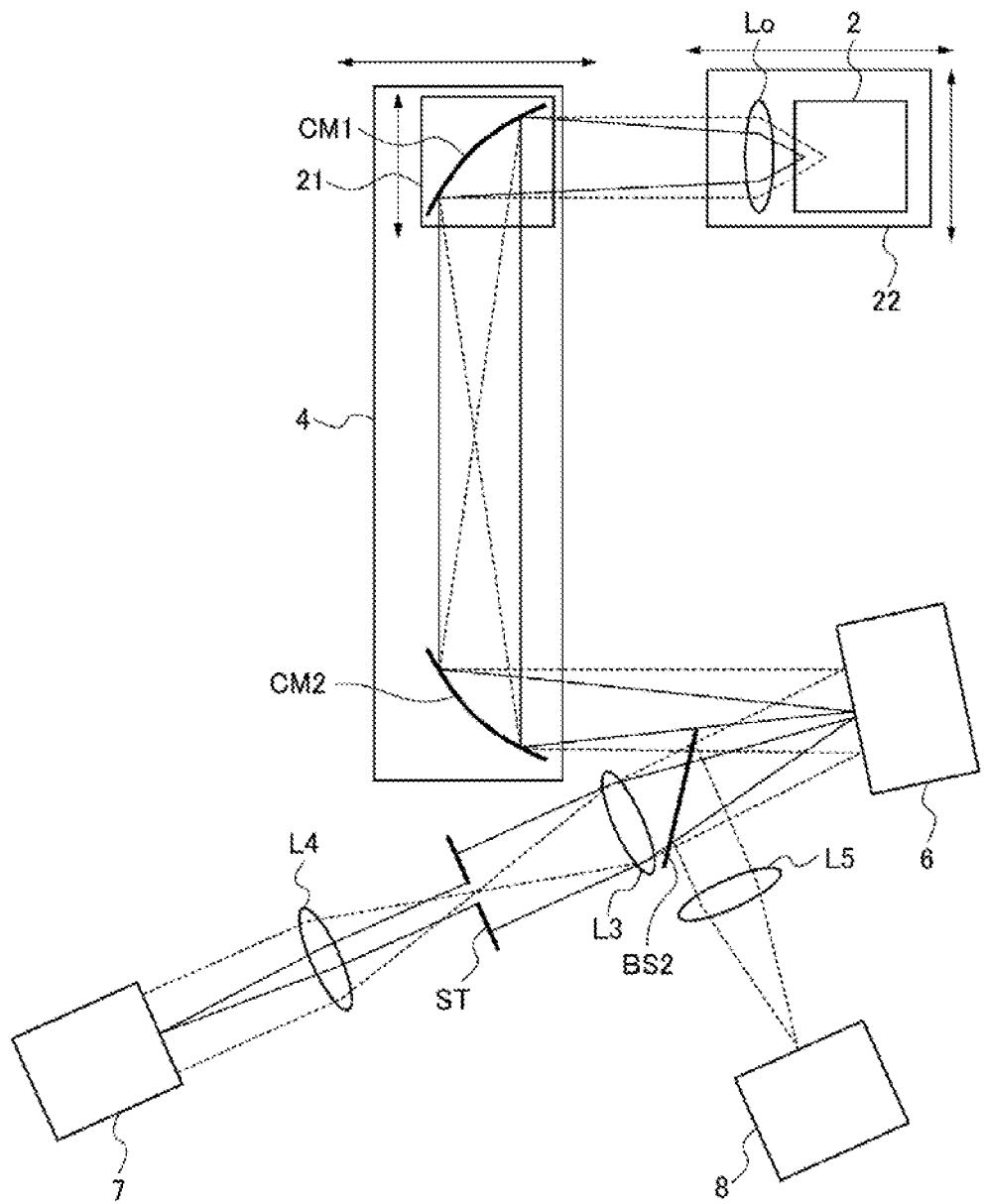

[Fig. 17]
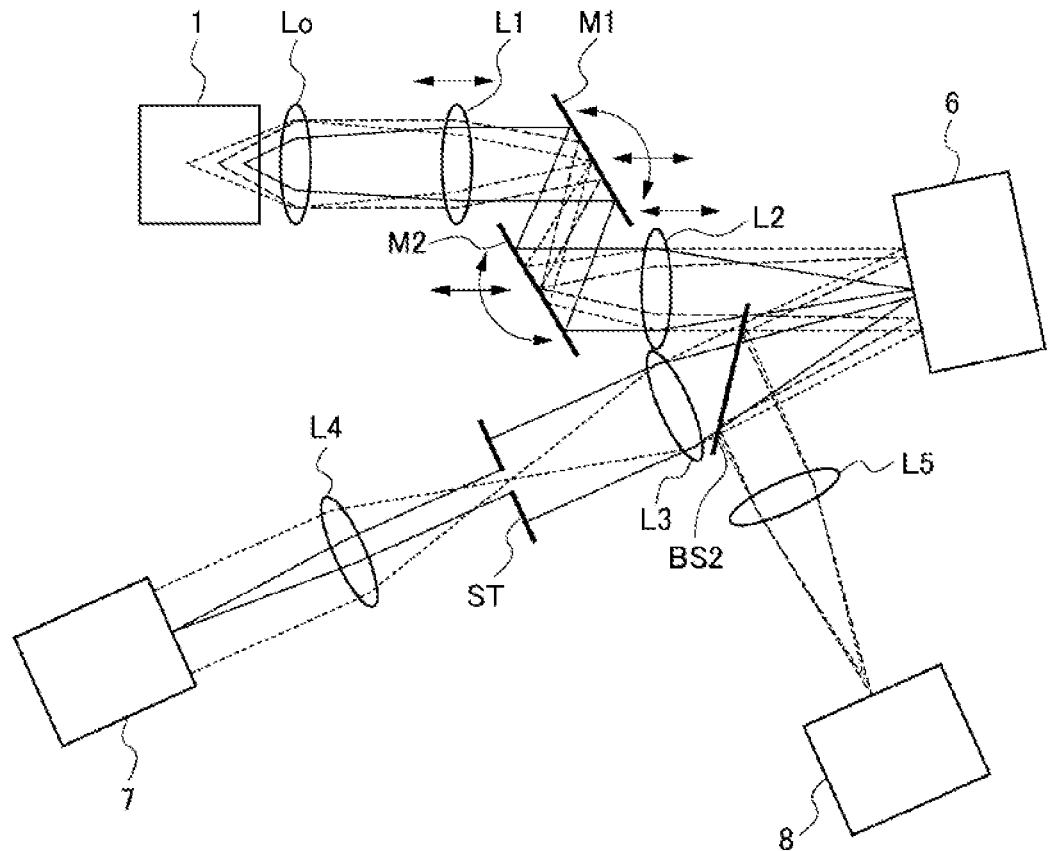
[Fig. 18]
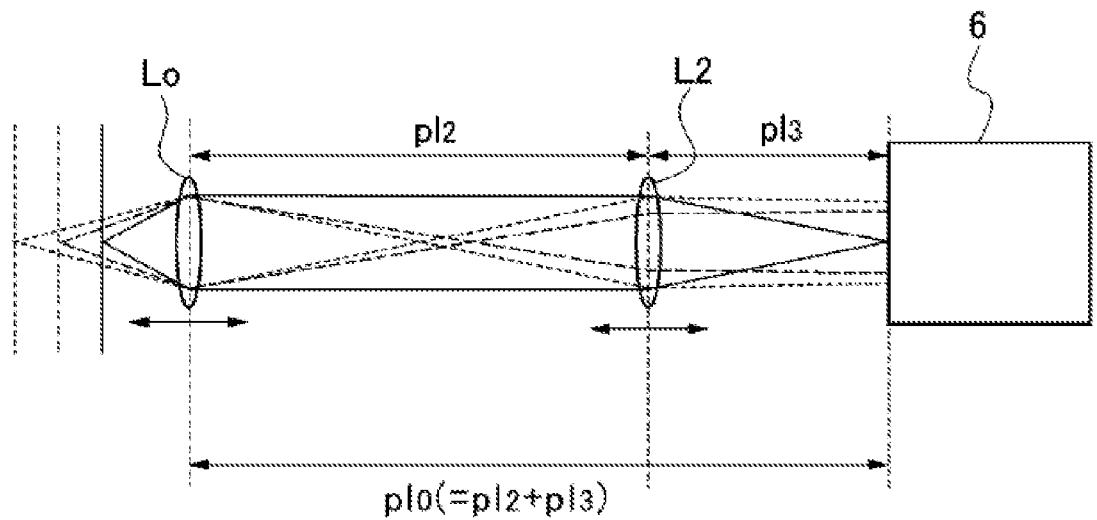

[Fig. 19]
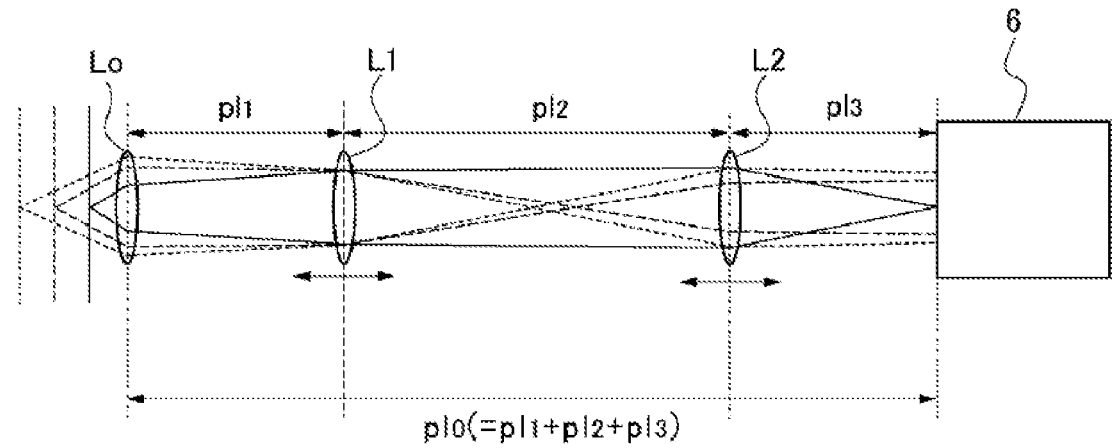
[Fig. 20]
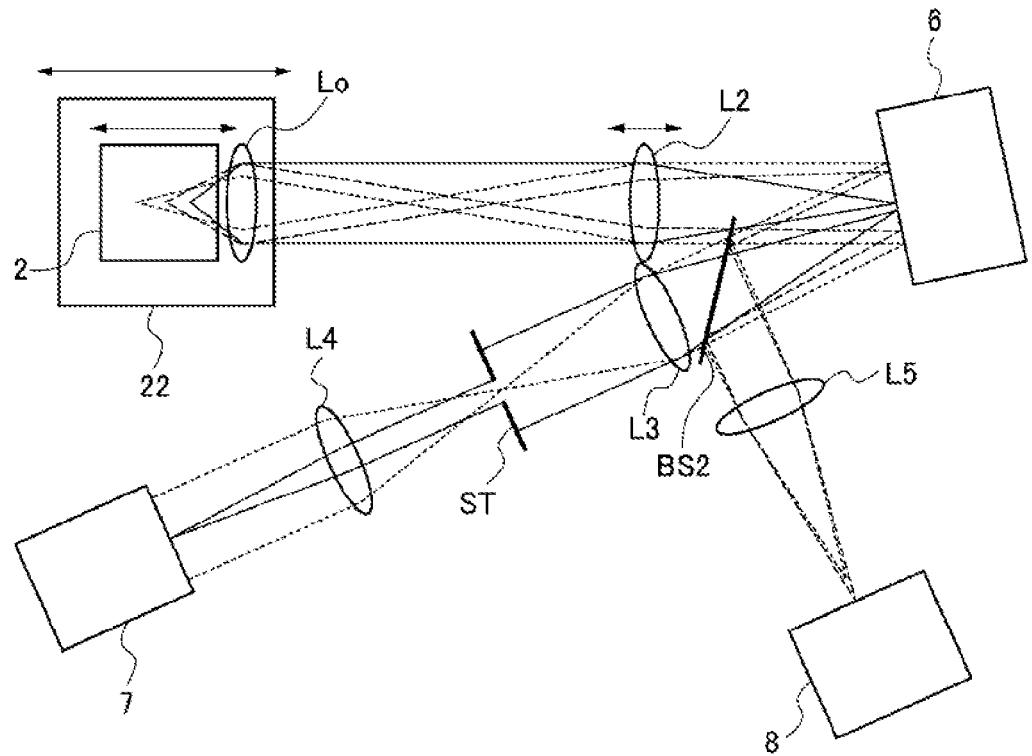

[Fig. 22]
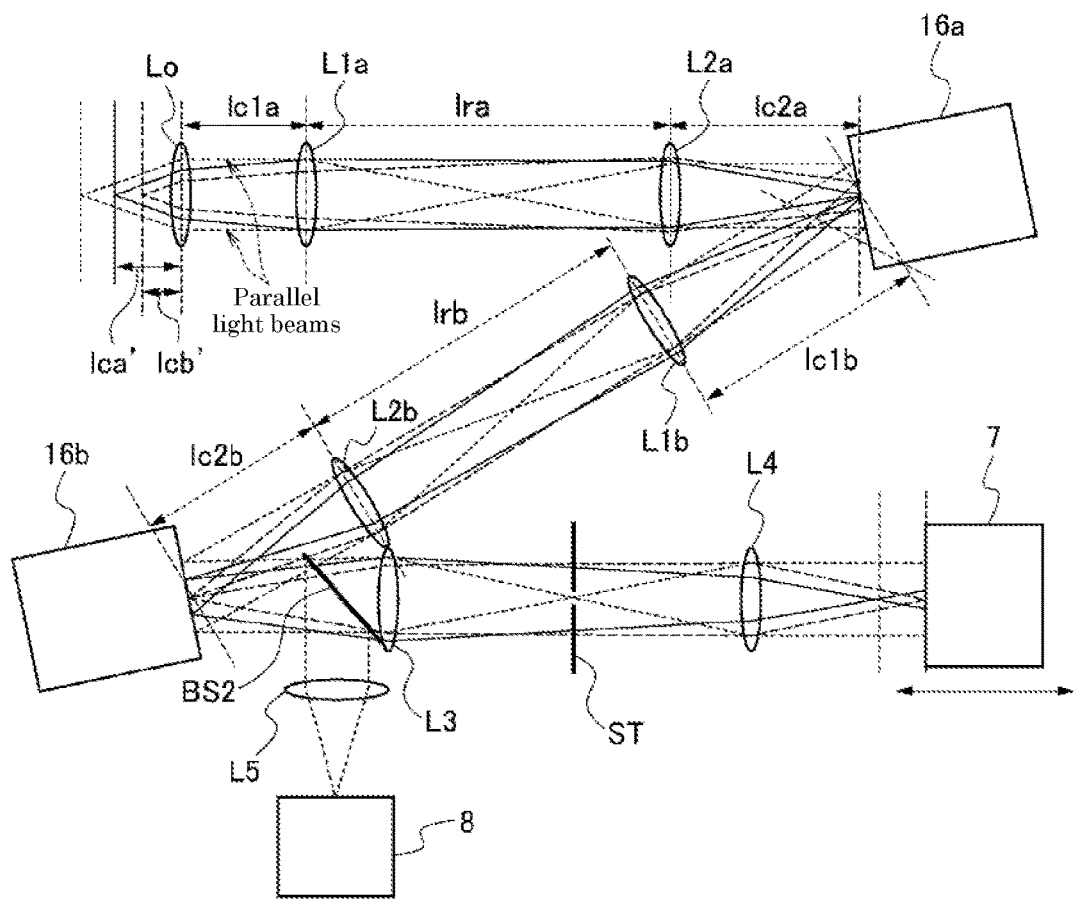

[Fig. 23]
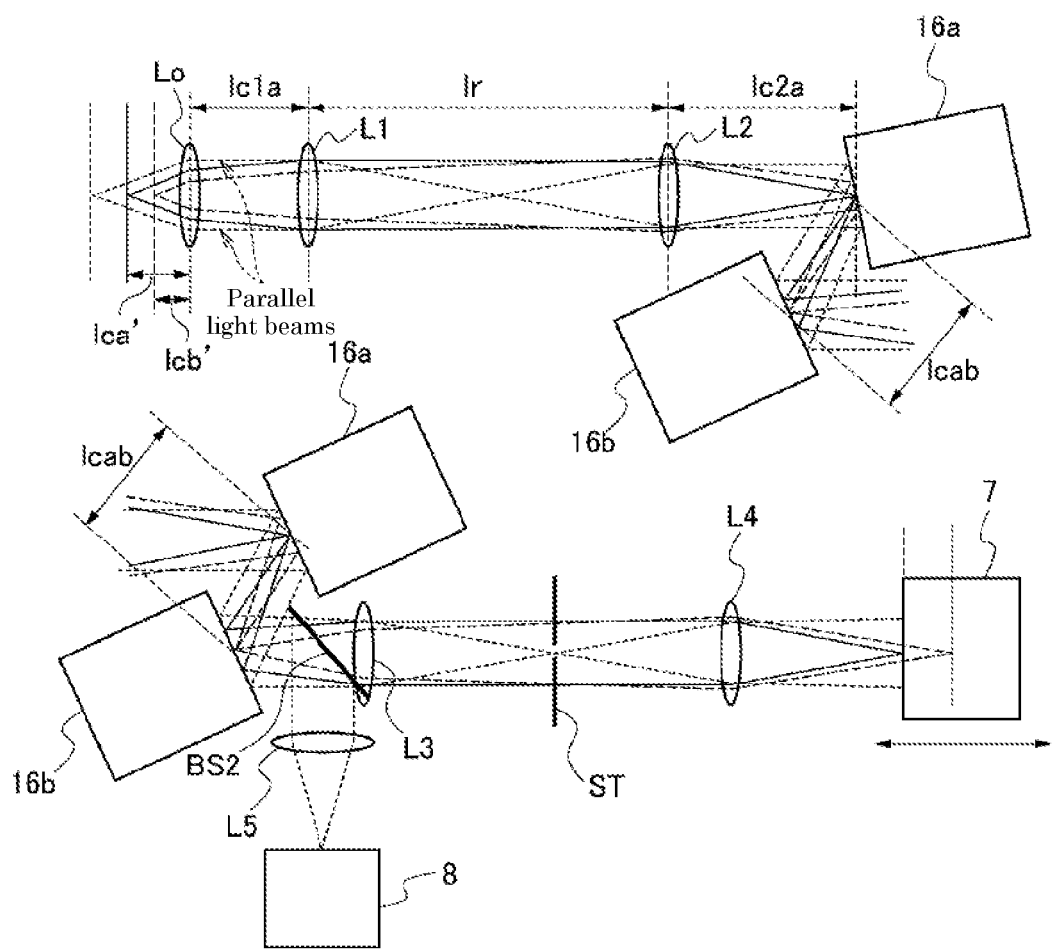

[Fig. 24]
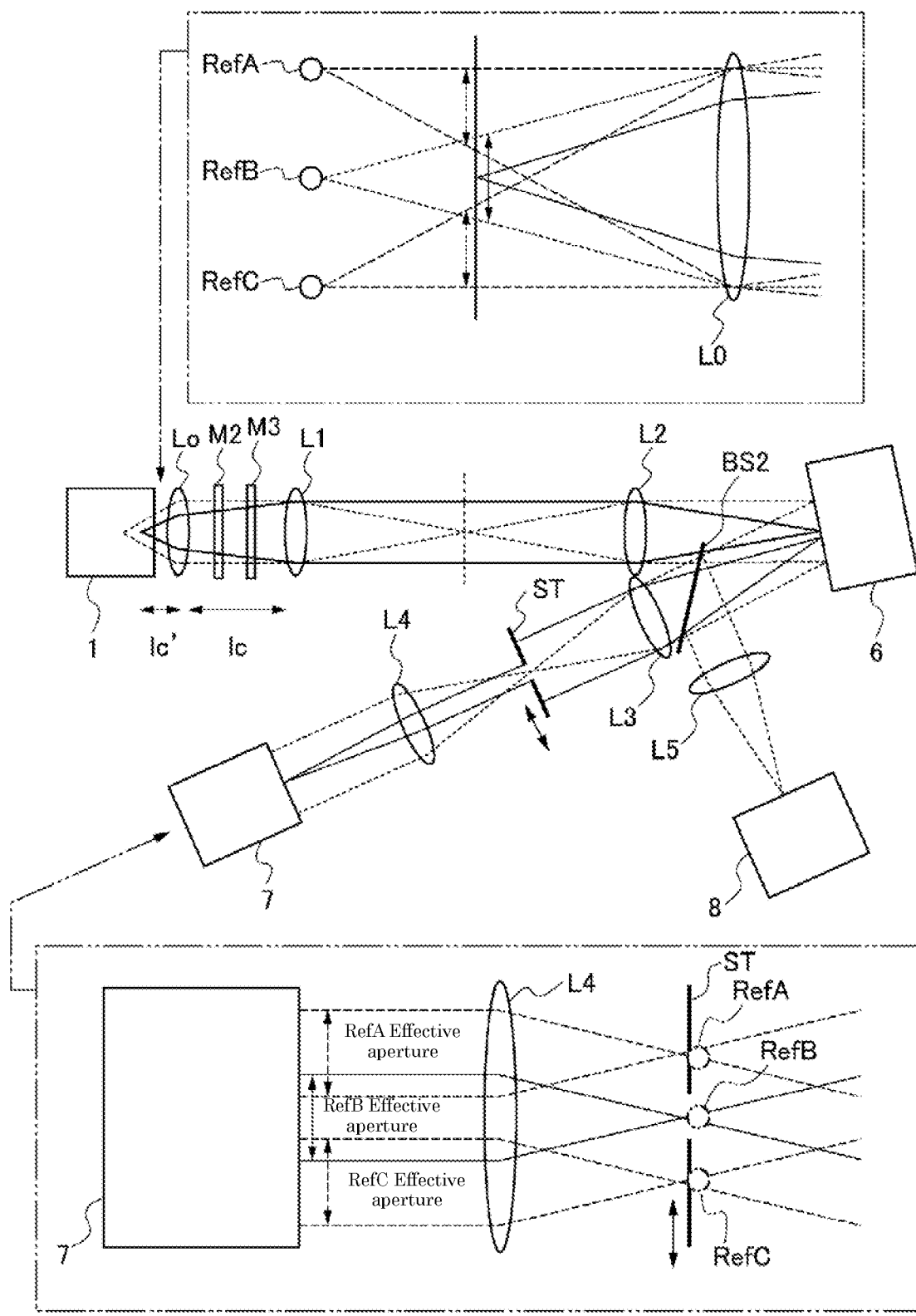

[Fig. 25]
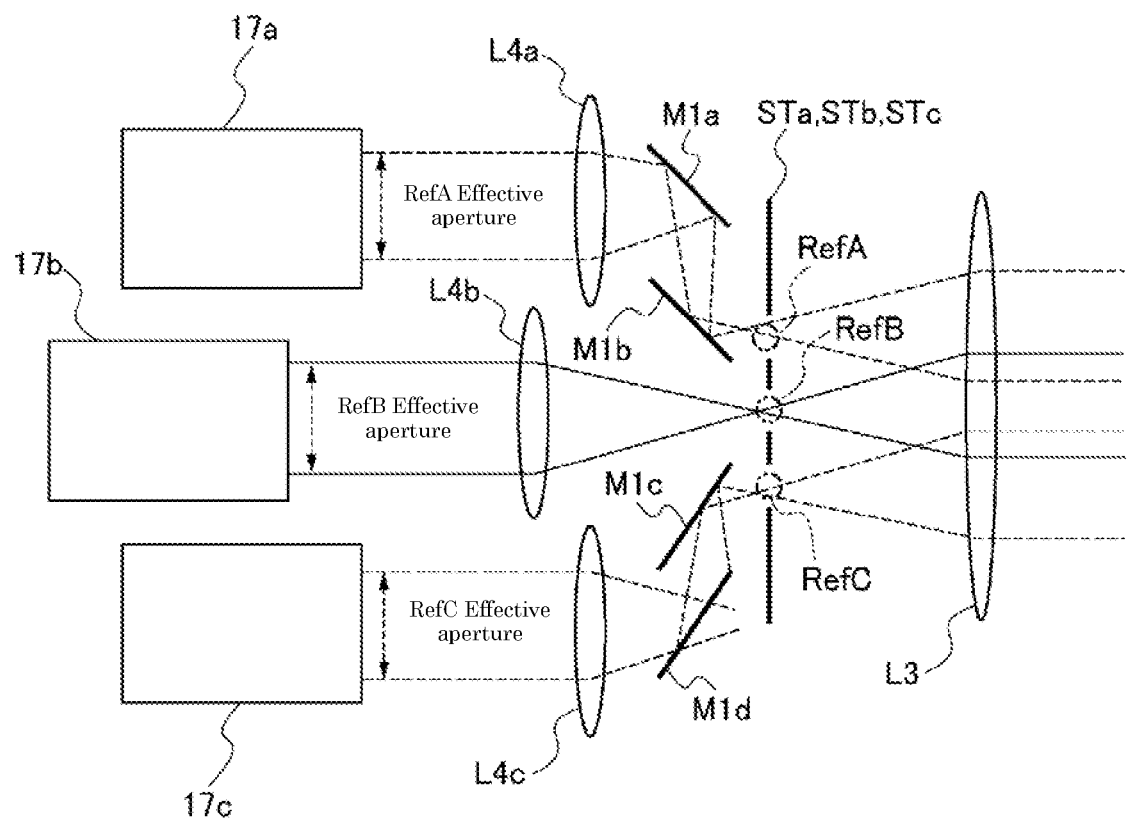
[Fig. 26]
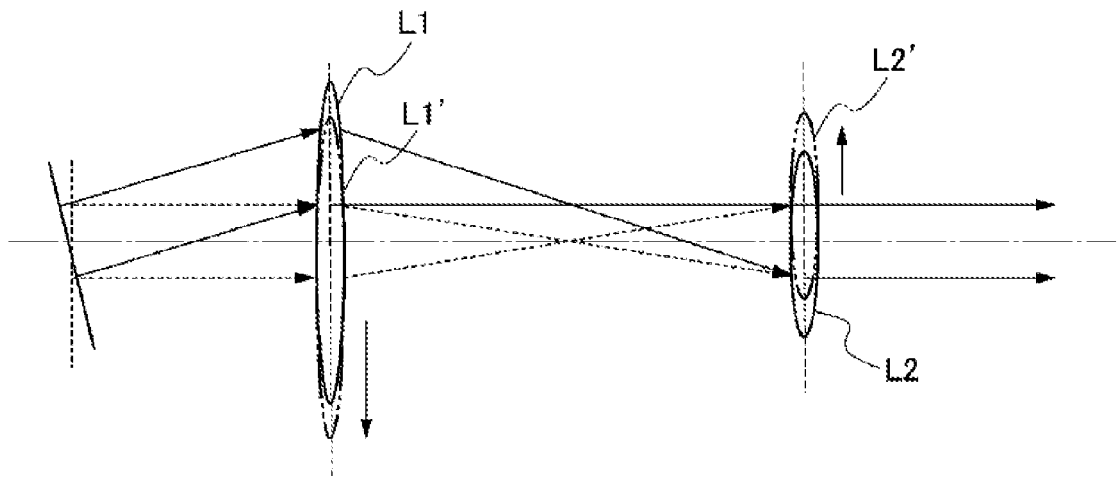

[Fig. 27]
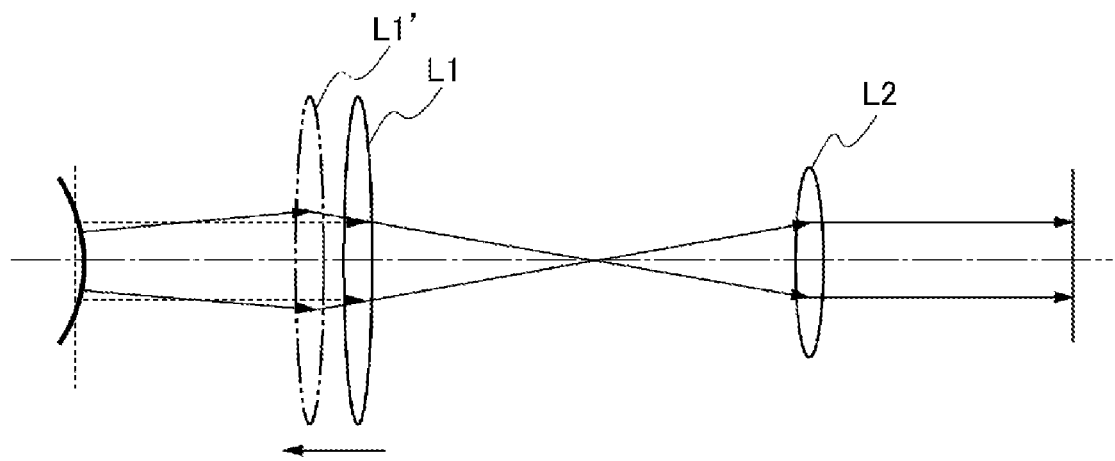
[Fig. 28]
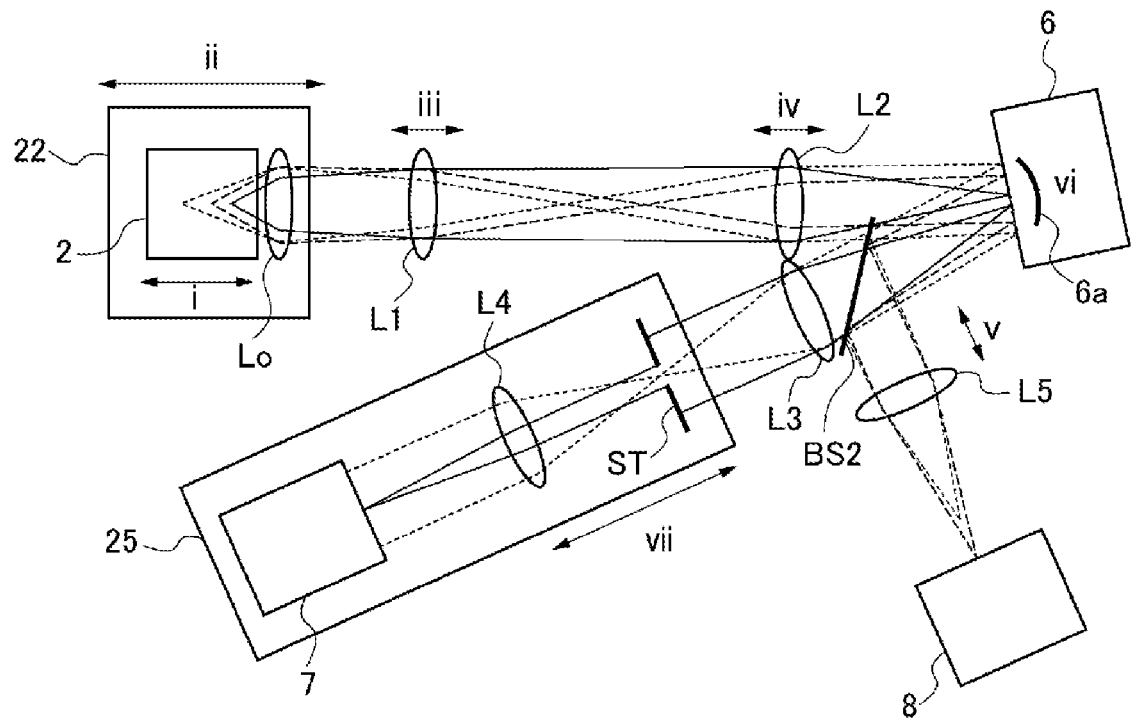

[Fig. 29]
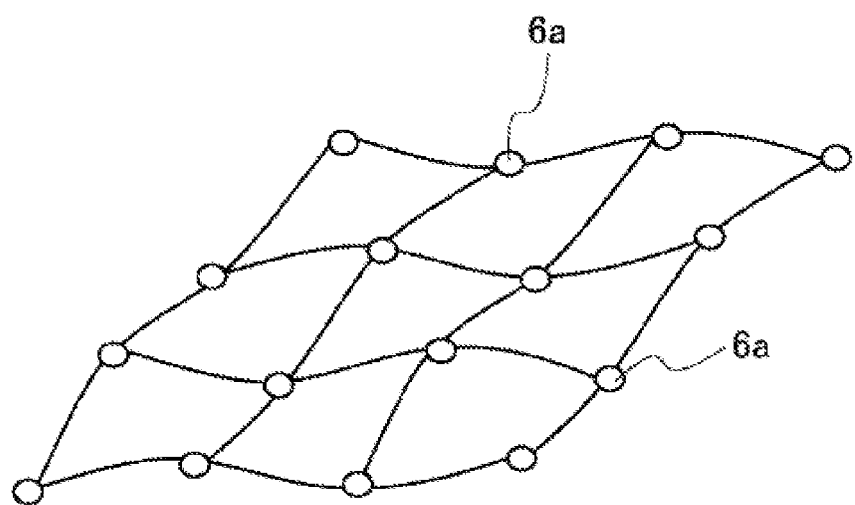

[Fig. 33]
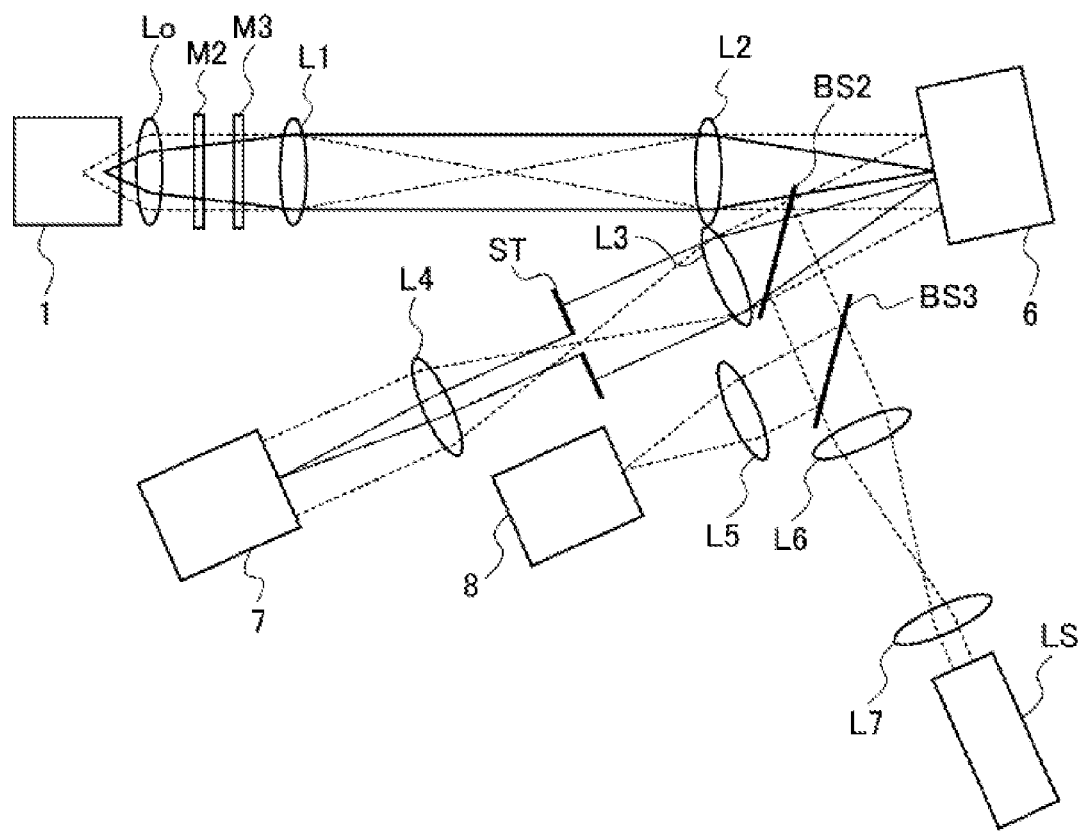

[Fig. 34]
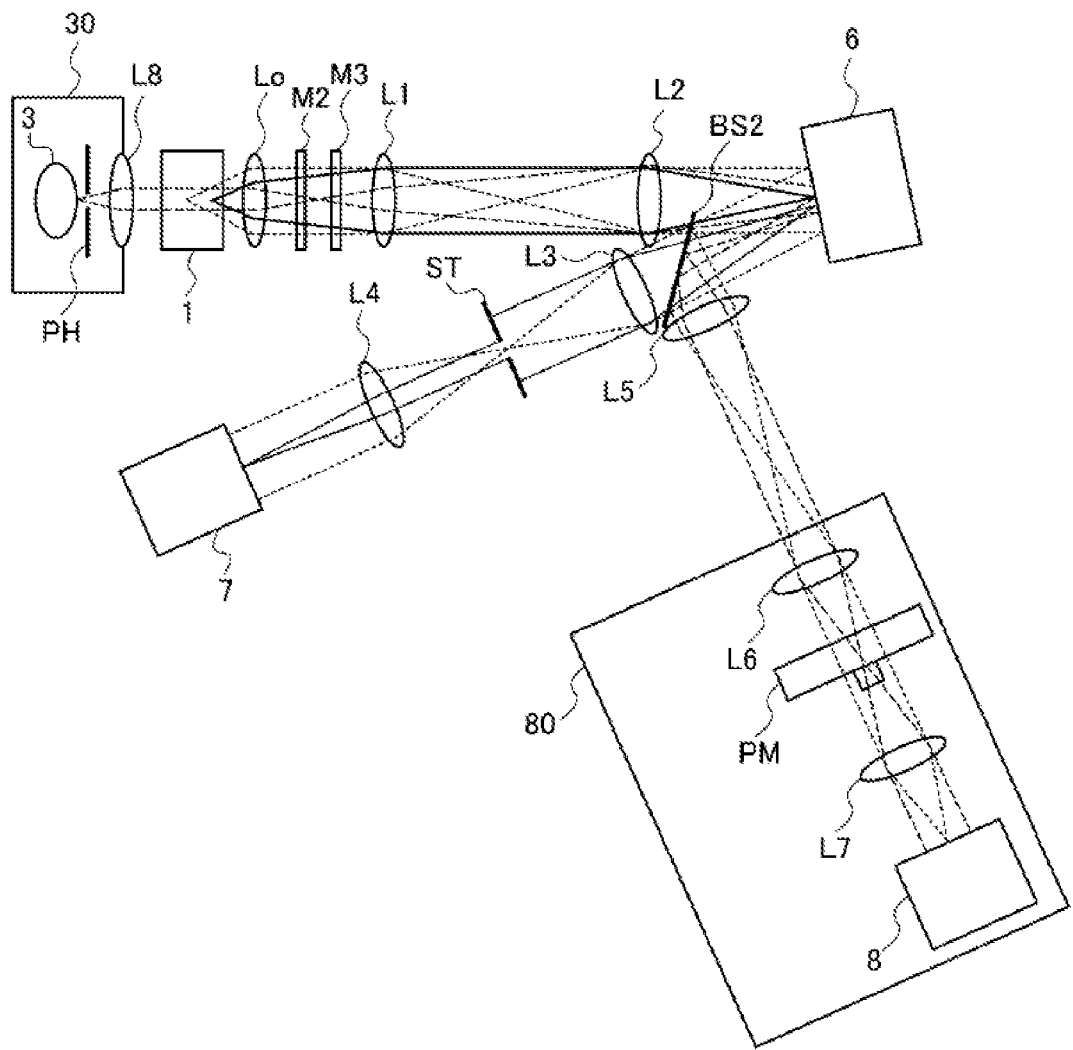

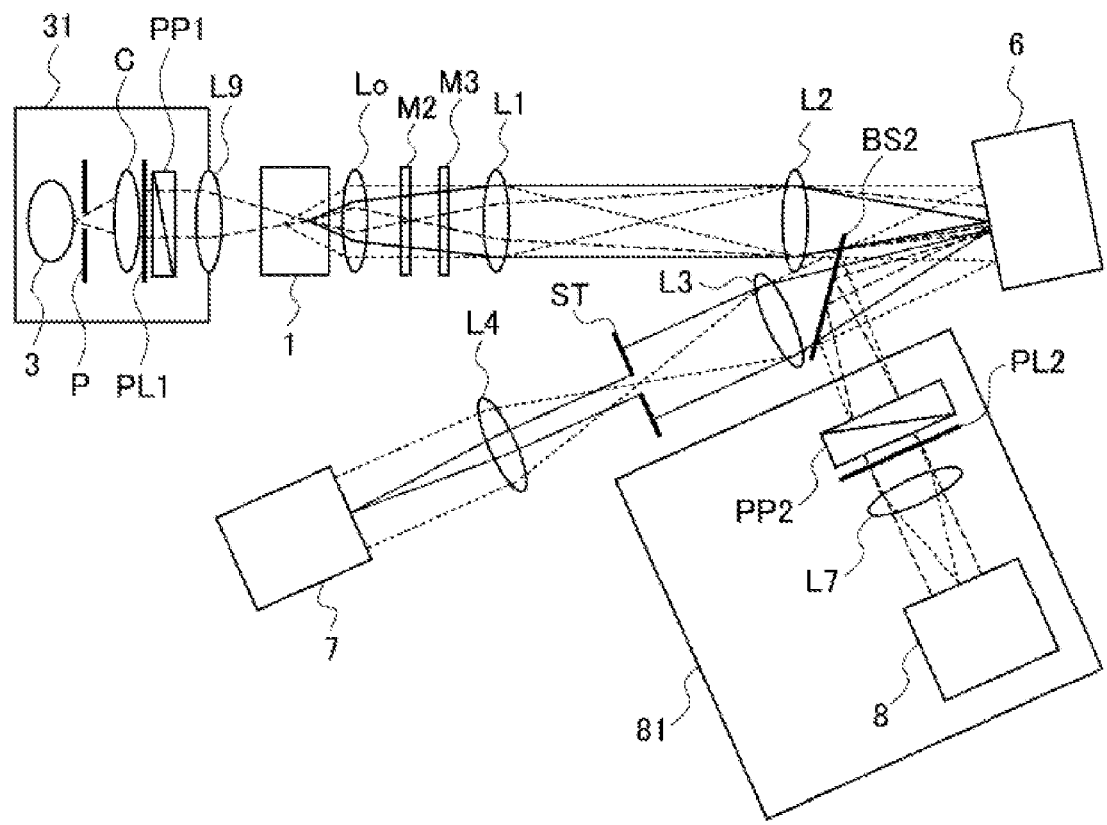
[Fig. 35]

[Fig. 36]
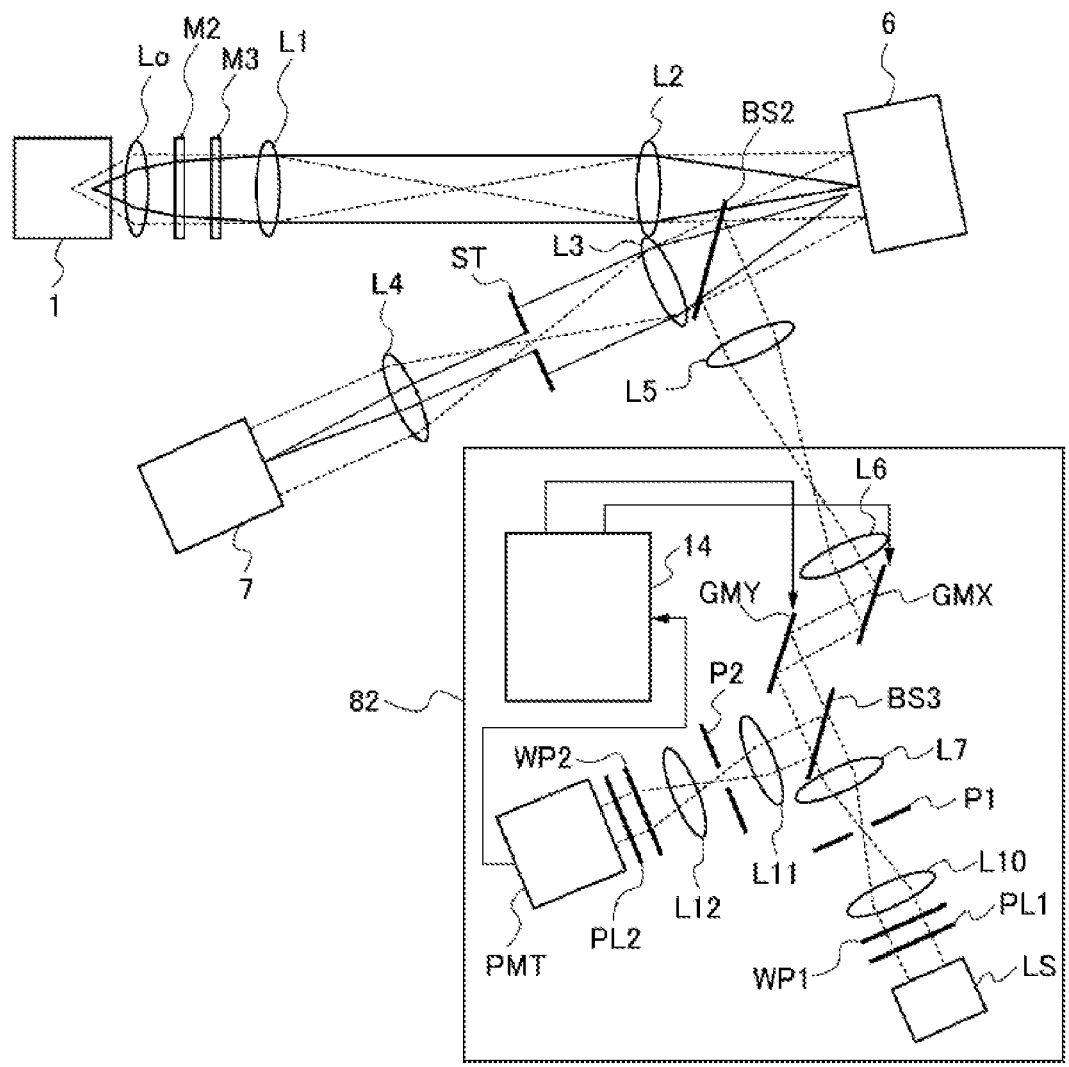

[Fig. 37]
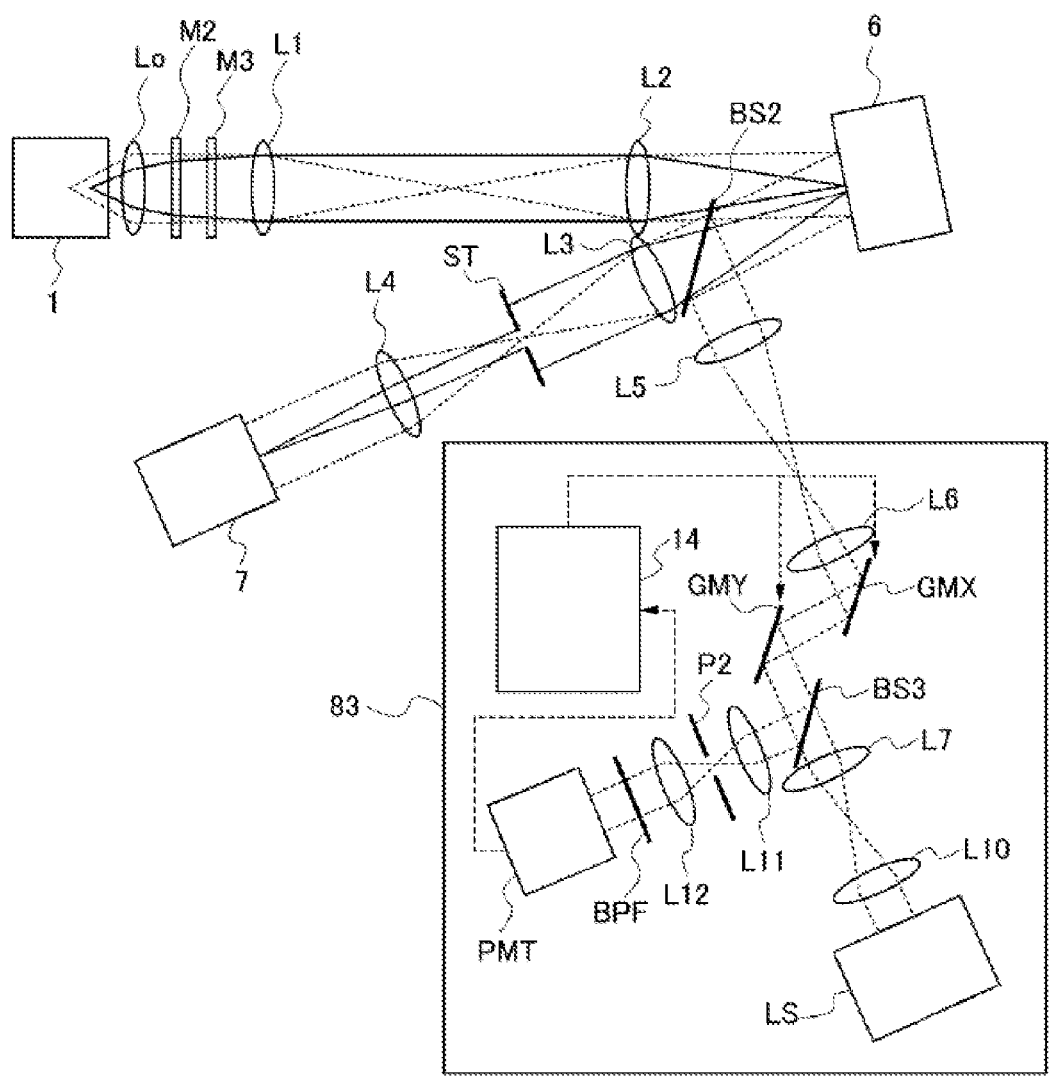

[Fig. 38]
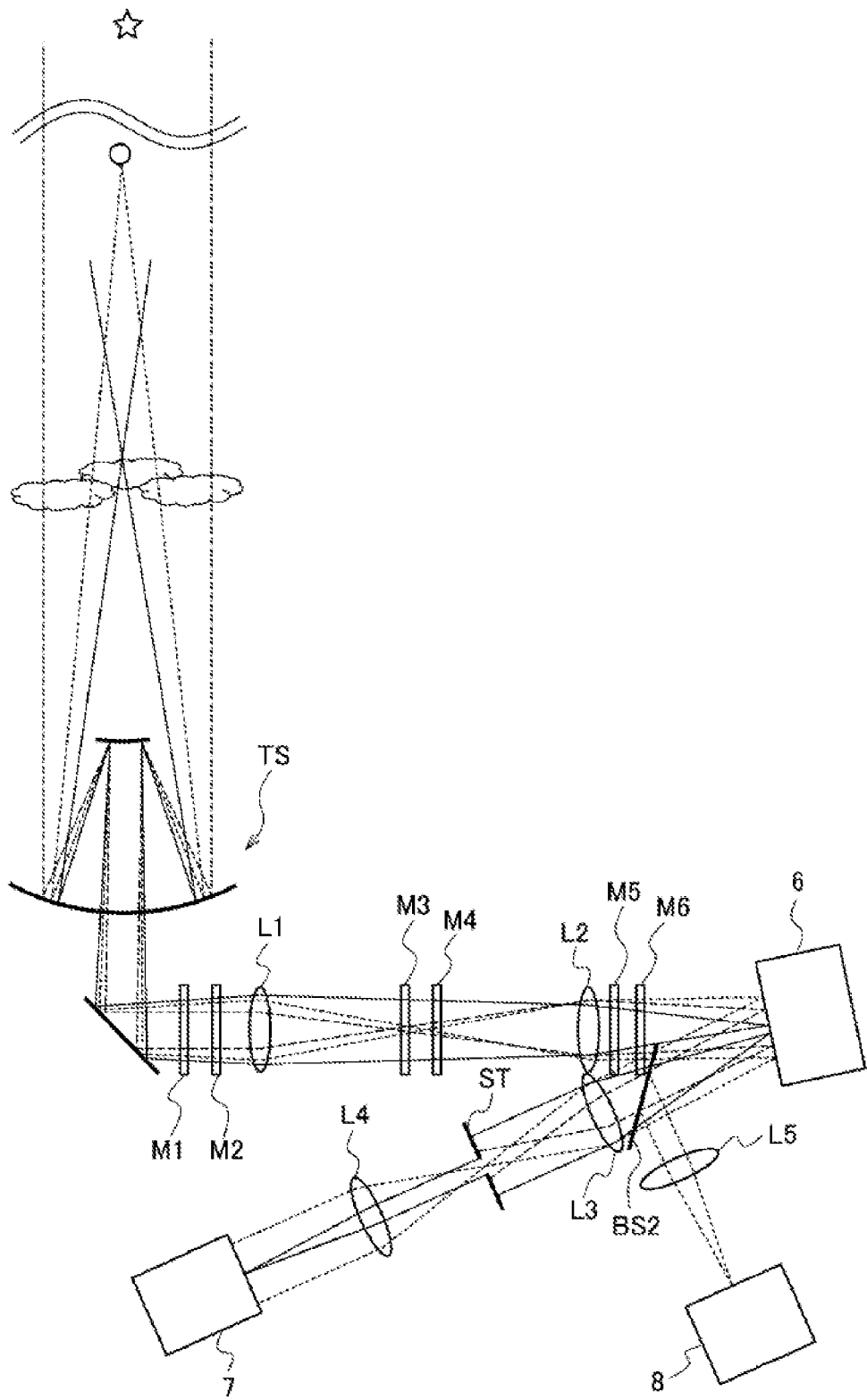

ADAPTIVE OPTICS SYSTEM AND OPTICAL DEVICE

CROSS REFERENCE TO RELATED APPLICATION

This application is a Continuation of copending U.S. application Ser. No. 15/023,281 filed Mar. 18, 2016, which is the National Phase under 35 U.S.C. § 371 of International Application No. PCT/JP2014/074837, filed on Sep. 19, 2014, which claims the benefit under 35 U.S.C. § 119(a) to Patent Application No. 2013-195943, filed in Japan on Sep. 20, 2013, all of which are hereby expressly incorporated by reference into the present application.

TECHNICAL FIELD

The present invention relates to an adaptive optics system and an optical device including the adaptive optics system, more specifically, to a technique for correcting aberration resulting from an observation target.

BACKGROUND

Microscopic devices are generally used to observe biological specimens such as cells. When the observation target is a cell, however, there arises a problem that the cell surface or a specific subcellular organelle forms a fluctuation (distortion) generating layer to cause wave aberration. In addition, when the observation target is a biological tissue or organ, the tissue surface or a specific tissue layer forms a main distortion generating layer. Accordingly, various studies have been conventionally conducted for microscopic devices for use in observation of biological specimens to correct wave aberration resulting from the observation target and obtain high-quality microscopic images (refer to Patent Documents 1 to 4).

For example, Patent Document 1 proposes a technique for correcting aberration by which a rear pupil in an optical system is segmented and each segment is controlled by a wavefront modulation device. Patent Document 2 proposes a method for wavefront correction using an optical writing-type liquid crystal spatial phase modulation element. At a wavefront correction imaging device described in Patent Document 2, light from an object to be measured is passed through a disturbance medium in the space between the object and an observation surface and entered into a phase modulation surface of the liquid crystal spatial phase modulation element, and an interference pattern reflecting a phase distribution of the disturbance medium is obtained from reference light reflected on the phase modulation surface, and the interference pattern is applied to a writing surface of the liquid crystal spatial phase modulation element to form a phase modulation surface in such a manner as to cancel out the phase distribution of the disturbance medium, and then light to be measured having passed from the object through the disturbance medium and entered into the phase modulation surface and reflected on the same is observed.

Further, in the field of ophthalmic equipment, there are proposed adaptive optics systems that correct wavefront aberration detected by a wavefront sensor with the use of a wavefront corrector such as a deformable mirror or a spatial light modulator as described in Patent Documents 3 and 4.

CITATION LIST

Patent Literatures

[Patent Document 1] JP-T No. 2012-533069
[Patent Document 2] JP-A No. 2002-040368
[Patent Document 3] JP-T No. 2005-501587
[Patent Document 4] JP-A No. 2011-239884

SUMMARY OF INVENTION

Technical Problem

However, according to the conventional adaptive optics systems described above, it is difficult to correct wavefront phase aberration with high accuracy when the observation target and the fluctuation layer are close to each other or when the observation target is minute. In particular, biological tissues including cells have large and dense fluctuations in many cases. As a result, the correction control is likely to become unstable and the range of effective correction is narrow.

It has been noted that the adaptive optics system described in Patent Document 4 is complicated in device configuration. To reduce the device size, it is proposed to use a special optical system using aspheric lenses or special components such as a light-driven modulator. In that case, however, the adaptive optics system loses simplicity and flexibility and becomes deteriorated in productivity as practical equipment and extensibility as an experimental device.

A major object of the present invention is to provide an adaptive optics system and an optical device that allow correction of wavefront phase aberration with higher accuracy than before and have a wider correction range than the conventional ones regardless of the distance between the observation target and the fluctuation layer and the size of the observation target.

Solution to Problem

An adaptive optics system according to the present invention includes: a wavefront phase modulator that makes aberration correction to incident light and emits the corrected light; and an imaging-conjugated position adjustment mechanism that adjusts freely within a specimen the position of a surface imaging-conjugated with a fluctuation correction surface formed by the wavefront phase modulator, and the imaging-conjugated position adjustment mechanism adjusts the fluctuation correction surface to be imaging-conjugated with a fluctuation layer existing in the specimen.

In the adaptive optics system, as the imaging-conjugated position adjustment mechanism, an objective lens, and a first lens and a second lens constituting relay lenses may be arranged sequentially from the specimen side between the wavefront phase modulator and the specimen.

In this configuration, the position of the surface imaging-conjugated with the fluctuation correction surface in the specimen can be adjusted by changing the optical distance between the objective lens and the first lens.

In that case, a turn-back optical system including at least one mirror may be arranged between the objective lens and the first lens, for example, so that the turn-back optical system can be moved in a direction parallel to an optical axis to change the optical distance between the objective lens and the first lens.

In addition to the foregoing configuration or aside from the foregoing configuration, the position of the surface imaging-conjugated with the fluctuation correction surface in the specimen may be adjusted by changing the optical distance between the second lens and the wavefront phase modulator.

In that case, a turn-back optical system including at least one mirror may be arranged between the second lens and the wavefront phase modulator, for example, so that the turn-back optical system can be moved in the direction parallel to an optical axis to change the optical distance between the second lens and the wavefront phase modulator.

Alternatively, a turn-back optical system including at least one mirror may be arranged between the first lens and the second lens, so that the turn-back optical system can be moved in the direction parallel to an optical axis to change the optical distance between the first lens and the second lens.

The turn-back optical system may be placed on a slide stage movable in the direction parallel to the optical axis.

Alternatively, the objective lens may be movable integrally with a stage on which the specimen is placed and the first and second lenses may be movable.

The adaptive optics system of the present invention may further have a wavefront sensor that detects a wavefront residual component included in the light corrected by the wavefront phase modulator and a first control unit that controls the wavefront modulator based on the results of detection by the wavefront sensor, and the first control unit may adjust the wavefront modulator such that the fluctuation correction surface is phase-conjugated with the fluctuation layer existing in the specimen.

In that case, the first control unit can adjust the wavefront phase modulator such that the wavefront phase of incident light on the wavefront sensor takes a set value.

At least one of the first lens and the second lens may be displaced to correct a wavefront tilt and/or a wavefront curvature.

A plurality of wavefront phase modulators may be arranged to be imaging-conjugated onto different positions of the specimen in a depth direction between the specimen and the wavefront sensor.

A field stop may be arranged on or around a focal plane between the wavefront phase modulator and the wavefront sensor.

In that case, the field stop can be moved according to the position of a reference object existing in the specimen.

The wavefront sensor may be changed in position according to the position of the reference object existing in the specimen.

A plurality of wavefront sensors may be provided.

The wavefront sensor may be arranged such that the alignment of the elements is rotated 45° relative to the wavefront phase modulator.

Alternatively, the wavefront sensors may be of a phase contrast type.

An optical device according to the present invention includes the adaptive optics system described above.

The optical device of the present invention has an imaging element that acquires an image of an observation target in the specimen and an image of the fluctuation correction surface, and adjusts the focuses of the images formed on the imaging element to acquire one of the image of the observation target and the image of the fluctuation correction surface.

Alternatively, the optical device may have a first imaging element that takes an image of an observation target in the specimen, a second imaging element that takes an image of the fluctuation correction surface, and one or more beam splitters that branch part of the light from the specimen toward the first imaging element and the second imaging element, and the optical device may be configured to acquire independently the image of the observation target and the image of the fluctuation correction surface.

In that case, the optical device may have a second control unit that controls position adjustment of the surface to be imaging-conjugated with the fluctuation correction surface by the imaging-conjugated position adjustment mechanism based on the image of the fluctuation correction surface.

The optical device may acquire a group of tomographic images of the specimen while shifting the focus in the depth direction at specific intervals.

The optical device may continuously acquire the image of the observation target in the specimen at certain time intervals.

The optical device of the present invention is a microscopic device, a telescope, a laser measurement device, a laser injection device, a camera, or a medical testing device, for example.

The microscopic device is any of a fluorescence microscope, a differential interference microscope, a phase-contrast microscope, a super-resolution microscope, a scanning microscope, a multiphoton microscope, and a laser injection microscope, for example.

Advantageous Effects of Invention

According to the present invention, the fluctuation correction surface and the fluctuation layer are imaging-conjugated with each other in the adaptive optics system, and it is thus possible to correct wavefront phase aberration with high accuracy in a wide range even when the observation target and the fluctuation layer are close to each other or when the observation target is minute.

BRIEF DESCRIPTION OF DRAWINGS

FIG. 1 is a schematic diagram illustrating a configuration of a microscopic device in a first embodiment of the present invention;

FIG. 2 is a schematic diagram illustrating a configuration example of a specimen 1;

FIG. 3 is a diagram illustrating a configuration of a scaling relay optical system holding both imaging relationship in a 4f optical system and the planarity of wavefront phase;

FIG. 4 is a diagram illustrating a configuration example of an adaptive optics system in the microscopic device illustrated in FIG. 1;

FIG. 5A illustrates the state before adjustment and FIG. 5B illustrates the state after adjustment;

FIG. 7 is a diagram illustrating a method for an image focus in the microscopic device via the adaptive optics system;

FIG. 8 is a diagram illustrating a configuration example of an adaptive optics system in a microscopic device as a first modification example of the first embodiment of the present invention;

FIG. 9A illustrates the state before adjustment and FIG. 9B illustrates the state after adjustment;

FIG. 10 is a diagram illustrating a configuration example of an adaptive optics system in a microscopic device as a second modification example of the first embodiment of the present invention;

FIG. 11 is a diagram showing a method for changing independently a light path length $lc_2$ by adjustment of a light path length $lr$;

FIG. 12 is a diagram showing a method for adjusting light path lengths in a microscopic device as a third modification example of the first embodiment of the present invention;

FIG. 13 is a diagram illustrating a specific configuration example of implementing the method for adjusting a light path length shown in FIG. 12;

FIG. 14 is a diagram illustrating a specific configuration example of implementing the method for adjusting a light path length shown in FIG. 12;

FIG. 15 is a diagram illustrating a specific configuration example of implementing the method for adjusting a light path length shown in FIG. 12;

FIG. 16 is a diagram illustrating a specific configuration example of implementing the method for adjusting a light path length shown in FIG. 12;

FIG. 17 is a diagram illustrating a specific configuration example of implementing the method for adjusting a light path length shown in FIG. 12;

FIG. 18 is a diagram illustrating an imaging-conjugated position adjustment mechanism (with one relay lens) for fluctuation correction surface in a microscopic device as a fourth modification example of the first embodiment of the present invention;

FIG. 19 is a diagram illustrating another imaging-conjugated position adjustment mechanism (with two relay lenses) for fluctuation correction surface in the microscopic device as the fourth modification example of the first embodiment of the present invention;

FIG. 20 is a diagram illustrating a specific configuration example of the imaging-conjugated position adjustment mechanism for the fluctuation correction surface illustrated in FIG. 18;

FIG. 22 is a diagram illustrating a configuration example of an imaging-conjugated position adjustment mechanism for fluctuation correction surface in a microscopic device as a sixth modification example of the first embodiment of the present invention;

FIG. 23 is a diagram illustrating another configuration example of an imaging-conjugated position adjustment mechanism for fluctuation correction surface in the microscopic device as the sixth modification example of the first embodiment of the present invention;

FIG. 24 is a diagram illustrating an overview of a microscopic device as a seventh modification example of the first embodiment of the present invention;

FIG. 25 is a diagram illustrating a configuration of the adaptive optics system illustrated in FIG. 24 using a plurality of wavefront sensors;

FIG. 26 is a diagram illustrating a method for correcting a wavefront tilt component with displacement of lenses in a relay optical system;

FIG. 27 is a diagram illustrating a method for correcting a wavefront curvature component with displacement of the lenses in the relay optical system;

FIG. 28 is a diagram illustrating a configuration example of an adaptive optics system in a microscopic device as a tenth modification example of the first embodiment of the present invention;

FIG. 29 is a schematic diagram illustrating the element layout of a wavefront phase modulator and a wavefront shape in a waffle mode;

FIG. 30A illustrates a normal arrangement and FIG. 30B illustrates a 45° rotated arrangement;

FIG. 31A illustrates a normal arrangement and FIG. 31B illustrates a 45° rotated arrangement;

FIG. 32A illustrates the state before application and FIG. 32B illustrates the state after application;

FIG. 33 is a schematic diagram illustrating a configuration of a laser injection microscope using a laser injection device according to a third embodiment of the present invention;

FIG. 34 is a schematic diagram illustrating a configuration of a phase-contrast microscopic device according to a fourth embodiment of the present invention;

FIG. 35 is a schematic diagram illustrating a configuration of a differential interference microscopic device according to a fifth embodiment of the present invention;

FIG. 36 is a schematic diagram illustrating a configuration of a confocal scanning microscopic device according to a sixth embodiment of the present invention;

FIG. 37 is a schematic diagram illustrating a configuration of a multiphoton excitation microscope according to a seventh embodiment of the present invention;

FIG. 38 is a schematic diagram illustrating a configuration of a telescopic device according to a ninth embodiment of the present invention;

DESCRIPTION OF EMBODIMENTS

Figure 5A:
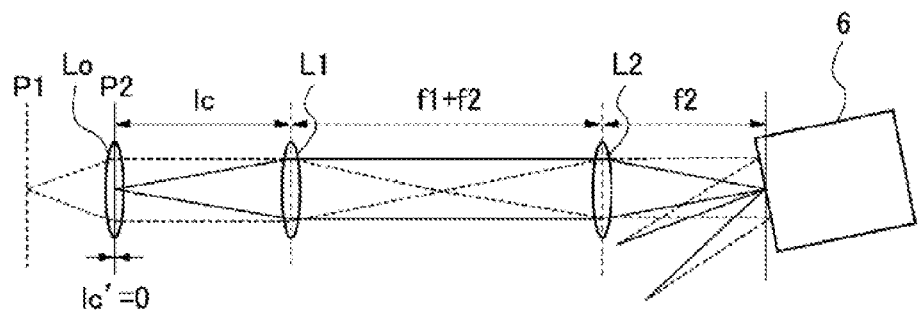
FIGS. 5A and 5B are schematic diagrams illustrating operations of an imaging-conjugated position adjustment mechanism for fluctuation correction surface.

Description of embodiments of the present invention will be described below in detail with reference to the accompanying drawings. However, the present invention is not limited to the embodiments described below.

First Embodiment

First, a microscopic device according to a first embodiment of the present invention will be described, taking a fluorescence microscope as an example. FIG. 1 is a schematic diagram illustrating a configuration of the microscopic device of the embodiment, and FIG. 2 is a schematic diagram illustrating a configuration example of a specimen 1.

[Entire Configuration]

The microscopic device of the embodiment includes an adaptive optics system so that the position of an imaging-conjugated surface relative to a fluctuation correction surface of the adaptive optics system is freely adjustable. Specifically, as shown in FIG. 1, the microscopic device of the embodiment includes a light source 3, a wavefront phase modulator 6, a wavefront sensor 7, an imaging camera 8, a pupil camera 9, a computer 10, and others.

In the microscopic device, an objective lens Lo, a beam splitter BS1, mirrors M1 and M2, a relay lens L1, mirrors M3 and M4, and a relay lens L2 are arranged in this order between the specimen 1 and the wavefront phase modulator 6. In addition, a beam splitter BS2, a filter F3, a relay lens L3, a field stop ST, a relay lens L4, and a beam splitter BS3 are arranged in this order between the wavefront phase modulator 6 and the wavefront sensor 7.

The microscopic device of the embodiment is configured such that excitation light emitted from the light source 3 is applied to the specimen 1 via a filter F1, the beam splitter BS1, and the objective lens Lo. In addition, the microscopic device of the embodiment is configured such that the light reflected on the beam splitter BS2 enters into the imaging camera 8 via the filter F2 and the lens L5, and the light reflected on the beam splitter BS3 enters into the pupil camera 9 via the lens L6. Further, the specimen 1 and the mirrors M1 to M4 are arranged on a specimen stage 2 and slide stages 4 and 5, respectively, and are adjustable in position by moving these stages 2, 4, and 5.

[Specimen 1]

The specimen 1 observed by the microscopic device of the embodiment is a biological specimen such as an animal tissue, a plant tissue, or a cultured cell that is placed on a slide glass (not illustrated) and sealed with a cover glass 103 as illustrated in FIG. 2, for example. In the case of the specimen 1 illustrated in FIG. 2, excitation light emitted from the light source 3 enters into the specimen 1 via an objective lens 104 and the cover glass 103.

The specimen 1 includes an observation target 100, a reference object 101, and fluctuation elements. The "observation target" here refers to a portion (matter) that exists within the specimen 1 and is to be observed from its optical image, such as a biological tissue, a cell, an intracellular structure, or a molecule of fluorescent protein, for example. The "reference object" refers to an object for use in measurement of wavefront fluctuations at the time of control of the adaptive optics system, and may be artificial or natural matter, such as a fluorescent bead, a tissue, a specific site in a cell, or a molecule of fluorescent protein, for example. The observation target 100 may be used as the reference object 101. In that case, light from the observation target 100 is introduced into the adaptive optics system for wavefront correction.

The "fluctuation elements" refer to factors that cause phase disturbance to light from the observation target 100 or the reference object 101 at the time of passage and fluctuates the transmitted wavefront, such as unevenness in refractive index inside the specimen 1, asperities in the surface of the specimen 1, and the like. The fluctuations in the transmitted wavefront constitute a cause of image deterioration. There is a fluctuation layer 102 including a large number of fluctuation elements resulting in error such as phase aberration between the observation target 100 and the objective lens 104. Specific examples of the fluctuation layer 102 are the surface of a biological tissue or organ, the surface of a cell (a boundary with water or culture medium), and an intracellular structure and tissue significantly different in refractive index from the circumference, such as a cell wall of a plant cell and a chloroplast, for example.

[Specimen Stage 2]

The specimen stage 2 displaces the position of the specimen 1 along three axes of x, y, and z (three directions) relative to the objective lens. At the microscopic device of the embodiment, the specimen stage 2 is displaced in the z-axis direction to adjust focus, and the specimen stage 2 is displaced in the x- and y-axis directions to adjust the position of the observation target 100 within a field of view.

[Light Source 3]

The light source 3 is intended to apply excitation light for generation of fluorescent light to the specimen 1, and may be a halogen lamp, a tungsten lamp, a mercury lamp, an LED (light emitting diode), a solid state plasma light source, various lasers, or the like.

[Filter F1]

The light source filter F1 lets through only the light with wavelengths necessary for excitation of fluorescent light out of the excitation light emitted from the light source 3, and shuts off the light with unnecessary wavelengths.

[Beam Splitter BS1]

The beam splitter BS1 is a fluorescence excitation mirror that enters the excitation light emitted from the light source 3 into the specimen 1 via the objective lens 104 (objective lens Lo) when fluorescent light is to be excited in the observation target 100 and/or the reference object 101 of the specimen 1. For example, in the configuration illustrated in FIG. 1, the beam splitter BS1 reflects the excitation light with short wavelengths, and lets through the fluorescent light with long wavelengths emitted from the observation target 100 or the reference object 101 and guides the same to the observation-side optical system (mirror M1). The beam splitter BS1 may be a half mirror such as a dichroic mirror, for example, to discriminate reflection and transmission depending on light wavelengths.

[Objective Lens Lo]

The objective lens Lo may be an objective lens for infinity focus optical system, for example. The objective lens for infinity focus optical system converts divergent light from the observation target 100 placed within an operating distance of the objective lens 104 into parallel light beams as illustrated in FIG. 2, and is designed to have smaller optical aberration in that case.

[Conjugate Slide]

The two mirrors M1 and M2 are arranged at a 90° angle on a conjugate slide stage 4. The light emitted from the specimen 1 is folded back by the mirrors M1 and M2 in the direction parallel to the incident direction. The conjugate slide stage 4 is movable along the optical axes of the incident light and the outgoing light, thereby achieving variable adjustment of a light path length from the relay lens L1 to the objective lens Lo. At the microscopic device of the embodiment, the light path length is changed in this manner to adjust the imaging-conjugated position relative to the fluctuation correction surface in the specimen 1. The "light path length" here refers to the length of a space along the light beam, and indicates the length of the optical axis of the light flux or the optical distance between the optical elements in the microscopic device of the embodiment.

[Focus Slide]

The two mirrors M3 and M4 are arranged at a 90° angle on the focus slide stage 5. The light reflected on the mirror M2 and entered into the mirrors M3 and M4 via the relay lens L1 is folded back by the mirrors M3 and M4 in the direction parallel to the incident direction. The focus slide stage 5 is also movable along the optical axes of the incident light and the outgoing light, thereby achieving variable adjustment of a light path length. To adjust the focus slide stage 5, the wavefront phase modulator 6 to relay lens L2 are arranged in proper positions, the light path length from the relay lens L1 to the relay lens L2 is adjusted, and the focus slide stage 5 is moved such that the image focus becomes correct.

[Relay Lenses L1 and L2]

The relay lenses L1 and L2 constitute a relay optical system using optical elements with positive refractive power such as convex lenses. The major functions of the relay lenses L1 and L2 are as follows:

(1) Determining the image magnification ratio in conjunction with the objective lens Lo.

(2) When projecting the light beam from the pupil opening of the objective lens Lo onto the wavefront phase modulator 6, adjusting the light flux to match the opening of the wavefront phase modulator 6.

(3) Making imaging conjugate between the incident surface and the outgoing surface, and preventing unnecessary elements such as excessive tilt or curvature from increasing in wavefront phase between the incident surface and the outgoing surface.

To realize the functions (1) and (2), a scaling optical system may be used as the relay optical system. In addition, the 4f optical system is known as a relay optical system realizing the function (3). Accordingly, the microscopic device of the embodiment also supports the case where the focal distances of the two relay lenses L1 and L2 are different based on the configuration of the 4f optical system to achieve the image scaling ratio. Specifically, the scaling relay lens system as illustrated in FIG. 3 is formed by the relay lenses L1 and L2, a lens 110 with a refractive power of 1/f1, and a lens 111 with a refractive power of 1/f2.

In this case, first, as illustrated by dotted lines in FIG. 3, points on an incident surface $P_{in}$ and an outgoing surface $P_{out}$ are in the imaging-conjugate relationship. Meanwhile, as illustrated by solid lines in FIG. 3, parallel light beams on the incident surface $P_{in}$ are kept in parallel even on the outgoing surface $P_{out}$. Wavefront phase vertical to these light beams hold planarity and have no increase or decrease due to tilt or curvature. When the lenses 110 and 111 are equal in refractive power as a similar property for holding the wavefront phase in an optical system, the optical system is known as 4f Fourier transform optical system.

[Wavefront Phase Modulator 6]

The wavefront phase modulator 6 is a device that makes dynamic aberration correction to varying phase error in incident light and emits the corrected light. In the adaptive optics system of the microscopic device of the embodiment, the wavefront phase modulator 6 makes phase correction. In this case, the element surface of the wavefront phase modulator 6 serves as a fluctuation correction surface in the adaptive optics system.

For example, a deformable mirror formed by a micromachine driving a thin-film mirror by electrostatic force may be used as the wavefront phase modulator 6. In that case, the deformable mirror is connected to a control calculator (computer 10) via a digital-analog converter such that drive voltage is applied to the elements of a 12×12 square array, for example, based on a control signal output from a control port of the calculator.

When the deformable mirror applies the drive voltage to each of the elements to drive individually the plurality of electrostatic elements, the thin-film mirror surface for reflection of the incident light beam is pushed and pulled, and the shape of the mirror surface deforms. This displaces a light phase distribution as needed, and allows dynamic aberration correction to the varying phase error. Instead of the deformable mirror described above, a spatial light phase modulator using liquid crystal or the like can be used as the wavefront phase modulator 6.

[Beam Splitter BS2]

The beam splitter BS2 is a kind of half mirror that is highly efficient and flattened to prevent deterioration in performance of the optical system. To split light by wavelength to improve the sensitivity, a dichroic mirror may be used as the beam splitter BS2. For improvement of light efficiency, instead of branching by the half mirror, a non-light permeable reflection mirror may be brought in and out to switch between the light paths of reflection and transmission.

The light beams split by the beam splitter BS2 are branched into the optical system for the imaging camera 8 and the optical system for the wavefront sensor 7. In the following descriptions, the light path branched by the beam splitter BS2 and having the imaging camera 8 will be referred to as "imaging observation light path," and the light path branched by the beam splitter BS2 and having the wavefront sensor 7 as "wavefront measurement light path." The arrangements of the "imaging observation light path" and the "wavefront measurement light path" may be exchanged. Even in that case, the same functions and effects can be obtained.

[Filter F2]

The filter F2 is a fluorescent light filter that lets through only the light with wavelengths necessary for observation from the observation target 100 out of the fluorescent light emitted from the specimen 1, and shuts off the unnecessary components.

[Lens L5]

The lens L5 is an image-forming lens that forms an image of the observation target 100 within the specimen 1 on the imaging surface of the imaging camera 8.

[Imaging Camera 8]

The imaging camera 8 acquires an image of the observation target 100 and may be a CCD (charge-coupled device) camera or the like, for example. The image on the imaging surface of the imaging camera 8 is converted into an electric signal and output to an image storage unit 11 of the computer 10.

[Filter F3]

The filter F3 is a fluorescent light filter that lets through only the fluorescent components from the reference object 101 out of the light emitted from the specimen 1, and shuts off the unnecessary components.

[Relay Lenses L3 and L4]

The relay lenses L3 and L4 are lenses with positive refractive power such as convex lenses that form an imaging-conjugate between the wavefront phase modulator 6 as an incident surface and the opening of the wavefront sensor 7 as an outgoing surface. The relay lenses L3 and L4 are preferably arranged in the scaling relay optical system based on the 4f optical system as illustrated in FIG. 3, such that there is no difference in wavefront curvature between the outgoing light from the wavefront phase modulator 6 and the incident light on the wavefront sensor 7.

[Field Stop ST]

The field stop ST lets through only the light passing through the opening hole out of the light emitted from the reference object 101, and shuts off other unnecessary light. The size of the opening hole of the field stop ST is adjustable by a throttle mechanism. Even for unfocused light, the field stop ST has the effect of reducing the amount of transmitted light by a mismatch between the opening hole and the beam light collection. The field stop ST is arranged on or around a focal plane between the relay lenses L3 and L4. When the scaling relay optical system illustrated in FIG. 3 is used for the relay lenses L3 and L4, for example, the field stop ST is preferably arranged at the position corresponding to a Fourier diffractive plane DP or the position on the front or back side of the same.

[Beam Splitter BS3]

The beam splitter BS3 is a kind of half mirror that branches part of the light entered into the wavefront measurement light path toward the pupil camera 9 in front of the wavefront sensor 7.

[Wavefront Sensor 7]

The wavefront sensor 7 detects a wavefront residual component not corrected by the wavefront phase modulator 6 but left on the light wavefront that has been emitted from the reference object 101 in the specimen 1 and has passed through the fluctuation layer 102 and received fluctuations. There is no particular limitation on the type of the wavefront sensor 7. For example, the wavefront sensor 7 may be a Shack-Hartmann type. The Shack-Hartmann-type wavefront sensor has a lenslet array at the incident opening portion, and further includes a light-receiving CCD camera to detect the tilt of an incident wavefront by lateral displacements of a light-collection spot of each small opening generated at the back side of the lenslet array.

The adaptive optics system in the microscopic device of the embodiment can control the phase tilt of incident light on the wavefront sensor 7 to take an arbitrary set value, specifically, an ideal value, zero, for example. When the wavefront sensor 7 is a Shack-Hartmann-type wavefront sensor, the opening surface of the lenslet array constitutes the wavefront measurement surface in the adaptive optics system.

[Computer 10]

The computer 10 is provided with the image storage unit 11 that stores images acquired by the imaging camera 8 and the pupil camera 9 and an adaptive optical control unit 12 that controls the wavefront phase modulator 6 and others based on a signal from the wavefront sensor 7. The adaptive optical control unit 12 converts a measurement signal of wavefront residual output from the wavefront sensor 7 into a control voltage correction value of the wavefront phase modulator 6 by an adaptive optical control program, and outputs the resultant value to the wavefront phase modulator 6 to compensate for a wavefront phase error on the wavefront correction surface.

The microscopic device of the embodiment performs a closed-loop control among the incident wavefront, the wavefront sensor 7, the wavefront phase modulator 6, the adaptive optical control unit 12 of the computer 10 to provide negative feedback to the incident wavefront fluctuations, so that the phase distortion on the light wavefront converges asymptotically on an ideal value, zero, for example.

[Lens L6]

The lens L6 is an image-forming lens for the pupil camera 9, which forms on the imaging surface of the pupil camera 9 a mirror image 13 of the fluctuation measurement surface of the wavefront sensor 7 from the light branched by the beam splitter BS3 as illustrated in FIG. 1. The lens L6 may be made changeable in position to form an image of the reference object 101 on the imaging surface of the pupil camera 9 by adjusting the focal distance of the beam splitter BS3 at infinity (moving to the position of a lens L6').

[Pupil Camera 9]

The pupil camera 9 acquires an image of the fluctuation measurement surface of the wavefront sensor 7 and an image of the reference object 101. The pupil camera 9 may be a CMOS (complementary metal oxide semiconductor) camera or the like, for example. The image generated on the imaging surface of the pupil camera 9 is converted into an electrical signal and output to the image storage unit 11 of the computer 10.

[Operations]

Next, operations of the microscopic device of the embodiment will be described taking the observation of the specimen 1 illustrated in FIG. 2 as an example.

<Outline of Microscopic Operations>

In the microscopic device of the embodiment, in advance, the deformable mirror is set flat and the optical components such as lenses and cameras are adjusted such that a general microscopic image can be obtained without wavefront correction. Then, the specimen 1 is placed on the specimen stage 2, the specimen stage 2 is moved while observing the observation target 100 by the imaging camera 8, and the focus and the lateral position are adjusted such that the image becomes optimum. The images shot by the imaging camera 8 are stored in the computer 10. The images are read from the computer 10 as necessary and subjected to image processing and analysis.

<Outline of Image Correction by the Adaptive Optics>

To perform image correction by adaptive optics, first, the size and position of the field stop ST are adjusted and the specimen stage 2 is moved to adjust the position of the specimen 1 while the image of the reference object 101 acquired by the pupil camera 9 is checked so that light enters appropriately into the wavefront sensor 7. The adjustment of the field stop ST and the positioning of the specimen 1 can be automatically performed by a position adjustment control unit (not illustrated) controlling the individual adjustment mechanisms.

In that state, the adaptive optical control unit 12 (adaptive optical control program) of the computer 10 is operated to acquire data on wavefront phase distortion at the wavefront sensor 7, provide negative feedback of the correction value to the wavefront phase modulator 6 to update the control value of the mirror surface shape, and repeat these operations. When the feedback control is appropriately conducted, the wavefront residual detected by the wavefront sensor 7 converges on an ideal value, zero, for example, and the resolution of the image on the imaging camera 8 is improved to obtain a clear image.

<Position Adjustment of the Imaging-Conjugated Surface Relative to the Fluctuation Correction Surface>

Figure 5B:
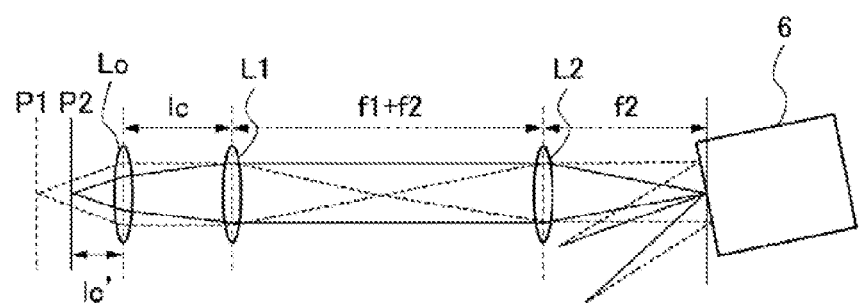

FIG. 4 is a diagram illustrating a configuration example of the adaptive optics system in the microscopic device illustrated in FIG. 1. FIGS. 5A and 5B includes schematic diagrams illustrating operations of an imaging-conjugated position adjustment mechanism for the fluctuation correction surface. In FIGS. 4 and 5, dotted lines show light from the observation target or the reference object, solid lines show light converging on the fluctuation correction surface, and reference signs fo and f1 to f4 show the focal distances of the objective lens Lo and the lenses L1 to L4, respectively. In FIGS. 5A and 5B, reference sign P1 shows the position of the observation target or the reference object, and P2 shows the position of the imaging-conjugated surface relative to the fluctuation correction surface. FIG. 4 illustrates only the elements related to the position adjustment of the imaging-conjugated surface relative to the fluctuation correction surface in an equivalent manner, but does not illustrate the elements not directly related to the position adjustment.

First, descriptions will be given as to a method for adjusting the imaging-conjugated position relative to the fluctuation correction surface by changing the optical distance between the objective lens Lo and the relay lens L1. As shown by the solid lines in FIG. 4, when the light beam entering into the fluctuation correction surface (element surface) of the wavefront phase modulator 6 is reversed, the light beam converges in the specimen 1, and an image of the fluctuation correction surface in the adaptive optics system is formed at a distance lc' from the objective lens Lo as an imaging-conjugated surface.

As illustrated in FIG. 5A, before the position adjustment of the imaging-conjugated surface relative to the fluctuation correction surface, the opening pupil of the objective lens Lo and the fluctuation correction surface P2 are imaging-conjugated with each other, and thus lc'=0. The distance lc' between the image-forming plane P2 of the fluctuation correction surface and the objective lens Lo can be changed by adjusting a light path length lc between the objective lens Lo and the relay lens L1. Taking advantage of this change, the position of the image-forming plane P2 of the fluctuation correction surface in the adaptive optics system can be imaging-conjugated with the position of the fluctuation layer 102 in the specimen 1.

As illustrated in FIG. 5B, after the position adjustment, the distance lc' between the image-forming plane P2 of the fluctuation correction surface and the objective lens Lo is increased and the image-forming position of the fluctuation correction surface is moved. However, the light beam shown by the dotted lines emitted from the observation target or the reference object remains unchanged between before and after the adjustment. Specifically, by adjusting the image-forming position of the fluctuation correction surface, the light path length lc between the objective lens Lo and the relay lens L1 is changed but the light path length (=f1+f2) between the relay lens L1 and the relay lens L2 and the light path length (=f2) between the relay lens L2 and the wavefront phase modulator 6 remain unchanged to fix the focus of the image from the observation target or the reference object.

The adjustment of the light path length lc can also be made by moving the position of the objective lens Lo together with the specimen stage 2 or arranging the turnback optical system composed of the mirrors M2 and M3 on the conjugate slide stage 4 and moving the same in the direction parallel to the optical axis. In that case, in the microscope, the conjugate slide stage 4 is operated to adjust the position of the imaging-conjugated surface relative to the fluctuation correction surface to the fluctuation layer 102 of the specimen 1 while checking the focus of the image on the fluctuation measurement surface acquired by the pupil camera 9, changes in light and shade due to convergence and divergence of wavefront phase, and a wavefront signal from the wavefront sensor 7, such that the effectiveness of the adaptive optics system becomes favorable. The conjugate slide stage 4 can be automatically adjusted by controlling the imaging-conjugated position adjustment mechanism by a position adjustment control unit (not illustrated).

The image in the pupil camera 9 decreases in contrast resulting from the wavefront phase when the imaging-conjugated surface relative to the fluctuation correction surface and the fluctuation layer in the specimen become close to each other. Accordingly, taking advantage of this, the position of the imaging-conjugate in the specimen relative to the fluctuation correction surface may be adjusted to be optimum for the fluctuation layer. This adjustment can also be automatically made by the position adjustment control unit (not illustrated) controlling the imaging-conjugated position adjustment mechanism.

At this time, the light beams shown by the dotted lines from the observation target or the reference object in FIGS. 5A and 5B are parallel between the objective lens Lo and the relay lens L1, and therefore the adjustment made to the light path length lc has no influence on the focus of the observation target or the reference object both before and after the adjustment. Specifically, even when the conjugate slide stage 4 is moved, the state of the light passing through the field stop ST and the state of the light incident on the wavefront sensor 7 illustrated in FIG. 4 are kept. In addition, when the reference object is placed at the same position as the observation target, the focus and the magnification ratio of the observation target on the imaging camera 8 and the pupil camera 9 are kept. Accordingly, it is possible to adjust freely the imaging-conjugated position in the specimen 1 relative to the fluctuation correction surface.

By the method for adjusting the optical distance (light path length lc) between the objective lens Lo and the relay lens L1 described above, it is possible to adjust readily the position of the imaging-conjugated surface in the specimen 1 relative to the fluctuation correction surface. In addition, as in the microscopic device of the present embodiment, by aligning the position of the imaging-conjugated surface relative to the fluctuation correction surface with the fluctuation layer 102, it is possible to improve the accuracy of wavefront correction and extend the viewing field of the correction region in the image of the observation target 100 acquired by the imaging camera 8.

<Focus Adjustment>

The adaptive optics operates to sharpen the image of the reference object 101. Accordingly, when the reference object 101 is distant from the observation target 100 as illustrated in FIG. 2, for example, there is need for a separate method for adjusting the focus on the observation target 100. The focus on the observation target 100 can be adjusted in such a manner as described below.

Figure 6A:
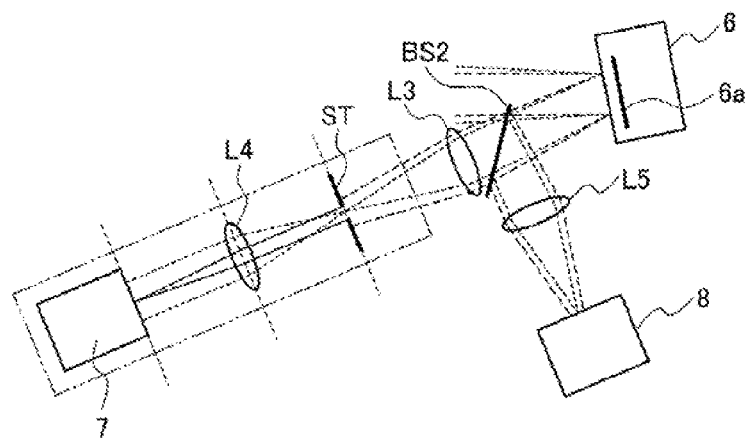
FIGS. 6A, 6B and 6C are diagram showing a method for adjusting an image focus by adjustment of the adaptive optics system.
Figure 6B:
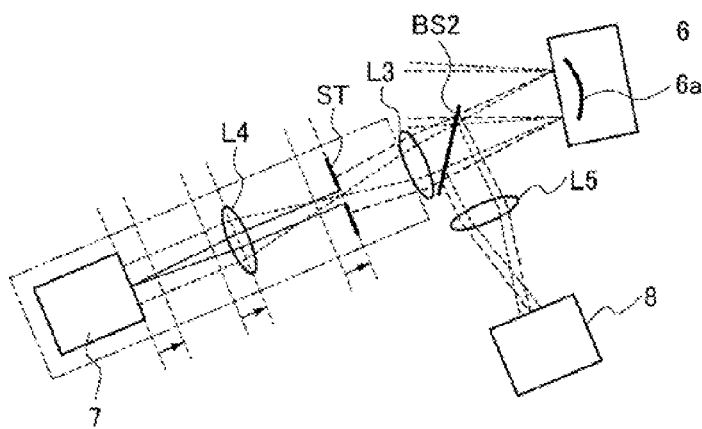
Figure 6C:
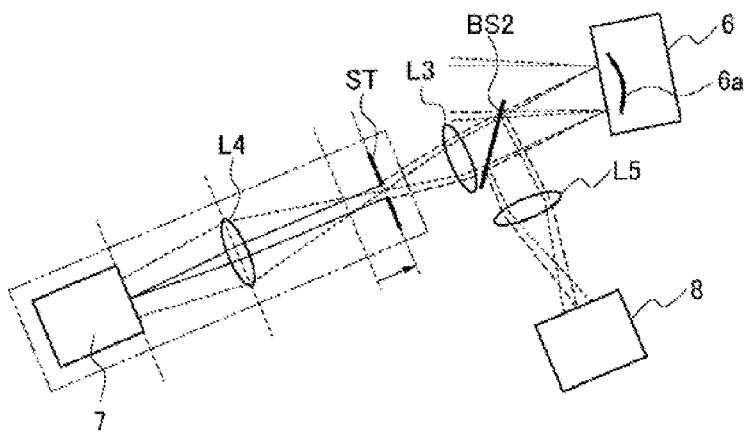

FIGS. 6A to 6C are diagrams illustrating a method for adjusting an image focus by the adjustment of the adaptive optics system. In FIGS. 6A to 6C, the same constituent elements as those in the microscopic device of the first embodiment described above are given the same reference signs as those in the first embodiment, and descriptions thereof will be omitted. FIGS. 6A to 6C illustrate only the elements related to the adjustment of the image focus, but do not illustrate the elements not directly related to the adjustment of the image focus.

<Focus Adjustment by the Imaging Camera 8>

Before the focus adjustment illustrated in FIG. 6A, the focus of the light from the observation target 100 shown by broken lines is shifted from the image-forming surface of the imaging camera 8. The focal position can be adjusted by changing the focus of the lens L5 or the position of the imaging camera 8. In this case, an aberration correction system may be incorporated into the lens L5 in conjunction with the focus adjustment.

<Focus Adjustment by Movement of the Wavefront Sensor 7 and the Relay Lens>

In the wavefront correction by the adaptive optics system, elements 6a of the wavefront phase modulator 6 are controlled such that the wavefront becomes planar on the incident surface of the wavefront sensor 7, that is, the light beams incident on the wavefront sensor 7 become parallel. Meanwhile, as illustrated in FIG. 6B, the field stop ST, the relay lens L4, and the wavefront sensor 7 are moved separately or integrally along the optical axis to displace the light incident on the wavefront sensor 7.

In this state, when the adaptive optics system is operated as usual to control the elements 6a of the wavefront phase modulator 6 such that the light incident on the wavefront sensor 7 is returned to be parallel, the light beams reflected on the wavefront phase modulator 6 can be diverged or converged. Then, taking advantage of the divergence or convergence of the light beams caused by the wavefront phase modulator 6 corresponding to the displacement of the field stop ST, the relay lens L4, and the wavefront sensor 7, it is possible to adjust arbitrarily the focus of the light beams in the imaging observation light path or the focus of the imaging camera 8.

<Infinity Focusing of the Imaging Observation Light Path>

By the same method, the outgoing light from the adaptive optics system can be subjected to infinity focusing. When the reference object 101 is distant from the observation target 100 as illustrated in FIG. 2, there occurs a difference in convergence or divergence due to the focus shift between the light beams shown by the broken lines from the observation target 100 and the light beams shown by the dotted lines from the reference object 101 as illustrated in FIG. 6A. Accordingly, when the field stop ST, the lens L5, and the wavefront sensor 7 are displaced along the optical axis as illustrated in FIG. 6B, the light beams shown by the dotted lines from the reference object can be entered as parallel light beams into the wavefront sensor 7, and the light beams shown by the broken lines from the observation target can be emitted as parallel light beams to the imaging observation light path.

<Adjustment of the Curvature by Providing an Offset to the Wavefront Sensor 7>

As shown in FIGS. 6A, 6B and 6C, instead of moving the positions of the lens L4 and the wavefront sensor 7 to absorb the convergence or divergence of the light (dotted lines) from the reference object, by providing an intentional deviation corresponding to the convergence or divergence of the light, that is, providing an offset to the signal from the wavefront sensor 7, it is possible to obtain the effect of focus adjustment. At that time, it is possible to shift the focus of the outgoing light, for example, by providing a deviation to the measurement value of the wavefront sensor 7, transferring the deviated value to the wavefront phase modulator 6 under negative feedback control, and adjusting the displacements of the elements 6a caused by the deviated value.

By using this method, the outgoing light to the imaging observation light path can be adjusted to an infinity focus. In this case, as necessary, the field stop ST is moved along the optical axis together with the movement of the focus.

<Focus Adjustment and Aberration Correction>

Aberration may occur when the distance from the objective lens Lo to the observation target is deviated from the designed value by the focus adjustment method described above, or when the state of light transmission through the relay lens changes. At that time, the aberration can be corrected by providing the image-forming lens L5 with an aberration correction mechanism in conjunction with the focus of the lens, adding an intentional deviation to the wavefront correction values of the wavefront sensor 7 and the wavefront phase modulator 6 to make fine adjustments for the aberration, or giving some contrivance to the relay lens, for example.

<Application to the Microscopic Device>

FIG. 7 is a diagram illustrating the correction of a focus shift between the light (dotted lines) from the reference object and the light (broken lines) from the observation target by the method illustrated in FIG. 6B. As illustrated in FIG. 7, the light (broken lines) from the observation target becomes parallel light beams, that is, an infinity focus optical system at the emission from the beam splitter BS2 to the imaging observation light path directed to the imaging camera 8. The light (broken lines) from the observation target is held parallel even from the relay lens L2 to the wavefront phase modulator 6. Accordingly, the displacement of the light path length at this section does not have influence on image properties such as the focus and the magnification ratio of the image of the observation target on the imaging camera 8.

As described above in detail, in the microscopic device of the embodiment, the position of the imaging-conjugated surface relative to the fluctuation correction surface is adjusted by the adaptive optics system to align with the fluctuation layer in the specimen, thereby retaining the maximum effectiveness of wavefront phase aberration correction. Accordingly, it is possible to improve the correction accuracy as compared to the conventional ones, and achieve high-accuracy correction even when the observation target and the fluctuation layer are close to each other or the observation target is minute. The microscopic device of the embodiment is high in stability even with large fluctuations and allows wide-range correction, as compared to the conventional systems.

Further, the microscopic device of the embodiment can reduce focus error at the time of incidence on the wavefront sensor. This makes it possible to suppress measurement error and enhance the effectiveness of the correction even in the case where the specimen has a lot of spatially fine structures like a biological specimen and high-spatial frequency components cannot be ignored. As a result, it is possible to improve the stability of wavefront correction and achieve stable operations.

The light emitted from the observation target and the reference object is not necessarily fluorescent light, and diverged light or reflected light from the observation target and the reference object may be detected by the imaging camera 8 and the pupil camera 9. Instead of the relay lens, a reflection mirror may be used. This configuration is effective for avoidance of color aberration in the case of using infrared rays.

In the microscopic device of the embodiment, the light path at the reflection side of the beam splitter BS2 and the light path at the transmission side of the beam splitter BS2 can be exchanged to perform the same operations. Specifically, in the microscopic device illustrated in FIG. 1, although the optical system including the wavefront sensor 7 is arranged in the straight transmission-side light path and the optical system including the imaging camera 8 and the image-forming lens L5 is arranged in the reflection-side light path, these optical systems may be exchanged such that the optical system including the wavefront sensor 7 is arranged in the reflection-side light path and the optical system including the imaging camera 8 and the image-forming lens L5 is arranged in the straight transmission-side light path.

First Modification Example of the First Embodiment

Figure 9A:
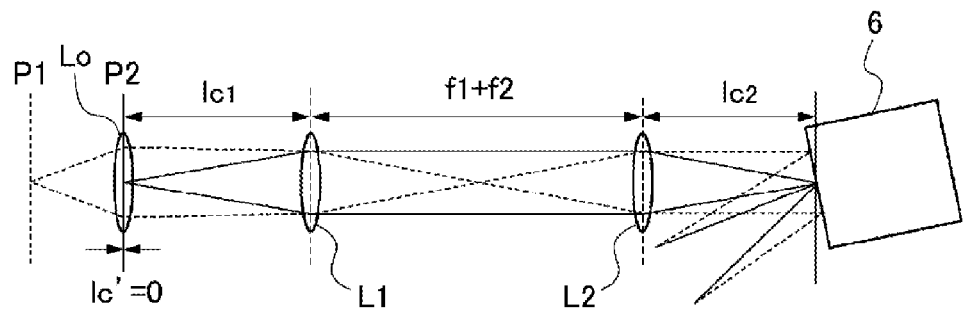
FIGS. 9A and 9B are schematic diagrams illustrating operations of an imaging-conjugated position adjustment mechanism for fluctuation correction surface in the adaptive optics system illustrated in FIG. 8.
Figure 9B:
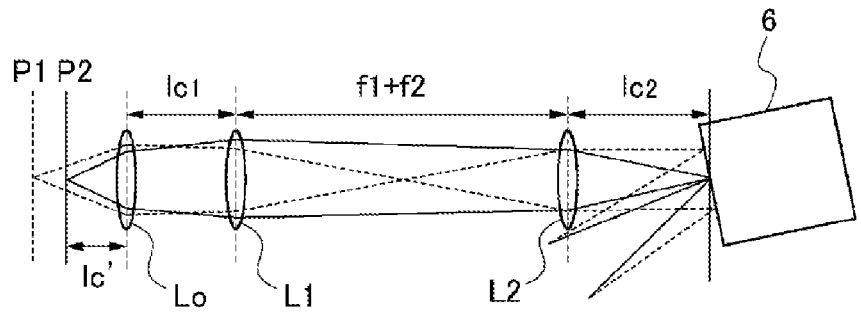

Next, a microscopic device according to a first modification example of the first embodiment of the present invention will be described. FIG. 8 is a diagram illustrating a configuration example of an adaptive optics system in a microscopic device as the modification example. FIGS. 9A and 9B includes schematic diagrams illustrating operations of an imaging-conjugated position adjustment mechanism for fluctuation correction surface in the adaptive optics system. In FIG. 8, the same constituent elements as those of the microscopic device of the first embodiment described above are given the same reference signs as those of the first embodiment, and descriptions thereof will be omitted. FIG. 8 illustrates only the elements related to the position adjustment of the imaging-conjugated surface relative to the fluctuation correction surface in an equivalent manner, but does not illustrate the elements not directly related to the position adjustment.

The distance lc' between the image-forming plane P2 of the fluctuation correction surface and the objective lens Lo can be changed not only by the adjustment of the light path length $lc_1$ between the objective lens Lo and the relay lens L1 illustrated in FIG. 8 but also the adjustment of the light path length $lc_2$ between the relay lens L2 and the wavefront phase modulator 6. By combination of these adjustments, the imaging-conjugated position relative to the fluctuation correction surface can be adjusted in a wider range.

[Configuration of the Adaptive Optics System]

In the microscopic device of the modification example, as illustrated in FIG. 8, a light path length adjustment mechanism is provided in the light path between the relay lens L2 and the wavefront phase modulator 6. There is no particular limitation on the configuration of the light path length adjustment mechanism. For example, as with the mirrors M1 to M4 illustrated in FIG. 1, the light path length adjustment mechanism may be configured such that two mirrors M5 and M6 are arranged at a 90° angle on a slide stage movable along the optical axis.

[Operations]

In the microscopic device of the modification example, when the light path length $lc_1$ between the objective lens Lo and the relay lens L1 and the light path length $lc_2$ between the relay lens L2 and the wavefront phase modulator 6 become shorter, the distance lc' between the image-forming plane P2 of the fluctuation correction surface and the objective lens Lo becomes longer. That is, to adjust the distance lc' between the image forming plane P2 of the fluctuation correction surface and the objective lens Lo, either or both of the light path length $lc_1$ and the light path length $lc_2$ may be increased or decreased.

Before the position adjustment of the imaging-conjugated surface relative to the fluctuation correction surface, as illustrated in FIG. 9A, the opening pupil of the objective lens Lo and the fluctuation correction surface P2 are imaging-conjugated with each other and therefore lc'=0. Then, when the light path length $lc_1$ and the light path length $lc_2$ are decreased to adjust the position of the image-conjugated surface relative to the fluctuation correction surface, the distance lc' between the image-forming plane P2 of the fluctuation correction surface and the objective lens Lo increases as illustrated in FIG. 9B.

At this time, the light path length $lc_1$ between the objective lens Lo and the relay lens L1 and the light path length $lc_2$ between the relay lens L2 and the wavefront phase modulator 6 are changed, but the light path length (=f1+f2) between the relay lens L1 and the relay lens L2 remains unchanged and fixed. As illustrated in FIGS. 9A and 9B, the light (dotted lines) from the observation target or the reference object becomes parallel light both before and after the position adjustment even between the relay lens L2 and the wavefront phase modulator 6 as well as between the objective lens Lo and the relay lens L1.

Accordingly, the position of the image-forming plane P2 of the fluctuation correction surface is moved but the emitted light beam is unchanged between before and after the adjustment. That is, the adjustment of the light path length $lc_2$ has no influence on the planarity of the light from the observation target or the reference object on the wavefront sensor 7. In addition, when the reference object is placed at the same position as the observation target, the adjustment of the light path length $lc_2$ also has no influence on the focus and magnification ratio of the image of the observation target on the imaging camera 8.

In the microscopic device of the modification example, the distance lc' between the image-forming plane P2 of the fluctuation correction surface and the objective lens Lo is changed by the adjustment of the light path length $lc_2$. Accordingly, it is possible to improve the accuracy of wavefront correction and expand the field of view by aligning the position of the image-forming plane P2 of the fluctuation correction surface in the adaptive optics system with the fluctuation layer 102 in the specimen 1. The configurations, operations, and effects of the modification example other than the ones described above are the same as those of the first embodiment.

Second Modification Example of the First Embodiment

Next, a microscopic device of a second modification example of the first embodiment in the present invention will be described. FIG. 10 is a diagram illustrating a configuration example of an adaptive optics system in a microscopic device of the modification example. In FIG. 10, the same constituent elements as those of the microscopic device of the first modification example of the first embodiment described above are given the same reference signs as those of the first modification example of the first embodiment, and descriptions thereof will be omitted. FIG. 10 illustrates only the elements related to the position adjustment of the imaging-conjugated surface relative to the fluctuation correction surface in an equivalent manner, but does not illustrate the elements not directly related to the position adjustment.

When the objective lens Lo is focused on the object target at infinity, as the position of the reference object becomes distant from the observation target, the light from the reference object becomes out of focus and no longer parallel light beams at the outgoing side of the objective lens Lo. As a result, the light shown by the dotted lines from the reference object in FIG. 7 does not become parallel light beams both between the objective lens Lo and the relay lens L1 and between the relay lens L2 and the wavefront phase modulator 6. Accordingly, the flexibility of adjustment of the light path length $lc_1$ and the light path length $lc_2$ is subjected to some constrains.

In the microscopic device of the modification example, a light path length lr between the relay lens L1 and the relay lens L2 is variable and adjustable arbitrarily as illustrated in FIG. 10. Accordingly, the light (dotted lines) from the reference object becomes parallel light beams between the relay lens L2 and the wavefront phase modulator 6, and the displacement of the light path length $lc_2$ at this section is flexible and independent from the convergence of the light beams from the reference object. This displacement is used for adjustment of imaging conjugate between the fluctuation correction surface and the fluctuation layer.

[Operations]

Next, operations of the microscopic device of the modification example will be described. FIG. 11 is a diagram showing a method for changing independently the light path length $lc_2$ by adjustment of the light path length lr. In the microscopic device of the modification example, first, the light path length lr between the relay lens L1 and the relay lens L2 is kept at the sum of focal distances (f1+f2), and the light path length $lc_2$ between the relay lens L2 and the wavefront phase modulator 6 is kept at the focal distance f2. In this state, the reference object is placed at a focal point at the working distance of the objective lens Lo, and the adaptive optics is operated. Then, the imaging-conjugated position between the fluctuation layer and the fluctuation correction surface is adjusted to look for a light path length $lc_1$ at which the effectiveness of the adaptive optics becomes maximum. The decision of the light path length $lc_1$ constitutes rough adjustment of the spacing between the reference object and the fluctuation layer.

After that, the negative feedback control of the adaptive optics by the control unit 12 of the computer 10 is temporarily stopped, and the specimen stage 2 is adjusted to align the observation target with the focal point at the working distance of the objective lens Lo. Then, the light path length lr is adjusted such that the shift from the plane of the incident light wavefront from the reference object to the wavefront sensor 7 becomes smallest, that is, the incident light beams become most vertical. This adjustment can be made by the use of the image from the pupil camera 9 for checking.

Next, the adaptive optics is operated and focused on the observation target in that state. The method for focus adjustment is the same as that of the first embodiment. Alternatively, in the configuration of FIG. 10, the focus adjustment may be made by displacing the wavefront sensor 7, the relay lens L4, and the field stop ST along the optical axis. In this case, the light emitted from the beam splitter BS2 to the imaging observation light path directed to the lens L5 becomes parallel beams, that is, focused at infinity.

As illustrated in FIG. 11, in the rough adjustment of the imaging-conjugated position between the fluctuation layer and the fluctuation correction surface described above, at the stage where the light path length $lc_1$ is decided, the light beams shown by the solid lines from the fluctuation layer of the specimen 1 are parallel between the relay lenses L1 and L2. Accordingly, the adjustment of the light path length lr has no influence on the imaging conjugate between the fluctuation layer and the fluctuation correction surface. Therefore, the adjustment of the light path length $lc_1$ can be made with flexibility. After the adjustment of the light path length lr, the light beams from the reference object are parallel between the relay lens L2 and the wavefront phase modulator 6. Therefore, the adjustment of the light path length $lc_2$ can be made with flexibility, without influence on the entry of the light from the reference object into the wavefront phase modulator 6.

As described above, in the microscopic device of the modification example, the light beams shown by the solid lines from the fluctuation layer, the light beams shown by the broken lines from the observation target, and the light beams shown by the dotted lines from the reference object can be independently set in parallelism in the light path to achieve the independence of focus adjustment. Accordingly, it is possible to reduce aberration by keeping the working distance at which the light beams from the observation target are incident on the objective lens at the designed value such as an infinite distance.

Third Modification Example of the First Embodiment

Next, a microscopic device of a third modification example of the first embodiment of the present invention will be described. The adaptive optics systems in the microscopic devices according to the first embodiment and the first modification example thereof described above can be easily implemented. In addition, in the microscopic device according to the second modification example of the first embodiment, the fluctuation correction layer of the adaptive optics system is adjusted and imaging-conjugated with the fluctuation layer of the specimen, and therefore the focus adjustment can be made independently even when the observation target and the reference object are at different positions.

However, these microscopic devices of the modification examples require a plurality of mirrors. When a large number of mirrors are used as optics for adjustment of the light path length in the adaptive optics system, the light transmission efficiency may become lower. Accordingly, the microscopic device of the modification example uses a small number of mirrors to improve the light transmission efficiency. FIG. 12 is a diagram showing a method for adjusting light path lengths in the microscopic device of the modification example, and FIGS. 13 to 17 are diagrams illustrating specific configuration examples. In FIGS. 12 to 17, the same constituent elements as those of the first modification example of the first embodiment will be given the same reference signs as those of the first modification example of the first embodiment, and descriptions thereof will be omitted.

As illustrated in FIG. 12, in the microscopic device of the modification example, the positions of the relay lenses L1 and L2 are variable along the optical axis. Accordingly, the light path length $pl_1$ from the objective lens Lo to the relay lens L1, the light path length $pl_2$ from the relay lens L1 to the relay lens L2, and the light path length $pl_3$ from the relay lens L2 to the wavefront phase modulator 6 can be separately adjusted. Further, in the microscopic device of the modification example, a mechanism for adjustment of the entire light path length $pl_0$ from the objective lens Lo to the wavefront phase modulator 6 is added to allow all the light path lengths to be independently adjusted.

Moreover, by adding some contrivance to the adjustment of these light path lengths, it is possible to decrease the number of optical elements such as mirrors necessary for the adjustment of the light path lengths and achieve the simple and high-efficiency optical system. Specific configuration examples for carrying out the adjustment method will be described below.

[Example with the Movement of Lenses and the Slides of Turn-Back Mirrors]

In the system of FIG. 13, the relay lenses L1 and L2 are movable, and the slide stage 4 with the turn-back mirrors M1 and M2 is movable in parallel to the optical axes of the incident light and the outgoing light. Accordingly, the light path length $pl_1$, the light path length $pl_2$, and the light path length $pl_3$ illustrated in FIG. 12 are all adjustable.

[Example with the Use of the Objective Lens and the Specimen Stage]

In the system of FIG. 14, the relay lenses L1 and L2 are movable and a stage 22 on which the objective lens Lo and the specimen stage 2 are placed is movable along the optical axis. This increases the degree of freedom of adjustment, and the light path length $pl_1$, the light path length $pl_2$, and the light path length $pl_3$ are all adjustable.

[Example with a Simplified Conjugate Adjustment Stage]

In the system of FIG. 15, the object-side focus of the objective lens Lo is adjusted with the specimen 1 placed on the specimen stage 2 and made movable. In addition, a stage 24 on which the relay lenses L1 and L2 and the stage 4 are placed is also movable in parallel to the optical axis. Moving the stage 24 increases or decreases the light path length $pl_1$ and the light path length $pl_3$ at the same time, thereby to increase the effectiveness of the conjugate of the fluctuation correction surface in the simple system. This configuration has a practical advantage in that the system can be simplified while providing adjustment means for the important light path lengths.

In this system, the stage 22 on which the objective lens Lo and the specimen stage 2 are placed may be movable in parallel to the optical axis, so that the light path length $pl_1$ can be independently adjusted, as in the system of FIG. 14. Further, the stage 4 may be movable so that the light path length $pl_2$ can be independently adjusted.

[Example with the Use of Concave Mirrors Instead of the Relay Lenses]

In the system of FIG. 16, concave mirrors CM1 and CM2 are used instead of the relay lenses L1 and L2 constituting the relay lenses. These concave mirrors CM1 and CM2 are placed on the slide stage 4, and the stage 4 can be moved along the optical axes of the incident light and the outgoing light. This makes it possible to increase or decrease the light path length $pl_1$ and the light path length $pl_3$ at the same time, thereby to enhance the effectiveness of adjustment of conjugate position of the fluctuation correction surface in the simple system.

The stage 22 on which the objective lens Lo and the specimen stage 2 are placed and the slide stage 21 on which the concave mirror CM1 is placed are movable vertically to the moving direction of the slide stage 4. Accordingly, the light path length $pl_2$ can also be independently adjusted. In this system, the use of the mirror surface avoids color aberration and improves the light efficiency because the convergence of the light and the folding of the light path are conducted at the same time. In this system, the stage 22 on which the objective lens Lo and the specimen stage 2 are placed may be movable in parallel to the optical axis so that the light path length $pl_1$ can be independently adjusted.

[Example with the Use of Combined Moving and Rotational Mirrors]

In the system of FIG. 17, the positions of the relay lenses L1 and L2 are variable so that the light path lengths $pl_1$ and $pl_3$ can be adjusted, and the positions and angles of the mirrors M1 and M2 are changed so that the light path length $pl_2$ can be independently adjusted. This system is also compatible with the case where the optical axis of the incident light from the relay lens L1 to the mirror M1 and the optical axis of the outgoing light from the mirror M2 to the relay lens L2 are not parallel to each other. The same or similar functions of independent adjustment of the light path lengths can also be implemented by changing the arrangement sequence of the relay lens L1, the mirror M1, the mirror M2, and the relay lens L2 to another one such as the arrangement sequence of the mirror M1, the relay lens L1, the relay lens L2, and the mirror M2.

Fourth Modification Example of the First Embodiment

Next, a microscopic device according to a fourth modification example of the first embodiment of the present invention will be described. The imaging-conjugated position adjustment mechanism for aligning the fluctuation correction surface with the fluctuation layer can also be implemented by using the objective lens with a finite focal distance. FIGS. 18 and 19 are diagrams illustrating an imaging-conjugated position adjustment mechanism for the fluctuation correction surface in the microscopic device of the modification example, and FIG. 20 is a diagram illustrating a specific configuration example.

[System with the Use of One Relay Lens]

The system with the use of one relay lens between the objective lens Lo and the wavefront phase modulator 6 resembles the system in which the light path length $pl_0$ is zero between the objective lens Lo and the relay lens L1 illustrated in FIG. 12. In the adjustment mechanism of FIG. 18, the light beams shown by the dotted lines from the reference object and the light beams shown by the broken lines from the observation target are made parallel between the relay lens L2 and the wavefront phase modulator 6 by the adjustment of the light path length $pl_2$.

Besides, making variable the light path length $pl_3$ makes it possible to displace the position of the image on the fluctuation correction surface generated in the specimen shown by the solid lines, regardless of the focus position and the magnification ratio of the observation target or the reference object. Accordingly, the imaging-conjugated position of the fluctuation correction surface relative to the fluctuation layer can be adjusted with high flexibility. This adjustment is similar to the adjustment with the use of the objective lens focused at infinity described above.

Meanwhile, as shown by the solid lines in FIG. 18, there exists a plane that converts the outgoing light from the objective lens Lo into parallel light beams focused at infinity at the side nearer the objective lens Lo than the observation target in the specimen. Thus, in the microscopic device of the modification example, the wavefront phase modulator 6 is conjugated with that plane as shown by the solid lines in FIG. 18. Accordingly, the light beams shown by the solid lines become parallel between the objective lens Lo and the relay lens L2, and are not subjected to the influence of adjustment of the light path length $pl_2$. The adjustment of the light path length $pl_2$ between the objective lens Lo and the relay lens L2 can be used for focus adjustment in the case where the observation target and the reference object are different, thereby realizing high-flexibility adjustment.

[System with the Use of Two Relay Lenses]

FIG. 19 illustrates a system using two relay lenses or two relay lens groups in which the light beams shown by the solid lines from the fluctuation layer are made parallel between the relay lens L1 and the relay lens L2 by the negative or positive refractive power of the relay lens L1 and the adjustment of the light path length $pl_1$. Accordingly, it is possible to adjust the light path length $pl_2$ and adjust the planarity and focus of the light beams from the reference object or the light beams from the observation target, without influence on the conjugate relationship between the fluctuation layer and the fluctuation correction layer.

Taking advantage of this, the light beams from the reference object or the light beams from the observation target are adjusted to be parallel between the relay lens L2 and the wavefront phase modulator 6. This makes it possible to adjust the imaging-conjugate between the fluctuation layer and the fluctuation correction surface with high flexibility while avoiding the influence of adjustment of the light path length $pl_3$. This adjustment is similar to the adjustment with the objective lens focused at infinity described above.

[Configuration Example of the Optical System]

The conjugate adjustment optical system using the objective lens or the objective lens group with a finite distance focus described above can constitute an adaptive optics system in combination with the imaging optical system and the wavefront sensor, as in the case of the objective lens with an infinite distance focus. For example, the system using one relay lens illustrated in FIG. 18 is configured as illustrated in FIG. 20. In the system using two relay lenses, the objective lens Lo and the relay lenses L1 and L2 illustrated in FIG. 19 may be used instead of the objective lens Lo and the relay lens L2 illustrated in FIG. 20.

Fifth Modification Example of the First Embodiment

Next, a microscopic device of a fifth modification example of the first embodiment of the present invention will be described. The light path length from the wavefront phase modulator 6 to the emission-side lens and the light path length between the wavefront sensor 7 and the lens in front of the wavefront sensor 7 can be adjusted without having to change the focal distances of the relay lenses L3 and L4.

Figure 21A:
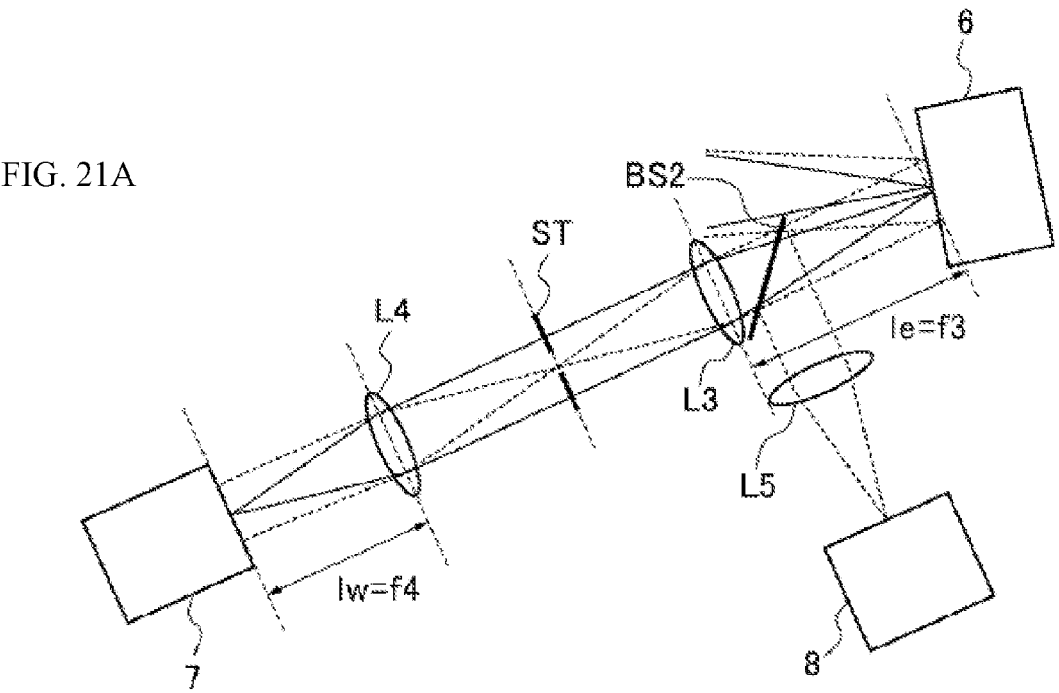
FIGS. 21A and 21B are diagrams illustrating configuration examples of an adaptive optics system in a microscopic device as a fifth modification example of the first embodiment of the present invention.
Figure 21B:
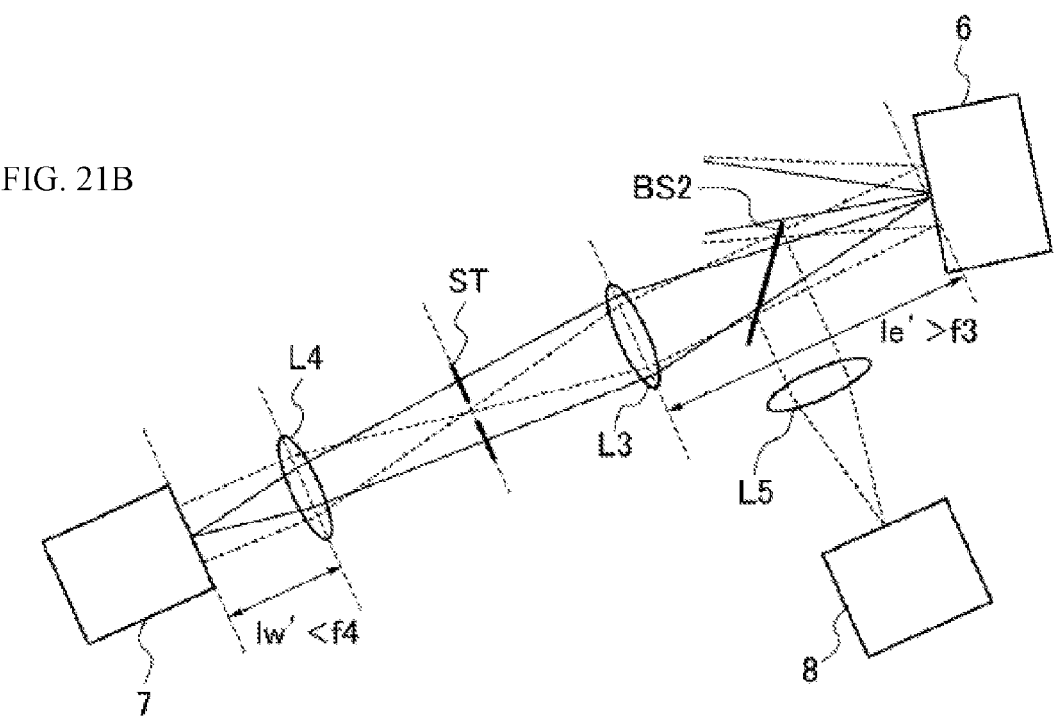

FIGS. 21A and 21B are diagrams illustrating configuration examples of an adaptive optics system in the microscopic device of the modification example. The light path length from the wavefront phase modulator 6 to the relay lens L3 at the emission side is referred to as le, and the light path length from the detection surface of the wavefront sensor 7 to the relay lens L4 in front of the wavefront sensor 7 is referred to as lw. A method for adjusting the light path lengths le and lw will be described below.

The adaptive optics system illustrated in FIG. 21A has a standard arrangement in which the light path length le is set as a focal distance f3 of the relay lens L3, and the light path length lw is set as a focal distance f4 of the relay lens L4. Meanwhile, in the adaptive optics system of FIG. 21B, the light path lengths le and lw are adjusted to light path lengths le' and lw', respectively. The parallel light beam components shown by dotted lines in the wavefront phase modulator 6 and the wavefront sensor 7 remain unchanged against the adjustment of the light path lengths le and lw, and therefore there is no influence on the planarity of the wavefront vertical to the light beams.

At the same time, the wavefront phase modulator 6 and the wavefront sensor 7 may be imaging-conjugated with each other as shown by solid lines. In FIG. 21B, le'>f3 and lw'<f4, but the same adjustment can be made even when le'<f3 and lw'>f4 by reversing the direction of the adjustment. Accordingly, the lengths of the light paths le and lw can be adjusted without having to change the focal distances of the relay lenses L3 and L4.

In the microscopic device of the modification example, for example, when the parallel light path section between the wavefront phase modulator 6 and the relay lens L3 behind the wavefront phase modulator 6 is to be longer to install a light path branching mirror, filter, and the like, it is possible to set the parallel light path section in an appropriate length without replacement of the lenses. Because of the unnecessity of lens replacement, the adjustment is easy. At the time of the adjustment, the diameter of the beams at the parallel light beam section becomes constant at the ratio of the focal distances f3 and f4 of the lenses, and thus the magnification ratio is kept constant between the element surface of the wavefront phase modulator 6 and the element surface of the wavefront sensor 7. As described above, this adjustment method has flexibility relative to the operations of the adaptive optics system.

Further, when the light path lengths le and lw necessary for the arrangement of equipment and components are known in advance, it is possible to minimize the optical system by using the relay lenses L3 and L4 with as the shortest focal distances f3 and f4 as possible.

Sixth Modification Example of the First Embodiment

Next, a microscopic device according to a sixth modification example of the first embodiment of the present invention will be described. FIGS. 22 and 23 are diagrams illustrating configuration examples of an imaging-conjugated position adjustment mechanism for the fluctuation correction surface in the microscopic device of the modification example. As illustrated in FIGS. 22 and 23, the adaptive optics system in the microscopic device of the modification example has a plurality of wavefront phase modulators. The wavefront phase modulators are imaging-conjugated at different positions within the specimen 1. Accordingly, this configuration is compatible with the case where there is a plurality of fluctuation layers or the fluctuation layer is thick.

In the adaptive optics system of FIG. 22, for example, two wavefront phase modulators 16a and 16b are arranged on the optical path together with the relay lenses L1a, L2a, L1b, and L2b, and adjusted to be imaging-conjugated at different positions in the depth direction of the specimen 1. Accordingly, this configuration supports the correction with a plurality of fluctuation layers or a thick fluctuation layer. A distance lca' between the imaging-conjugated image on the fluctuation correction surface generated by the wavefront phase modulator 16a and the objective lens Lo can be changed by adjusting light path lengths lc1a and lc2a illustrated in FIG. 22.

A distance lcb' between the imaging-conjugated image on the fluctuation correction surface generated by the wavefront phase modulator 16b and the objective lens Lo can be adjusted by changing the light path lengths lc1a and lc2a and also changing light path lengths lc1b and lc2b. In the adaptive optics system, as in the case with one wavefront phase modulator, the light beams shown by the dotted lines from the reference object or the observation target become parallel between the objective lens Lo and the relay lens L1a, between the relay lens L2a and the wavefront phase modulator 16a, between the wavefront phase modulator 16a and the relay lens L1b, and between the relay lens L2b and the wavefront phase modulator 16b. Accordingly, it is possible to adjust freely the distances lca' and lcb' between the imaging-conjugated images on the fluctuation correction surface and the objective lens Lo. In addition, as in the case with one wavefront phase modulator, the outgoing light can be focused at infinity by adjusting a light path length lra between the relay lens L1a and the relay lens L2a, and a light path length lrb between the relay lens L1b and the relay lens L2b.

Meanwhile, as illustrated in FIG. 23, in the adaptive optics system using a plurality of wavefront phase modulators, no relay lens may be arranged between the wavefront phase modulators. The distance lca' between the imaging-conjugated image on the fluctuation correction surface generated by the wavefront phase modulator 16a and the objective lens Lo can be adjusted by changing the light path lengths lc1a and lc2a. The distance lcb' between the imaging-conjugated image on the fluctuation correction surface generated by the wavefront phase modulator 16b and the objective lens Lo can be adjusted by changing the light path lengths lc1a and lc2a, and also changing a light path length lcab.

As in the case with one wavefront phase modulator, the light beams shown by the dotted lines from the reference object or the observation target become parallel on these light paths. Accordingly, the distances lca' and lcb' between the imaging-conjugated images on the fluctuation correction surface and the objective lens Lo can be adjusted independently and freely. In addition, as in the case with one wavefront phase modulator, the outgoing light can be focused at infinity by adjusting the light path length lr between the relay lens L1 and the relay lens L2.

As for the correction of the wavefront, for example, the control unit 12 of the computer 10 provides a negative feedback of the measurement value of a wavefront residual obtained by the wavefront sensor 7 placed behind to the wavefront phase modulators 16a and 16b, thereby to make a correction such that the residual decreases toward zero. At the measurement of the wavefront residual, the optical systems are moved as necessary such that the signal from the wavefront sensor 7 includes wavefront fluctuations on the imaging-conjugated surfaces of the wavefront phase modulators 16a and 16b. The optical systems moved at that time may include the wavefront sensor 7, the relay lenses L3 and L4, and the field stop ST. From calculations based on a series of wavefront residual measurement values, optimum control values to be fed back to the wavefront modulators 16a and 16b are determined and used for control operations.

Seventh Modification Example of the First Embodiment

Next, a microscopic device according to a seventh modification example of the first embodiment of the present invention will be described. FIG. 24 is a diagram illustrating an overview of an adaptive optics system in a microscopic device of the modification example. FIG. 25 is a diagram illustrating a configuration of the adaptive optics system illustrated in FIG. 24 using a plurality of wavefront sensors. In the case of using a single reference object, the field of view is limited to the correctable region centered around the reference object. Therefore, in the microscopic device of the modification example, a plurality of reference objects is used for wavefront measurement, and correctable regions are connected to expand the field of view.

As illustrated in FIG. 24, in the microscopic device of the modification example, the wavefront sensor 7 captures a plurality of reference objects RefA, RefB, and RefC at different positions, and measures wavefront fluctuation values at their corresponding effective apertures. Then, the wavefront phase modulator 6 is driven to make corrections with these measured values as error signals. In this manner, it is possible to expand the field of view by connecting the error signals obtained at the respective effective apertures of the reference objects and making corrections to the correction region including all the effective apertures.

In the microscopic device of the modification example, the reference object can be switched by several methods such as moving the field stop ST, moving the wavefront sensor 7, moving a convergence spot of the excitation light source to shift the position where the reference object is to be excited, subjecting the image on the wavefront sensor 7 to image processing and cutting information on part of the reference object, and the like. As illustrated in FIG. 25, instead of the switchover, a plurality of wavefront sensors 17a to 17c corresponding to the plurality of reference objects RefA, RefB, and RefC may be prepared and relay optical systems (lenses L4a to L4c and mirrors M1a to M1d) may be inserted between the wavefront sensors and the reference objects to make position adjustment relative to the reference object.

Further, by using a plurality of wavefront phase modulators, it is possible to expand the field of view in combination with this method even when the fluctuation layer is thick. In this case, the wavefront sensor 7 may be moved as necessary or a plurality of wavefront sensors may be used to perform wavefront measurement.

Eighth Modification Example of the First Embodiment

Next, a microscopic device according to an eighth modification example of the first embodiment of the present invention will be described. FIG. 26 is a diagram illustrating a method for correcting a wavefront tilt component with displacement of lenses in a relay optical system;

FIG. 27 is a diagram illustrating a method for correcting a wavefront curvature component with displacement of the lenses in the relay optical system. In FIGS. 26 and 27, the dotted lines show the positions of the light beams and the lenses when the incident wavefront has no tilt or curvature, and the solid lines show the positions of the light beams and the lenses when the incident wavefront has an tilt or a curvature.

[Correction of the Wavefront Tilt Component]

The wavefront tilt component can be corrected by mounting a publicly-known tip tilt mirror or a wavefront phase modulator on a tip tilt mount, for example. Otherwise, the wavefront tilt component can also be corrected by displacing (laterally displacing) the relay lens vertically to the optical axis. For example, as illustrated in FIG. 26, when the tilt of the incident wavefront is corrected by laterally displacing the relay lens L1 relative to the optical axis as shown by a one-point chain line, the relay lens L2 may be further reversely displaced to cancel out the shake of the light beam to keep constant the position of the outgoing light beam.

[Correction of the Wavefront Curvature Component]

The wavefront curvature component can be corrected by changing the distance between the relay lens L1 and the relay lens L2. For example, as illustrated in FIG. 27, the relay lens L1 may be displaced along the optical axis as shown by an one-point chain line to adjust the distance between the relay lens L1 and the relay lens L2.

At the corrections of the wavefront tilt and focus described above, it is possible to increase the maximum value of correctable wavefront distortion under a control in conjunction with the wavefront phase modulator 6 so as to decrease the error signal from the wavefront sensor 7.

Ninth Modification Example of the First Embodiment

Next, as a ninth modification example of the first embodiment of the present invention, the use of calculated values and the simplification of the adjustment procedure will be described. Various set values such as the light path length lc or the light path lengths lc1 and lc2 adjusted such that the fluctuation layer and the fluctuation correction surface are imaging-conjugated with each other, the light path length lr determined by the position of the reference object, the positions of the wavefront sensor 7, the relay lens L4, and the field stop ST decided such that the image comes into focus, the deviation and offset values of the wavefront sensor 7 and the wavefront phase modulator 6, are decided by prescribed values of the focal distance of the optical lenses, the position of the fluctuation layer, the position of the reference object, and others.

For these values, the set values equivalent to those obtained by the adjustment operations described above can be determined in advance by calculations and simulations based on optical designs. Specifically, the set values may be determined in advance by the adjustment operations or the calculations, recorded in association with the lenses to be used, the position of the reference object, and the position of the fluctuation layer, and used in the actually used system depending on the situation of the observation. This facilitates the adjustment operations and further allows automation of the adjustment operations.

Tenth Modification Example of the First Embodiment

Next, as a tenth modification example of the first embodiment of the present invention, the application to acquisition of Z stack images will be described. In general, a group of tomographic images shot with shifts in the focus of the microscope at specific intervals in the depth direction of the specimen is called as Z stack images. By applying the foregoing adjustment method to the movement of the focus for acquisition of the Z stack images, the fluctuation correction surface of the adaptive optics system and the fluctuation layer in the specimen can be imaging-conjugated with each other. Accordingly, it is possible to prevent disturbances and fluctuations at the time of the correction by the adaptive optics.

FIG. 28 is a diagram illustrating a configuration example of an adaptive optics system in a microscopic device according to the modification example. As illustrated in FIG. 28, in the adaptive optics system in the microscopic device of the modification example, the specimen stage 2 and the objective lens Lo are moved integrally to adjust the light path lengths, and the relay lenses L1 and L2 are moved along the optical axis, similar to the configuration of FIG. 14.

First, the focus in the specimen 1 is displaced to acquire the Z stack images. Specifically, as illustrated in FIG. 28, the specimen stage 2 on which only the specimen 1 is placed is moved relative to the objective lens Lo (displacement amount i). Subsequently, the positions of the stage 22 on which the specimen stage 2 and the objective lens Lo are placed, and the relay lenses L1 and L2 are adjusted to displace the light path length from the objective lens Lo to the relay lens L1, the light path length from the relay lens L1 to the relay lens L2, and the light path length from the relay lens L2 to the wavefront phase modulator 6 (displacement amounts ii to iv). At that time, the position of the fluctuation correction surface and the position of the fluctuation layer in the specimen are kept in imaging conjugate.

Next, the focus adjustment is performed by the method described above such that the imaging camera 8 is imaging-conjugated with the observation target and comes into a focus. Specifically, the image-forming lens L5 is focus-adjusted (displacement amount v); an offset is added to a wavefront measurement signal from the wavefront sensor 7, a negative feedback of the offset signal is provided as a deviation signal to the elements 6a of the wavefront phase modulator 6, and the elements 6a are controlled and given a curvature on the reflection surface (displacement amount vi); and a slide stage 25 on which the field stop ST, the relay lens L4, and the wavefront sensor 7 are placed is displaced and adjusted such that the incident light from the reference object becomes a planar wave on the wavefront sensor 7 (displacement amount vii), for example.

In this manner, the displacement amounts (displacement amounts ii to vii) of the series of optical elements corresponding to the movement of focus of the objective lens on the specimen (displacement amount i) can be determined in advance by experiments or calculations. Accordingly, these adjustments can be automatically performed during the acquisition of the Z stack images. Similarly, while the displacement amount i illustrated in FIG. 28 is set as a fixed value, the focus of the image-forming lens L5 can be adjusted by the displacement amount v to acquire the Z stack images. This method may increase aberration and narrow the image focus adjustment range, but can be readily implemented.

Keeping constantly the imaging-conjugate relationship between the fluctuation layer of the specimen 1 and the fluctuation correction surface of the adaptive optics system makes it possible to prevent deviations of the correction values in the adaptive optics system. Accordingly, it is possible to eliminate or reduce the consumption of time for re-correction of the adaptive optics during the acquisition of the Z stack images. Conventionally, there is need to operate the adaptive optics for making corrections each time when the focus is displaced in the Z axis direction. The application of the modification example can improve this situation.

Eleventh Modification Example of the First Embodiment

Next, as an eleventh modification example of the first embodiment of the present invention, the application to time-lapse acquiring will be described. In general, the observational method for performing continuous acquiring at constant time intervals is called time-lapse acquiring. In this case, the time-lapse acquiring includes acquiring at low-speed time intervals and acquiring at a video rate or higher-speed time intervals.

Although the time-lapse acquiring is publicly known, the time-lapse acquiring in the microscopic device of the modification example is performed while image degradation is corrected by the adaptive optics. This improves the observation accuracy. In addition, the observation accuracy can further be increased by holding the fluctuation surface imaging-conjugated with the correction surface of the adaptive optics.

Specifically, once the positions of the fluctuation component and the reference object in the specimen are aligned with the objective lens Lo to complete the adjustment of the imaging-conjugated position relative to the fluctuation correction surface, even when the fluctuation component changes in shape or content, the time-lapse acquiring can be performed while the changes are corrected by the adaptive optics system. In addition, the time-lapse acquiring can be automated by the use of a publicly-known software application (Metamorph produced by Molecular Devices, LLC. or the like).

Further, by combining the automated acquisition of the Z stack images described above with the automated time-lapse acquiring, it is possible to acquire the Z stack images continuously to obtain 4D (3D+time) images. When the observation target is to be moved three-dimensionally, by making settings before acquiring such that the Z stack images can be acquired within the possible range of movement of the observation target, high-definition images of the three-dimensionally moving observation target can be obtained while the fluctuation component is corrected. In this manner, even when the observation target is to be moved to change the fluctuation component in shape and content, as far as the position of the fluctuation surface is fixed, the fluctuation surface can be adjusted to be imaging-conjugated with the correction surface of the adaptive optics to obtain 4D images with a further improvement in observation accuracy.

Further, even when the position of the fluctuation surface is to be moved, it is possible to control automatically the fluctuation correction surface and the fluctuation surface to be imaging-conjugated with each other based on the image acquired by the pupil camera 9. Specifically, at a stage prior to acquiring, the possible range of movement of the fluctuation surface is set in advance. Then, before each time-lapse acquiring, the Z stack images are acquired by the pupil camera 9 within the possible range of movement of the fluctuation surface while the distance between the objective lens Lo and the relay lens L1 or between the relay lens L2 and the wavefront phase modulator 6 is changed.

When the imaging-conjugated surface relative to the fluctuation correction surface and the fluctuation layer in the specimen become close to each other, the position adjustment control unit (not illustrated) automatically controls the imaging-conjugated position adjustment mechanism such that the neighborhood of the fluctuation layer and the fluctuation correction surface become imaging-conjugated with each other with a decrease in contrast resulting from the wavefront phase of the image or the like as an index. After that, the Z stack images are acquired by the method described above. By performing this process at each time-lapse acquiring, 4D images can be obtained with improvement in observation accuracy even when both the observation target and the fluctuation surface are moved.

Twelfth Modification Example of the First Embodiment

Next, as a twelfth modification example of the first embodiment of the present invention, a method for adjusting an excitation wavelength and a fluorescence wavelength between the reference object and the observation target will be described. When the light beams to be detected from the reference object and the observation target are both fluorescent light, the characteristics of excitation light and fluorescence wavelength can be shifted between the two light beams to improve distinctiveness and prevent performance degradation under mutual influences.

Specifically, the fluorescent light can be selectively excited in the reference object and the observation target by adjusting and choosing fluorescent substances for the reference object and the observation target with a difference in excitation wavelength characteristics, and switching the wavelength of the light source according to their respective excitation wavelengths such that one excitation efficiency is higher than the other.

In addition, fluorescent substances for the reference object and the observation target are chosen with a difference in fluorescence wavelength characteristics, and a dichroic mirror is used as the beam splitter BS2 as necessary to increase distinctiveness between their respective fluorescent light beams. Further, a wavelength filter for making the transmission of the fluorescent light from the reference object higher than the transmission of the fluorescent light from the observation object is inserted in the wavefront measurement light path, and a wavelength filter for making the transmission of the fluorescent light from the observation target higher than the transmission of the fluorescent light from the reference object is inserted in the imaging observation light path. This reduces mutual influences.

The distinction between the fluorescence wavelengths by the filters or the like described above is also applicable to the case where the reference object and the observation target are excited at the same time by a single or plural excitation light beams.

Thirteenth Modification Example of the First Embodiment

Next, as a thirteenth modification example of the first embodiment of the present invention, image processing using wavefront fluctuation information will be described. Point image distribution can be estimated using the information from the wavefront sensor 7 and the wavefront phase modulator 6 in the adaptive optics system. In the microscopic device of the modification example, the fluctuation correction surface is made variable to obtain three-dimensional fluctuation information. Accordingly, it is possible to visualize the fluctuation information as an image of a three-dimensional target such as a microscopic specimen, and improve the accuracy of estimation of point image distribution. As a result, the three-dimensional fluctuation structure and the estimation of the point image distribution can be used for image recovery processing.

Second Embodiment

Next, a microscopic device according to a second embodiment of the present invention will be described. At present, wavefront sensors are mainly of a Shack-Hartmann type, and their adjustment principles depend on the imaging conjugate of optical surfaces. Therefore, the conjugated position adjustment can be made in combination with other publicly-known types. The wavefront sensors may be of a curvature type, a phase-contrast type, an tilt detection type using other Hartmann masks such as a talbot mask. Among them, the phase-contrast type is a technique for using the visualization and detection of optical phase by a phase-contrast method in detection of wavefront phase.

Meanwhile, when wavefront correction is made using a Shack-Hartmann-type wavefront tilt sensor or the like, some wrinkle-like deformation called waffle mode may be seen in the wavefront phase modulator in which adjacent elements are alternately displaced in the vertical direction under influence of noise. This is likely to occur at the time of microscopic observation with many small fluctuations. FIG. 29 is a schematic diagram illustrating a wavefront shape in the waffle mode. As illustrated in FIG. 29, the wavefront distortion in the waffle mode is difficult to detect by the wavefront tilt detection method using a Shack-Hartmann sensor or the like. Therefore, once the distortion occurs, the convergence of the control becomes deteriorated. Accordingly, when a waffle-mode wavefront shape occurs under strong noise influence, the control diverges with reduction in accuracy and becomes unstable.

Figure 30A:
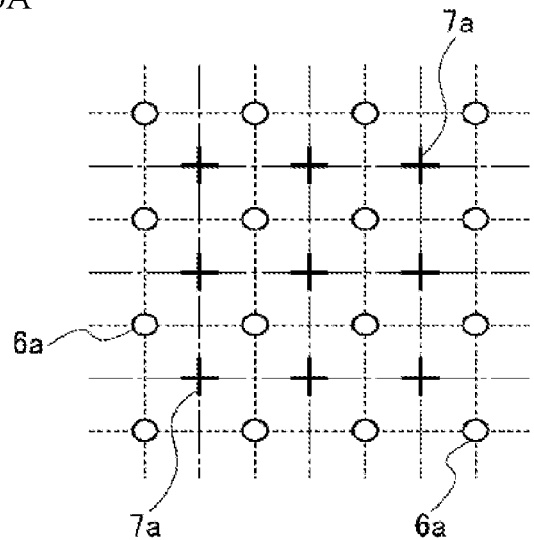
FIGS. 30A and 30B are diagrams illustrating arrangements of elements of a wavefront sensor relative to the wavefront phase modulator.
Figure 30B:
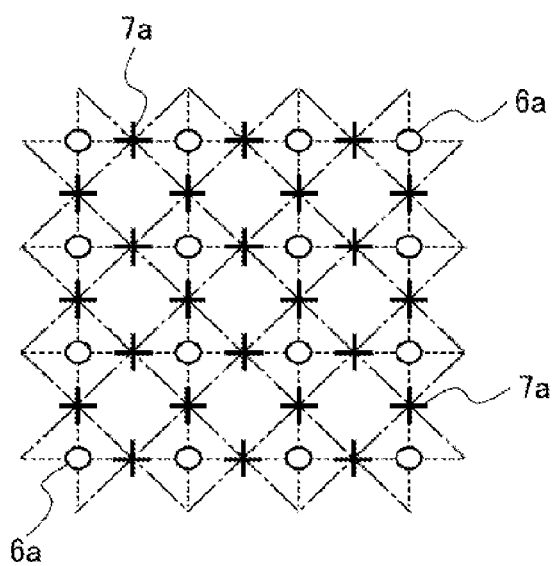
Figure 31A:
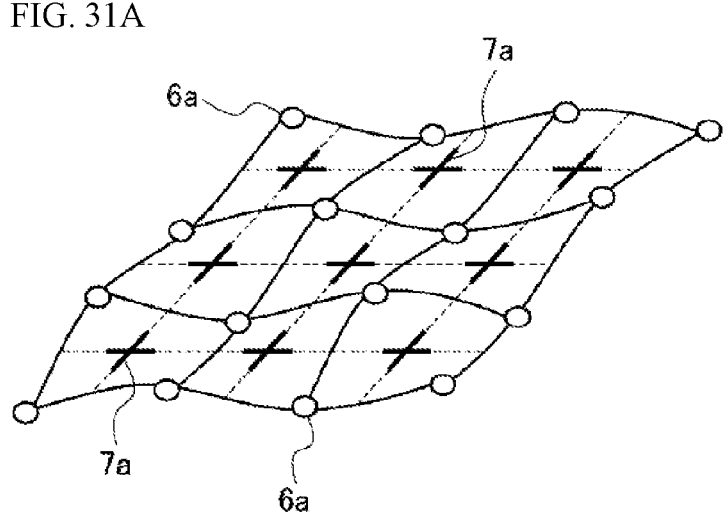
FIGS. 31A and 31B are diagrams illustrating the relationship between differences in element arrangement of wavefront sensor and detection sensitivity in the waffle mode.
Figure 31B:
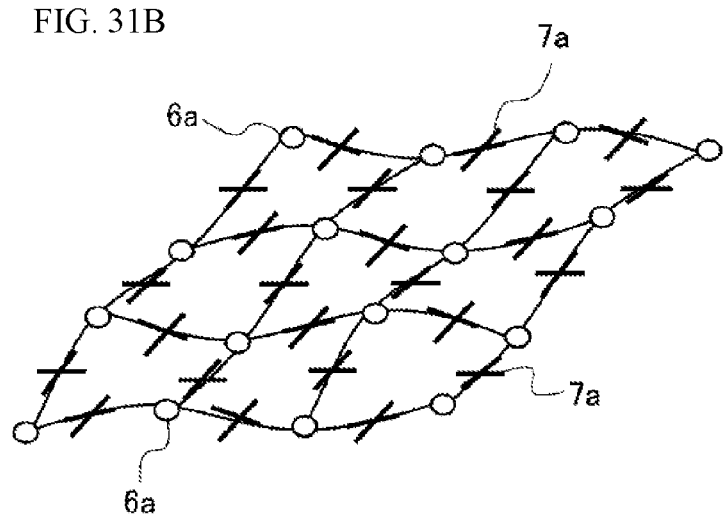
Figure 32A:
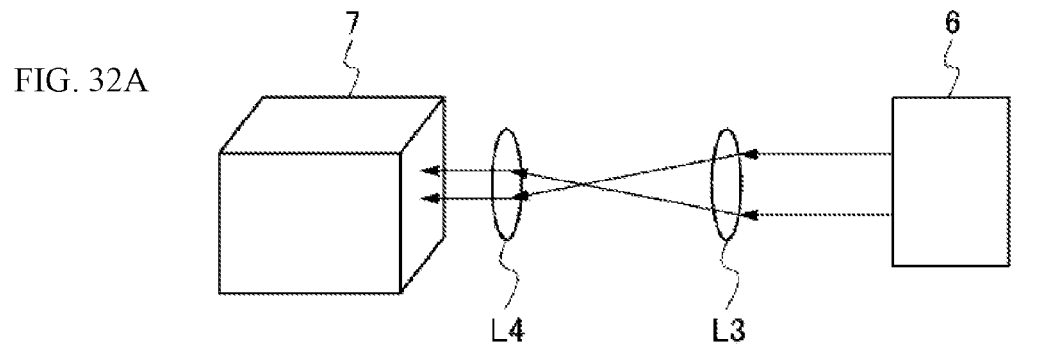
FIGS. 32A and 32B are diagrams illustrating the relationship between the 45° rotated arrangement of the wavefront sensor and the changes in magnification ratio of the optical system.
Figure 32B:
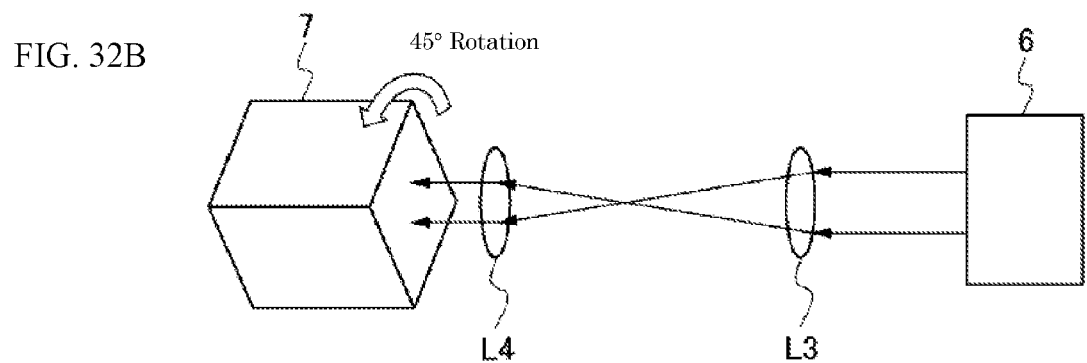

FIGS. 30A and 30B are diagrams illustrating arrangements of elements of the wavefront sensor relative to the wavefront phase modulator, and FIGS. 31A and 31B includes diagrams illustrating the relationship between differences in arrangement of wavefront sensor elements and detection sensitivity to the waffle mode. FIGS. 32A and 32B are diagrams illustrating the relationship between the 45° rotated arrangement of the wavefront sensor and the changes in magnification ratio of the optical system. In the microscopic device of the embodiment, the arrangement of the elements 7a of the wavefront sensor 7 illustrated in FIG. 30A is rotated at a 45° angle and inclined as illustrated in FIG. 30B, and the intervals between the elements 7a are adjusted to align with the centers of the elements 6a adjacent in the vertical and horizontal directions of the wavefront phase modulator 6. This makes the microscopic device also sensitive to the waffle mode.

In the general element arrangement of FIG. 30A, each of the partially opening elements 7a of the wavefront sensor 7 illustrated in FIG. 31A is arranged at a saddle point among the four adjacent elements 6a of the wavefront phase modulator 6. Therefore, the tilt resulting from the waffle mode illustrated in FIG. 29 cannot be detected. In contrast to this, in the 45° inclined arrangement illustrated in FIG. 30B, the tilt resulting from the waffle mode can be detected between the convex and concave elements 6a adjacent in the vertical and horizontal directions of the wavefront phase modulator 6 illustrated in FIG. 31B.

Accordingly, in the microscopic device of the embodiment, to prevent performance degradation due to the waffle mode, as illustrated in FIG. 32B, a Shack-Hartmann-type wavefront tilt sensor is rotated at a 45° angle around the optical axis as a rotation axis, the lengths of the focuses of the objective lens Lo and the relay lens L1 are adjusted to change the magnification ratio, and the elements 6a of the wavefront phase modulator 6 illustrated in FIG. 31A are arranged as illustrated in FIG. 31B. Accordingly, it is possible to provide sensitivity to the waffle mode and improve the adaptive optics in operational stability.

Third Embodiment

Next, a laser injector device according to a third embodiment of the present invention will be described, taking the application to a laser injector microscope as an example. The adaptive optics system described above can also be used to correct diffraction scattering at the time of injection of laser or the like into the specimen taking advantage of the regressivity of light. FIG. 33 is a schematic diagram illustrating a configuration of a laser injection microscope using a laser injection device according to the embodiment.

As illustrated in FIG. 33, the suppression of scattering in the specimen 1 can be expected by entering laser light from a laser light source LS via the wavefront phase modulator 6 in the adaptive optics system. A fluorescent substance excitable by the incident laser can be arranged in the reference object for operating the adaptive optics system. When the excitable fluorescent substance is small in amount and difficult to arrange such as when using an infrared laser, fluorescent excitation by a general light source may be used as well, or an excitation laser for the reference object different from the injection laser may be arranged sharing the optical axis with the injection laser to excite the fluorescent substance and use the resultant fluorescent light as the reference object.

The laser injection device of the embodiment is applicable to systems in which the genes and substances of specific cells and cellular regions can be optically adjusted, such as a gene induction system for specific cells using heat shock or the like (for example, an InfraRed Laser-Evoked Gene Operator manufactured by Sigmakoki Co., Ltd.) and optogenetics.

Fourth Embodiment

Next, a phase-contrast microscopic device according to a fourth embodiment of the present invention will be described. FIG. 34 is a schematic diagram illustrating a configuration of the phase-contrast microscopic device according to the embodiment. A phase-contrast method is applied to a wavefront adjusted by fluctuation correction in the adaptive optics system to improve the accuracy of optical phase imaging.

As illustrated in FIG. 34, in the phase-contrast microscope of the embodiment, a slit or pinhole PH is provided between the light source 3 of a light source unit 30 and a light-collecting lens L8. Since the image of the slit or pinhole PH of the light source unit 30 appears on the imaging observation light path behind the beam splitter BS2, a phase-contrast mask PM is arranged at an imaging unit 80 to obtain a phase-contrast image by an image-forming lens L7 and the imaging camera 8 behind the phase-contrast mask PM. In FIG. 34, the broken lines show 0-order diffracted light beams, the dotted lines show the light beams from the observation target and the reference object, and the solid lines show the light beams from the fluctuation correction surface.

The basic principles of phase-contrast microscopes are already publicly known. Incorporating the adaptive optics system into the phase-contrast microscope achieves a sharp phase-contrast image. In addition, adjusting the conjugated positions of the fluctuation layer and the fluctuation correction surface allows the effectiveness of the adaptive optics to be achieved in a wider range and at higher accuracy. Of the correcting effects of the adaptive optics, the detection and correction of oblique components is equivalent to automatic alignment of the optical axis, thereby achieving improvement in image accuracy. This is applicable to the automatization of alignment of the pinhole or slit by the phase-contrast method.

Fifth Embodiment

Next, a differential interference microscopic device according to a fifth embodiment of the present invention will be described. FIG. 35 is a schematic diagram illustrating a configuration of the differential interference microscopic device according to the embodiment. By applying differential interferometry to the wavefront adjusted by fluctuation correction in the adaptive optics system, the accuracy of optical phase imaging can be improved as in the case of the phase-contrast method described above.

As illustrated in FIG. 35, in the differential interference microscopic device of the embodiment, the transmission light source 3 for illumination of the specimen 1 is dedicated for differential interference. A light source unit 31 lets the light from the light source 3 through a pinhole P, a collimator C, and a polarizing filter PL1. Then, a Wollaston polarizing prism PP1 separates the light path for each polarization to shift the light laterally, and the condenser lens L9 projects the light onto the specimen 1. In FIG. 35, the broken lines show 0-order diffracted light beams, the dotted lines show the light beams from the observation target and the reference object, and the solid lines show the light beams from the fluctuation correction surface.

In the differential interference microscopic device of the embodiment, the light beams having been corrected by the adaptive optics system, entered into the light-receiving optical system on the imaging observation light path, and separated for each polarization by the Wollaston polarizing prism PP2 of the imaging unit 81, are composited again to cause interference. As a result, the change in the light path length in the spatial direction generates variations of light and shade in the image. After having passed through the polarizing prism PP2, the light beams pass through a polarizing filter PL2, and then enter into the imaging camera 8 through the image-forming lens L7 on the back side, thereby to obtain a differential interference image.

The basic principles of differential interference microscopic devices are already publicly known. Incorporating the adaptive optics system into the differential interference microscopic device achieves a sharp differential interference image. In addition, adjusting the conjugated positions of the fluctuation layer and the fluctuation correction surface allows the effectiveness of the adaptive optics to be achieved in a wider range and at higher accuracy. Of the correcting effects of the adaptive optics, the detection and correction of oblique components is equivalent to automatic alignment of the optical axis, thereby achieving improvement in image accuracy.

Sixth Embodiment

Next, a confocal scanning microscopic device according to a sixth embodiment of the present invention will be described. FIG. 36 is a schematic diagram illustrating a configuration of the confocal scanning microscopic device according to the embodiment. It is possible to achieve performance improvement by incorporating the adjustment of the conjugated positions of the fluctuation layer and the fluctuation correction surface to various scanning-type adaptive optical microscopes.

A specific configuration example is as illustrated in FIG. 36. A confocal scanning unit 82 is arranged behind the adaptive optics system to prevent the position gap between the adaptive optics system and the specimen 1 at the time of scanning. The scanning operation and the adaptive optical operation are independently performed to realize high-speed scanning. In addition, performance improvement is achieved by incorporating the adjustment of the conjugated positions of the fluctuation layer and the fluctuation correction surface. The focus adjustment may be made through the adjustment in the scanning optical system or by using the focus adjustment method described above.

The confocal scanning microscopic device of the embodiment can be implemented by arranging the confocal scanning optical system on the imaging observation light path of the beam splitter BS2. To operate the confocal scanning microscopic device, first, the adaptive optics system is operated to perform wavefront compensation. When the reference object is to be excited by fluorescent light during the operation of the adaptive optics, a scanning laser may be used as far as it is on the same wavelength.

While the pattern of the wavefront phase modulator is fixed, the specimen 1 is scanned with laser using the confocal scanning optical system arranged in the imaging observation light path of the beam splitter BS2 to achieve high-definition confocal microscopic observation. The basic principles of confocal microscopes are publicly known. By incorporating the adjustment of the conjugated positions of the fluctuation layer and the fluctuation correction surface into the confocal microscope and making the adaptive optics effective in a wider range and at higher accuracy, performance improvement can be achieved. Of the correcting effects of the adaptive optics, the detection and correction of oblique components is equivalent to alignment of the optical axis, thereby achieving improvement in image accuracy by automatic alignment of the optical axis.

Specifically, as illustrated in FIG. 36, laser light emitted from a laser light source LS passes through a polarizing element PL1 and a wavelength plate WP1, then passes through a relay lens L10 and a pinhole P1, and then becomes parallel light beams through a collimate lens L7. The laser light is inclined by galvanometer mirrors GMX and GMY to scan and excite the specimen 1. The obtained fluorescent light travels reversely from the beam splitter BS2 to the confocal scanning system 82, and is guided by the beam splitter BS3 to a photomultiplier tube PMT.

Relay lenses L11 and L12 are arranged between the beam splitter BS3 and the photomultiplier tube PMT, and a pin hole P2 is arranged near an intermediate point between the relay lenses L11 and L12 to shut off the fluorescent light from fault planes other than the focal plane and attenuate the same. The fluorescent light passes through the pinhole P2, then passes through a wavelength plate WP2 and a polarizing element PL2, and then enters into the photomultiplier tube PMT. Accordingly, an image formation and storage unit of a computer 14 obtains a tomographic image of the focal plane. The configuration of the embodiment is not limited to the scanning confocal microscope using the galvanometer mirrors described above but is also applicable to other systems with scanning mechanisms such as an optical system with a spinning disc as well as the confocal scanning system.

Seventh Embodiment

Next, a multiphoton-excitation microscope according to a seventh embodiment of the present invention will be described. FIG. 37 is a schematic diagram illustrating a configuration of the multiphoton-excitation microscope according to the embodiment. As illustrated in FIG. 37, the multiphoton-excitation microscope of the embodiment is provided with a laser scanning detection optical system for multiphoton excitation (multiphoton scanning detection unit 83) in the imaging observation light path branched from the beam splitter BS2.

To make observations by this microscopic device, first, the adaptive optics system is operated to perform wavefront compensation. At that time, when fluorescence excitation of the reference object is necessary for operations of the adaptive optics, two-photon excitation may be caused by a scanning laser light source LS provided in the multiphoton scanning detection unit 83. Then, the specimen is scanned by the laser two-photon excitation and observed by the two-photon microscope.

The basic principles of multiphoton-excitation microscopes are publicly known. Incorporating the adaptive optics system into the multiphoton-excitation microscope achieves high-definition two-photon microscopic observation. In addition, adjusting the conjugated position of the fluctuation layer and the fluctuation correction surface allows the effectiveness of the adaptive optics to be achieved in a wider range and at higher accuracy. Of the correcting effects of the adaptive optics, the detection and correction of oblique components is equivalent to alignment of the optical axis, thereby achieving improvement in image accuracy by automatic alignment of the optical axis.

Specifically, as illustrated in FIG. 37, the laser light emitted from the laser light source LS passes through relay lenses L10 and L7, is inclined by the galvanometer mirrors GMX and GMY, and becomes excitation light by multiphoton absorption to scan the specimen. The obtained fluorescent light travels reversely from the beam splitter BS2 to the multiphoton scanning detection unit 83, and is guided by the beam splitter BS3 to a photomultiplier tube PMT.

The relay lenses L11 and L12 are arranged between the beam splitter BS3 and the photomultiplier tube PMT, and the pin hole P2 is arranged near an intermediate point between the relay lenses L11 and L12 to shut off the fluorescent light from fault planes other than the focal plane and attenuate the same. The fluorescent light passes through the pinhole P2, then passes through a bandpass filter BPF, and then enters into the photomultiplier tube PMT. Accordingly, the image formation and storage unit of the computer 14 obtains a tomographic image of the focal plane. The multiphoton microscope may not have the pinhole P2, or may be configured such that a photoelectron detector such as a PMT is combined with a dichroic mirror and arranged just behind the objective lens, depending on the intended use applications such as deep-tissue acquiring. In addition, the configuration of the embodiment is not limited to the scanning multiphoton microscope using the galvanometer mirrors but is also applicable to other optical systems such as an optical system using a spinning disc.

Eighth Embodiment

Next, a microscopic device according to an eighth embodiment of the present invention will be described. The adaptive optics system of the present invention is applicable to various microscopic devices as well as the various microscopic devices described above. Specifically, the basic principles of super-resolution microscopic devices are publicly known. Incorporating the adaptive optics system into the super-resolution microscopic device makes it possible to improve the convergence performance and cross-section shapes of incoming and outgoing wave packets and achieve performance improvement.

For example, a saturated excitation microscopic device (SAX microscope) suppresses the spread of a saturated excitation section due to degradation of light-collecting properties of incident laser resulting from refraction or diffraction, even under the presence of aberration caused by fluctuations in the observation target. In addition, the SAX microscope improves resolving power by correcting fluctuations in detection light entered from the specimen into the objective lens. The improvements in convergence performance and cross-section shapes of the incoming and outgoing wave packets by the adaptive optics can also be applied to accuracy improvement by a method called super-resolution.

A stimulated emission depletion microscopic device (STED microscopic device) suppresses degradation in the shapes of excitation light spots and stimulated emission light beams resulting from refraction and diffraction, and corrects fluctuations in the detection light entered from the specimen into the objective lens, even under the presence of aberration caused by fluctuations in the specimen, thereby improving resolving power.

When measuring the center of strength of the detection light positions entered from a particle structure below diffraction limitation as a specimen to the objective lens and the position of its center of gravity, the STED microscopic device suppresses the degradation of excitation light spots resulting from refraction or diffraction even under the presence of aberration caused by fluctuations in the specimen, and corrects the fluctuations in the detection light entering from the specimen into the objective lens to improve the accuracy. In addition, of the correcting effects of the adaptive optics, the detection and correction of oblique components is equivalent to automatic alignment of the optical axis, thereby achieving improvement in image accuracy.

A structured illumination microscopic device (SIM microscopic device) suppresses the degradation of illumination patterns resulting from refraction or diffraction even under the presence of aberration caused by fluctuations in the specimen, and corrects the fluctuations in the detection light entering from the specimen into the objective lens to improve the resolving power. Further, the adaptive optics system of the present invention is applicable to various microscopic devices such as polarizing microscopic devices as well as the various microscopic devices described above.

Ninth Embodiment

Next, a telescopic device according to a ninth embodiment of the present invention will be described. FIG. 38 is a schematic diagram illustrating a configuration of the telescopic device according to the embodiment. The technique for combining the adaptive optics with the telescopic device has been conventionally being studied. The technique for establishing imaging-conjugate between the height of air fluctuations and the fluctuation correction surface to make the adjustment permanent has been already proposed.

In contrast to this, as in the telescopic device illustrated in FIG. 38, when the conjugated position of the adaptive optics system in the telescopic device is freely adjustable, it is possible to adjust independently the position of the reference object existing separately from the subject, while making adjustments such that imaging-conjugate is established between the position of fluctuations in the air or the like in the light path to the subject and the correction surface of the adaptive optics system. This maximizes the effectiveness of the adaptive optics.

Further, the telescopic device of the embodiment has a system more flexible in setting than conventional ones and thus is capable of wide application. Taking advantage of a wide range of adjustment function, the adaptive optics system can be designed as a general-purpose replaceable adaptive optics system, independently from object optical systems such as a main mirror and a sub mirror (a primary mirror and a secondary mirror) of a telescope TS. In addition, the telescopic device may be used as an adaptor to be combined with a camera interchangeable lens.

EXAMPLES

The effectiveness of the present invention will be specifically described below, showing an example of the present invention and a comparative example. First, using the adaptive optical microscope of the present invention, an artificial specimen was observed through wavefront correction by the conventional adaptive optics system before the imaging-conjugated position adjustment illustrated in FIG. 5A and the adaptive optics system with the fluctuation correction surface imaging-conjugated with the fluctuation layer illustrated in FIG. 5B according to the present invention, and the resultant image accuracies were compared.

The artificial specimen was prepared by printing a grid pattern with intervals of 10 μm as an observation target on a slide glass. The reference object was prepared by attaching 3.5 μm-diameter fluorescent beads to the grid pattern surface. A fluctuation generation surface was formed by attaching 50 μm-diameter glass beads as spacers to one corrugated side of a cover glass, putting the cover glass on the slide glass such that the corrugated surface faces the slide glass, and injecting a silicone oil with different in refractive index from the glass into the gap between the slide glass and the cover glass.

Figure 39A:
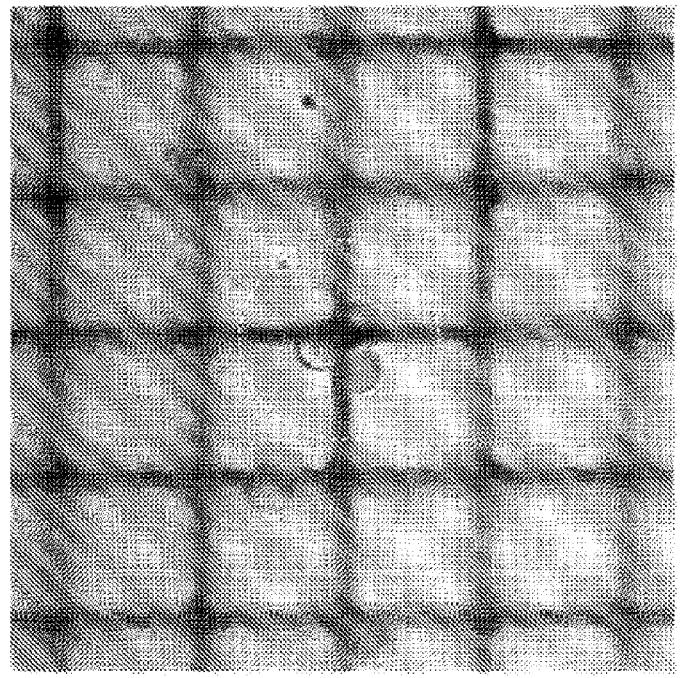
FIG. 39A is a photomicrograph of an artificial specimen taken such that wavefront correction is made by a conventional adaptive optics system without imaging-conjugated position adjustment.
Figure 39B:
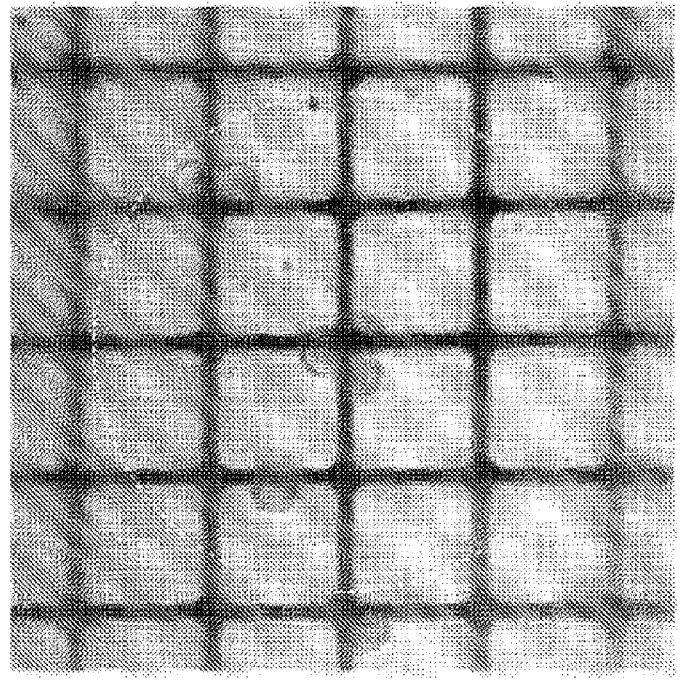
FIG. 39B is a photomicrograph of an artificial specimen taken such that wavefront correction is made while a fluctuation compensation surface is imaging-conjugated with a fluctuation layer by the adaptive optics system of the present invention.

As an observation method, the adaptive optics was operated with fluorescent light from the fluorescent beads as the reference object, and then the image in a bright field was observed with focus on the grid. FIG. 39A is a photomicrograph of the artificial specimen taken such that wavefront correction is made by the conventional adaptive optics system without imaging-conjugated position adjustment, and FIG. 39B is a photomicrograph of the artificial specimen taken such that wavefront correction is made by the adaptive optics system of the present invention while a fluctuation correction surface is imaging-conjugated with a fluctuation layer. In FIGS. 39A and 39B, the viewing areas improved in resolution by the adaptive optics are shown by dotted lines. The fluorescent beads used as the reference object are seen at the centers of the areas shown by the dotted lines.

As compared to the image shown in FIG. 39A taken with the fluctuation correction surface imaging-conjugated with the pupil of the objective lens, it can be seen that the resolution is improved in the image shown in FIG. 39B taken by a microscope using the adaptive optics system to which the present invention is applied, by the conjugate adjustment mechanism establishing imaging-conjugate between the fluctuation surface and the fluctuation correction surface.

Figure 40A:
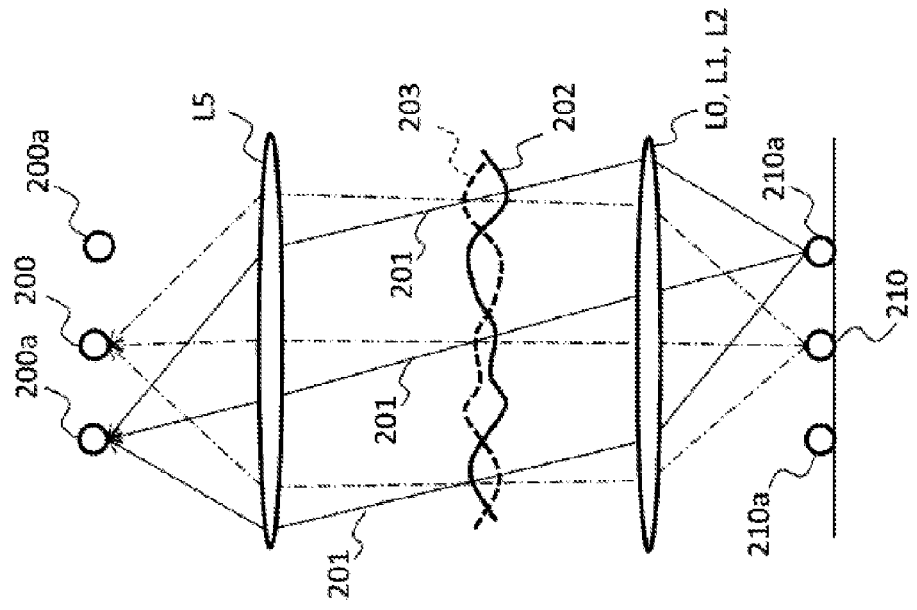
FIGS. 40A and 40B are conceptual diagrams illustrating principles of expansion of a viewing area.
Figure 40B:
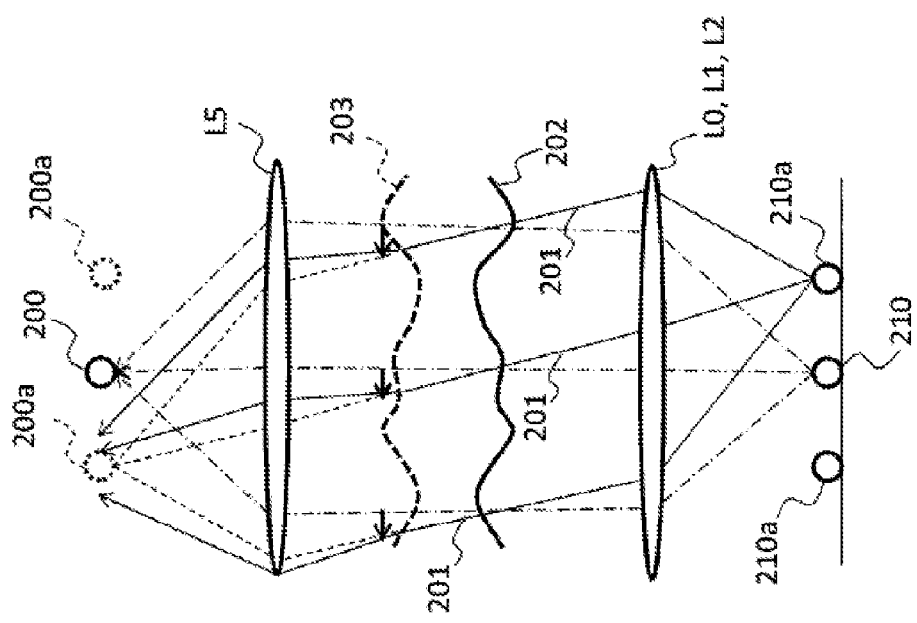

FIGS. 40A and 40B are conceptual diagrams showing the principle of expansion of the viewing area. In particular, taking notice of the area around the field of view, light beams 201 emitted from an object 210 pass obliquely through a fluctuation surface 202 and a correction surface 203. Accordingly, as illustrated in FIG. 40A, when the fluctuation surface 202 and the correction surface 203 do not match each other, position error occurs due to lateral displacement of the correction surface resulting from the skewing of the light beams 201. The light beams 201 thus do not converge on one point but images 200a corresponding to objects 210a positioned at surrounding areas become deteriorated. As a result, it can be understood that the accuracy of correction decreases at the surrounding areas and the effective range of the correction is limited to the central part.

In contrast, as illustrated in FIG. 40B, when the fluctuation surface 202 and the correction surface 203 are adjusted and aligned with each other according to the present invention, the fluctuation surface 202 and the correction surface 203 match each other. Accordingly, no position error occurs at the time of light transmission even when the light beams 201 travel obliquely. As a result, the accuracy of correction can be improved even when the skew of the light beams resulting from the refraction on the fluctuation surface 202 is large and the light beam travels obliquely in the areas surrounding the field of view. Accordingly, it has been confirmed that the viewing area was significantly expanded with higher resolution on the latter principles that the accuracy increases in the area surrounding the field of view to extend the correction range.

Figure 41A:
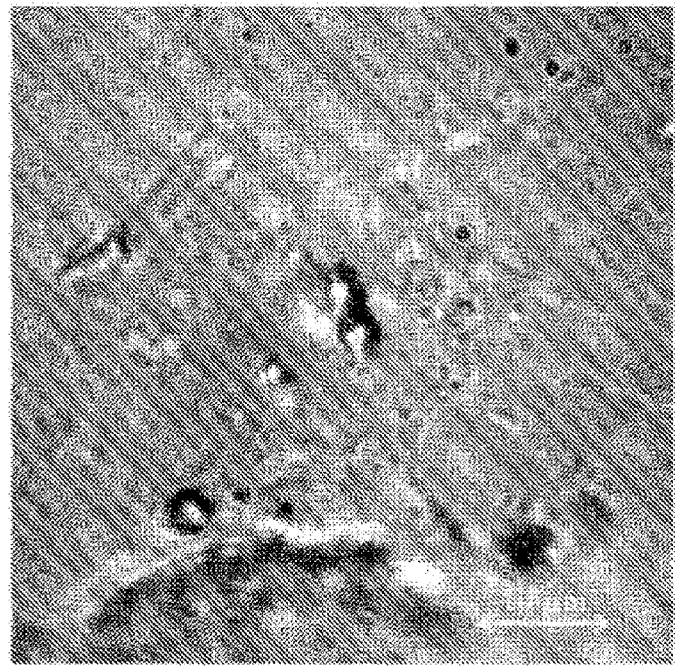
FIG. 41A is a photomicrograph of onion epidermal cells corrected by a conventional adaptive optics system without imaging-conjugated position adjustment.
Figure 41B:
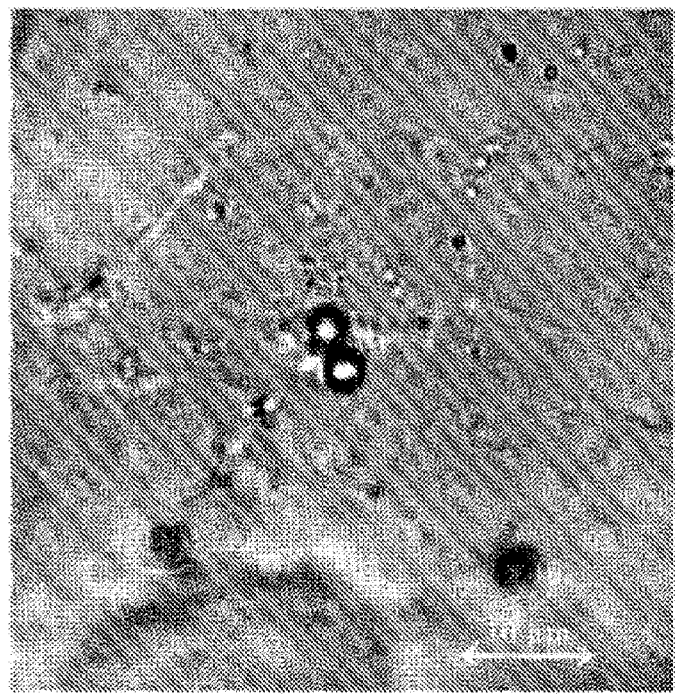
FIG. 41B is a photomicrograph of onion epidermal cells in which a fluctuation correction surface is corrected to be imaging-conjugated with a fluctuation layer by the adaptive optics system of the present invention.

Next, epidermal cells of an onion scale leaf were observed. Fluorescent beads were attached to the surface of the cells on the side opposite to the objective lens, and used as a reference object. FIG. 41A is a photomicrograph of onion epidermal cells taken such that wavefront correction is made by a conventional adaptive optics system without imaging-conjugated position adjustment, and FIG. 41B is a photomicrograph of onion epidermal cells taken such that wavefront correction is made by the adaptive optics system of the present invention while a fluctuation correction surface is imaging-conjugated with a fluctuation layer.

The image shown in FIG. 41A was acquired with imaging-conjugate between the correction surface and the opening pupil of the objective lens. In contrast, it can be seen that, in the image shown in FIG. 41B acquired with the imaging-conjugate between the fluctuation correction surface and the fluctuation surface, the definition of the image of the intracellular tissues is improved in a field of view of about 30 μm diameter centered around the fluorescent beads in the center of the image used as the reference object. Accordingly, it can be understood that the present invention is also effective on an actual biological specimen with a three-dimensional structure.

INDUSTRIAL APPLICABILITY

The adaptive optics system of the present invention is applicable to microscopic devices, astrometric telescopes, terrestrial telescopes, laser measurement devices, laser communication devices, underwater surveillance cameras, positioning devices, surveying devices, energy transmission via laser, gun-sights, monitors, long-distance imaging cameras, fiber scopes in endoscopes, GRIN (GRaded INdex: gradient index-type) fiber scopes, and other medical testing and diagnostic devices.

The conjugated position adjustment function for fluctuation correction layer is expected to be effective in accuracy improvement of general applications of adaptive optics. The applications of the adaptive optics include: the correction of fluctuations in astrometric telescopes, the correction of aberration in space telescopes, the stabilization of laser oscillators, the stabilization of laser optical systems, the elimination of speckle in laser optical systems, laser nuclear fusion, plasma density measurement devices, beam shaping in laser processors, ocular fundus cameras, ocular fundus imaging, ocular fundus laser treatment, the correction of aberration in medical laser devices, the correction of refraction in a biological body by medical laser, the correction of refraction resulting from a biological body at testing and diagnosis using medical devices, the correction of degradation at ground imaging from an artificial satellite, the correction of degradation at imaging of an artificial satellite from the ground, space optical communication equipment, space photon communication equipment, quantum light source, quantum entangled light source, and others.

REFERENCE SIGNS LIST

1: Specimen
2: Specimen stage
3: Light source
4, 5, 21, 22, 24, and 25: Slide stage
6, 16a, and 16b: Wavefront phase modulator
6a: Element of wavefront phase modulator
7, and 17a to 17c: Wavefront sensor
7a: Element of wavefront sensor
8: Imaging camera
9: Pupil camera
10 and 14: Computer 11: Image storage unit
12: Adaptive optical control unit
13: Wavefront sensor opening mirror image
30 and 31: Light source unit
80 and 81: Imaging unit
82: Confocal scanning unit
83: Multiphoton scanning detection unit
100: Observation target
101: Reference object
102: Fluctuation layer
103: Cover glass
104 and Lo: Objective lens
110, 111, L1 to L12, L1a, L1b, L2a, L2b, and L4a to L4c: Lens
200: Image
201: Light beam
202: Fluctuation surface
203: Correction surface
210: Object
BPF: Bandpass filter
BS1 to BS3: Beam splitter
C: Collimator
CM1 and CM2: Concave mirror
DP: Fourier diffraction surface
F1 to F3: Filter
GMX and GMY: Galvanometer mirror
LS: Laser light source
M1 to M6 and M1a to M1d: Mirror
P, P1, and P2: Pinhole
PH: Slit or pinhole
PL1 and PL2: Polarizing filter
PM: Phase-contrast mask
PMT: Photoelectron multiplier tube
PP1 and PP2: Wollaston polarizing prism
ST, and STa to STc: Field stop
TS: Telescope
WP1 and WP2: Wavelength plate

The invention claimed is:

1. An adaptive optics system comprising:
a wavefront phase modulator that makes aberration correction to incident light and emits the corrected light; and
an imaging-conjugated position adjustment mechanism that freely adjusts the position of a surface that is imaging-conjugated with a fluctuation correction surface formed by the wavefront phase modulator, wherein
the imaging-conjugated position adjustment mechanism is configured so that the position of the surface that is imaging-conjugated with the fluctuation correction surface can be freely adjusted within a specimen, wherein
the imaging-conjugated position adjustment mechanism is configured to freely adjust the position of the surface so that the fluctuation correction surface is to be imaging-conjugated with a fluctuation layer existing in the specimen, and wherein
the imaging-conjugated position adjustment mechanism includes an objective lens and a at least one lens, the at least one lens constituting relay lens, and the objective lens and the at least one lens are arranged sequentially in an optical path from the specimen to the wavefront phase modulator.

2. The adaptive optics system according to claim 1, wherein the position of the surface imaging-conjugated with the fluctuation correction surface in the specimen is freely adjusted by changing the optical distance between the objective lens and the at least one lens.

3. The adaptive optics system according to claim 2, wherein
a turn-back optical system including at least one mirror is arranged between the objective lens and the at least one lens, and
the turn-back optical system is moved in a direction parallel to an optical axis to change the optical distance between the objective lens and the at least one lens.

4. The adaptive optics system according to claim 1, wherein the position of the surface imaging-conjugated with the fluctuation correction surface in the specimen is freely adjusted by changing the optical distance between the at least one lens and the wavefront phase modulator.

5. The adaptive optics system according to claim 4, wherein
a turn-back optical system including at least one mirror is arranged between the at least one lens and the wavefront phase modulator, and
the turn-back optical system is moved in the direction parallel to an optical axis to change the optical distance between the at least one lens and the wavefront phase modulator.

6. The adaptive optics system according to claim 1, wherein
the at least one lens is a first lens and a second lens,
a turn-back optical system including at least one mirror is arranged between the first lens and the second lens, and
the turn-back optical system is moved in the direction parallel to an optical axis to change the optical distance between the first lens and the second lens.

7. The adaptive optics system according to claim 1, further comprising:
a wavefront sensor that detects a wavefront residual component included in the light corrected by the wavefront phase modulator; and
a first control unit that controls the wavefront phase modulator based on the results of detection by the wavefront sensor,
wherein the first control unit adjusts the wavefront phase modulator such that the wavefront phase of incident light on the wavefront sensor takes an offset value.

8. The adaptive optics system according to claim 1, further comprising a wavefront sensor that detects a wavefront residual component included in the light corrected by the wavefront phase modulator;
wherein a plurality of wavefront phase modulators and relay lenses are arranged to be imaging-conjugated onto different positions of the specimen in a depth direction between the specimen and the wavefront sensor.

9. The adaptive optics system according to claim 1, further comprising a wavefront sensor that detects a wavefront residual component included in the light corrected by the wavefront phase modulator;
wherein a plurality of wavefront sensors is provided.

10. The adaptive optics system according to claim 1, further comprising a wavefront sensor that detects a wavefront residual component included in the light corrected by the wavefront phase modulator;
wherein the wavefront sensor is arranged such that the alignment of elements is rotated 45° relative to the wavefront phase modulator.

11. The adaptive optics system according to claim 1,
further comprising a wavefront sensor that detects a wavefront residual component included in the light corrected by the wavefront phase modulator;
wherein the wavefront sensor is of a phase contrast type.

12. An optical device comprising the adaptive optics system according to claim 1, wherein
the optical device is a microscopic device, a telescope, a laser measurement device, a laser injection device, a camera, or a medical testing device, and wherein
the microscopic device is a fluorescence microscope, a differential interference microscope, a phase-contrast microscope, a super-resolution microscope, a scanning microscope, a multiphoton microscope, or a laser injection microscope.

13. The adaptive optics system according to claim 1, wherein the position of the surface imaging-conjugated with the fluctuation correction surface in the specimen is adjusted by displacement of a light path length of parallel light beam from an object.

14. The adaptive optics system according to claim 1, wherein the position of the surface imaging-conjugated with the fluctuation correction surface in the specimen is adjusted with keeping magnification ratio of the observation target constant.

15. The adaptive optics system according to claim 1, wherein the imaging-conjugated position adjustment mechanism is configured so that the adjustment of the imaging conjugation mechanism does not affect the focus of the observation target.

16. The adaptive optics system according to claim 1, wherein the imaging-conjugated position adjustment mechanism is configured to be able to adjust the position without making any influence on an image property of image of observation target.

17. The adaptive optics system according to claim 1, wherein the fluctuation correction surface is automatically imaging-conjugated with the fluctuation surface.

18. The adaptive optics system according to claim 1, further comprising:
a wavefront sensor; and
a beam splitter,
wherein a light path between the objective lens and the wavefront sensor is branched or placed with the beam splitter.

19. An adaptive optics system comprising:
a wavefront phase modulator that makes aberration correction to incident light and emits the corrected light; and
an imaging-conjugated position adjustment mechanism that freely adjusts the position of a surface that is imaging-conjugated with a fluctuation correction surface formed by the wavefront phase modulator, wherein
the imaging-conjugated position adjustment mechanism is configured so that the position of the surface that is imaging-conjugated with the fluctuation correction surface can be freely adjusted in a light path to a subject, wherein
the imaging-conjugated position adjustment mechanism is configured to freely adjust the position of the surface so that the fluctuation correction surface is to be imaging-conjugated with a position of fluctuations in the air in the light path to the subject.

20. The adaptive optics system according to claim 19, wherein the imaging-conjugated position adjustment mechanism includes at least one lens, the at least one lens constituting relay lens, and the at least one lens is arranged in the light path from the subject to the wavefront phase modulator.

* * * * *